US008821865B2

(12) United States Patent
Neu et al.

(10) Patent No.: US 8,821,865 B2
(45) Date of Patent: Sep. 2, 2014

(54) HIGH CONCENTRATION ANTI-TNFα ANTIBODY LIQUID FORMULATIONS

(75) Inventors: Michael Neu, Edingen-Neckarahuasen (DE); Markus Tschoepe, Hessheim (DE); Carsten Weber, Maxdorf (DE); Wolfgang Fraunhofer, Gurnee, IL (US); Laura Redden, Glenview, IL (US); Martin Gastens, Wachenheim (DE); Alexander Feick, Allschwil (CH)

(73) Assignee: Abbvie Biotechnology Ltd., Hamilton (BM)

( * ) Notice: Subject to any disclaimer, the term of this patent is extended or adjusted under 35 U.S.C. 154(b) by 0 days.

(21) Appl. No.: 13/294,692

(22) Filed: Nov. 11, 2011

(65) Prior Publication Data

US 2012/0263731 A1 Oct. 18, 2012

Related U.S. Application Data

(60) Provisional application No. 61/412,728, filed on Nov. 11, 2010, provisional application No. 61/413,960, filed on Nov. 15, 2010.

(51) Int. Cl.
*A61K 39/395* (2006.01)
*C07K 16/24* (2006.01)
*A61K 39/00* (2006.01)

(52) U.S. Cl.
CPC ......... *A61K 39/39591* (2013.01); *C07K 16/241* (2013.01); *C07K 2317/94* (2013.01); *A61K 2039/505* (2013.01); *C07K 2317/21* (2013.01)
USPC ...................................... 424/130.1; 424/133.1

(58) Field of Classification Search
None
See application file for complete search history.

(56) References Cited

U.S. PATENT DOCUMENTS

| | | | |
|---|---|---|---|
| 5,237,054 A | 8/1993 | Brinks et al. |
| 5,358,708 A | 10/1994 | Patel et al. |
| 5,654,403 A | 8/1997 | Smith et al. |
| 5,945,098 A | 8/1999 | Sarno et al. |
| 6,024,938 A | 2/2000 | Corbo et al. |
| 6,090,382 A | 7/2000 | Salfeld et al. |
| 6,165,467 A | 12/2000 | Hagiwara et al. |
| 6,171,586 B1 | 1/2001 | Lam et al. |
| 6,252,055 B1 | 6/2001 | Relton |
| 6,258,562 B1 | 7/2001 | Salfeld et al. |
| 6,485,725 B1 | 11/2002 | Hirao et al. |
| 6,485,932 B1 | 11/2002 | McInosh et al. |
| 6,509,015 B1 | 1/2003 | Salfeld et al. |
| 6,737,405 B2 | 5/2004 | Roemisch et al. |
| 6,818,613 B2 | 11/2004 | Sharma et al. |
| 6,875,432 B2 | 4/2005 | Liu et al. |
| 7,070,775 B2 | 7/2006 | Le et al. |
| 7,220,409 B2 | 5/2007 | Norman et al. |
| 7,223,394 B2 | 5/2007 | Salfeld et al. |
| 7,250,165 B2 | 7/2007 | Heavner et al. |
| 7,276,239 B2 | 10/2007 | Le et al. |
| 7,318,931 B2 | 1/2008 | Okumu et al. |
| 7,541,031 B2 | 6/2009 | Salfeld et al. |
| 7,588,761 B2 | 9/2009 | Salfeld et al. |
| 7,758,860 B2 | 7/2010 | Warne et al. |
| 7,863,426 B2 | 1/2011 | Wan et al. |
| 7,919,264 B2 | 4/2011 | Maksymowych et al. |
| 8,034,906 B2 | 10/2011 | Borhani et al. |
| 8,092,998 B2 | 1/2012 | Stuhlmuller et al. |
| 8,093,045 B2 | 1/2012 | Pla et al. |
| 8,187,836 B2 | 5/2012 | Hsieh |
| 8,197,813 B2 | 6/2012 | Salfeld et al. |
| 8,206,714 B2 | 6/2012 | Salfeld et al. |
| 8,216,583 B2 | 7/2012 | Kruase et al. |
| 8,231,876 B2 | 7/2012 | Wan et al. |
| 8,420,081 B2 | 4/2013 | Fraunhofer et al. |
| 2003/0012786 A1 | 1/2003 | Teoh et al. |
| 2003/0045454 A1 | 3/2003 | Okumu et al. |
| 2003/0049725 A1 | 3/2003 | Heavner et al. |
| 2003/0138417 A1 | 7/2003 | Kaisheva et al. |
| 2003/0161828 A1 | 8/2003 | Abdelghany et al. |
| 2003/0180287 A1 | 9/2003 | Gombotz et al. |
| 2003/0190316 A1 | 10/2003 | Kakuta et al. |
| 2003/0206898 A1 | 11/2003 | Fischkoff et al. |
| 2003/0219438 A1 | 11/2003 | Salfeld et al. |

(Continued)

FOREIGN PATENT DOCUMENTS

| | | |
|---|---|---|
| EP | 0486526 | 5/1992 |
| EP | 417191 | 10/1993 |

(Continued)

OTHER PUBLICATIONS

Harris et al., "Commercial manufacturing scale formulation and analytical characterization of therapeutic recombinant antibodies", Druge Development Research. (2004) vol. 61(3): 137-154.

Holt et al., "Domain antibodies: proteins for therapy, " *Trends in Immunology*, 2003;21 (11): 484-490.

Zhao et al., "Recent U.S. Patents on Protein Drug Formulation: 2000-2007," *Recent Patents on Drug Delivery and Formulation*, 2008; 2(3):200-208(9).

Wang et al."Antibody Structure, Instability, and Formulation," *J Pharmaceutical Sci*, 2007;96 (1): 1-26.

(Continued)

*Primary Examiner* — Yunsoo Kim

(74) *Attorney, Agent, or Firm* — McCarter & English, LLP; Cristin H. Cowles; Deborah L. Nagle

(57) ABSTRACT

The invention provides a liquid aqueous pharmaceutical formulation comprising a human anti-TNFa antibody, or antigen-binding portion thereof, which reduces pain associated with injection in a subject by at least about 50% when compared to injecting an otherwise identical formulation comprising at least one salt and/or at least one buffer. The invention also provides a liquid aqueous pharmaceutical formulation comprising a human anti-TNFa antibody, or antigen-binding portion thereof, having increased bioavailability upon subcutaneous administration into a subject. The formulation may comprise a therapeutic protein, such as a human anti-TNF-alpha antibody, or an antigen-binding portion thereof, or a biosimilar thereof.

11 Claims, 4 Drawing Sheets

(56) References Cited

U.S. PATENT DOCUMENTS

| | | |
|---|---|---|
| 2003/0235585 A1 | 12/2003 | Fischkoff et al. |
| 2004/0009172 A1 | 1/2004 | Fischkoff et al. |
| 2004/0028667 A1 | 2/2004 | Norman et al. |
| 2004/0033228 A1 | 2/2004 | Krause et al. |
| 2004/0038878 A1 | 2/2004 | Tanikawa et al. |
| 2004/0126372 A1 | 7/2004 | Banerjee et al. |
| 2004/0126373 A1 | 7/2004 | Banerjee et al. |
| 2004/0131614 A1 | 7/2004 | Banerjee et al. |
| 2004/0136989 A1 | 7/2004 | Banerjee et al. |
| 2004/0136990 A1 | 7/2004 | Banerjee et al. |
| 2004/0136991 A1 | 7/2004 | Banerjee et al. |
| 2004/0151722 A1 | 8/2004 | Banerjee et al. |
| 2004/0156835 A1 | 8/2004 | Imoto et al. |
| 2004/0166111 A1 | 8/2004 | Kaymakcalan et al. |
| 2004/0170623 A1 | 9/2004 | Arvinte et al. |
| 2004/0191243 A1 | 9/2004 | Chen et al. |
| 2004/0213785 A1 | 10/2004 | Yamazaki et al. |
| 2004/0219142 A1 | 11/2004 | Banerjee et al. |
| 2005/0053598 A1 | 3/2005 | Burke et al. |
| 2005/0118163 A1 | 6/2005 | Mizushima et al. |
| 2005/0118167 A1 | 6/2005 | Okada et al. |
| 2005/0119172 A1 | 6/2005 | Merkle |
| 2005/0214278 A1 | 9/2005 | Kakuta et al. |
| 2006/0009385 A1 | 1/2006 | Hoffman et al. |
| 2006/0083741 A1 | 4/2006 | Hoffman et al. |
| 2006/0088523 A1 | 4/2006 | Andya et al. |
| 2006/0153846 A1 | 7/2006 | Krause et al. |
| 2006/0159653 A1 | 7/2006 | Saito et al. |
| 2006/0182740 A1 | 8/2006 | Yang et al. |
| 2006/0210557 A1 | 9/2006 | Luisi et al. |
| 2006/0246073 A1 | 11/2006 | Knight et al. |
| 2006/0269543 A1 | 11/2006 | Chu |
| 2007/0020255 A1 | 1/2007 | Ueno et al. |
| 2007/0031402 A1 | 2/2007 | Zhang et al. |
| 2007/0036779 A1 | 2/2007 | Bardat et al. |
| 2007/0041905 A1 | 2/2007 | Hoffman et al. |
| 2007/0053871 A1 | 3/2007 | Li et al. |
| 2007/0053900 A1 | 3/2007 | Liu et al. |
| 2007/0053906 A1 | 3/2007 | Samaritani et al. |
| 2007/0071747 A1 | 3/2007 | Hoffman et al. |
| 2007/0081996 A1 | 4/2007 | Hoffman et al. |
| 2007/0172897 A1 | 7/2007 | Maksymowych et al. |
| 2007/0184050 A1 | 8/2007 | Ishikawa et al. |
| 2007/0190047 A1 | 8/2007 | Brych et al. |
| 2007/0197439 A1 | 8/2007 | Zhu et al. |
| 2007/0202104 A1 | 8/2007 | Banerjee et al. |
| 2007/0244299 A1 | 10/2007 | Jaber |
| 2007/0253984 A1 | 11/2007 | Khandke et al. |
| 2007/0292442 A1 | 12/2007 | Wan et al. |
| 2008/0003220 A1 | 1/2008 | Gokarn |
| 2008/0071063 A1 | 3/2008 | Allan et al. |
| 2008/0112953 A1 | 5/2008 | McAuley et al. |
| 2008/0118496 A1 | 5/2008 | Medich et al. |
| 2008/0124326 A1 | 5/2008 | Rehder et al. |
| 2008/0131374 A1 | 6/2008 | Medich et al. |
| 2008/0145383 A1 | 6/2008 | Zauner et al. |
| 2008/0016123 A1 | 7/2008 | Jones et al. |
| 2008/0166348 A1 | 7/2008 | Kupper et al. |
| 2008/0193466 A1 | 8/2008 | Banerjee et al. |
| 2008/0200655 A1 | 8/2008 | Sek |
| 2008/0227136 A1 | 9/2008 | Pla et al. |
| 2008/0275220 A1 | 11/2008 | Friess |
| 2008/0286280 A1 | 11/2008 | Kallmeyer et al. |
| 2008/0311043 A1 | 12/2008 | Hoffman et al. |
| 2009/0017472 A1 | 1/2009 | Stuhlmuller et al. |
| 2009/0028794 A1 | 1/2009 | Medich et al. |
| 2009/0054331 A1 | 2/2009 | Chen et al. |
| 2009/0068172 A1 | 3/2009 | Kaymakcalan et al. |
| 2009/0110679 A1 | 4/2009 | Li et al. |
| 2009/0123378 A1 | 5/2009 | Wong et al. |
| 2009/0148406 A1 | 6/2009 | Jezek |
| 2009/0148513 A1 | 6/2009 | Fraunhofer et al. |
| 2009/0155205 A1 | 6/2009 | Salfeld et al. |
| 2009/0226530 A1 | 9/2009 | Lassner et al. |
| 2009/0239259 A1 | 9/2009 | Hsieh et al. |
| 2009/0258018 A1 | 10/2009 | Medich et al. |
| 2009/0271164 A1 | 10/2009 | Peng et al. |
| 2009/0280065 A1 | 11/2009 | Willian et al. |
| 2009/0291062 A1 | 11/2009 | Fraunhofer et al. |
| 2009/0304682 A1 | 12/2009 | Hoffman et al. |
| 2009/0317399 A1 | 12/2009 | Pollack et al. |
| 2010/0003243 A1 | 1/2010 | Okun et al. |
| 2010/0016557 A1 | 1/2010 | Salfeld et al. |
| 2010/0021451 A1 | 1/2010 | Wong et al. |
| 2010/0028372 A1 | 2/2010 | Jezek |
| 2010/0028383 A1 | 2/2010 | Van Gelder et al. |
| 2010/0034823 A1 | 2/2010 | Borhani et al. |
| 2010/0040604 A1 | 2/2010 | Salfeld et al. |
| 2010/0040630 A1 | 2/2010 | Elden et al. |
| 2010/0113744 A1 | 5/2010 | Tsvetkova et al. |
| 2010/0129379 A1 | 5/2010 | Carpenter et al. |
| 2010/0160894 A1 | 6/2010 | Julian et al. |
| 2010/0278822 A1 | 11/2010 | Fraunhofer et al. |
| 2011/0002935 A1 | 1/2011 | Wan et al. |
| 2011/0014676 A1 | 1/2011 | Cowan et al. |
| 2011/0054414 A1 | 3/2011 | Shang et al. |
| 2011/0171227 A1 | 7/2011 | Okun et al. |
| 2011/0300151 A1 | 12/2011 | Okun et al. |
| 2012/0014956 A1 | 1/2012 | Kupper et al. |
| 2012/0077213 A1 | 3/2012 | Pla et al. |
| 2012/0107783 A1 | 5/2012 | Julian et al. |
| 2012/0129185 A1 | 5/2012 | Maksymowych et al. |
| 2012/0171123 A1 | 7/2012 | Medich et al. |
| 2012/0177596 A1 | 7/2012 | Fischkoff et al. |
| 2012/0178107 A1 | 7/2012 | Salfeld et al. |
| 2012/0219564 A1 | 8/2012 | Salfeld et al. |
| 2012/0251550 A1 | 10/2012 | Borhani et al. |
| 2012/0258114 A1 | 10/2012 | Salfeld et al. |
| 2012/0263731 A1 | 10/2012 | Tschoepe et al. |
| 2012/0282262 A1 | 11/2012 | Okun et al. |
| 2012/0282270 A1 | 11/2012 | Krause et al. |
| 2013/0004507 A1 | 1/2013 | Fischkoff et al. |
| 2013/0028903 A1 | 1/2013 | Wan et al. |
| 2013/0122011 A1 | 5/2013 | Hoffman et al. |
| 2013/0156760 A1 | 6/2013 | Fraunhofer et al. |
| 2013/0243786 A1 | 9/2013 | Banerjee et al. |
| 2014/0086929 A1 | 3/2014 | Krause et al. |
| 2014/0086930 A1 | 3/2014 | Krause et al. |
| 2014/0086931 A1 | 3/2014 | Krause et al. |

FOREIGN PATENT DOCUMENTS

| | | |
|---|---|---|
| EP | 0531539 | 6/1998 |
| EP | 1174148 | 1/2002 |
| EP | 1254666 | 11/2002 |
| JP | 02942412 B2 | 12/1991 |
| JP | 07236483 A2 | 2/1994 |
| WO | WO 86/00530 | 1/1986 |
| WO | WO 89/11298 | 11/1989 |
| WO | WO 90/011091 | 3/1990 |
| WO | WO 93/08837 | 5/1993 |
| WO | WO 95/03826 | 2/1995 |
| WO | WO 97/04801 | 2/1997 |
| WO | WO 97/29131 | 8/1997 |
| WO | WO 97/45140 | 12/1997 |
| WO | WO 98/22136 | 5/1998 |
| WO | WO 98/56418 | 12/1998 |
| WO | WO 99/37329 | 7/1999 |
| WO | WO 00/67789 | 11/2000 |
| WO | WO 01/43773 | 6/2001 |
| WO | WO 01/47554 | 7/2001 |
| WO | WO 02/072636 | 12/2001 |
| WO | WO 02/12500 | 2/2002 |
| WO | WO 02/12502 | 2/2002 |
| WO | WO 02/064166 | 2/2002 |
| WO | WO 02/30463 | 4/2002 |
| WO | WO 03/009817 | 7/2002 |
| WO | WO 02/100330 | 12/2002 |
| WO | WO 2004/039337 | 10/2003 |
| WO | WO 04/007520 | 1/2004 |
| WO | WO 2004/007520 | 1/2004 |
| WO | WO 2005/072772 | 1/2005 |
| WO | WO 2006/012500 | 7/2005 |
| WO | WO 2006/081320 | 1/2006 |

(56) References Cited

FOREIGN PATENT DOCUMENTS

| WO | WO 2006/138181 | 12/2006 |
| WO | WO 2006/014965 | 1/2007 |
| WO | WO 2008/108927 | 2/2008 |

OTHER PUBLICATIONS

Wang et al. "Instability, Stabilization, and Formulation of Liquid Protein Pharmaceuticals," *Int. K. Pharmaceutics*, 1999; 185:129-188.

Carpenter et al., "Rational Design of Stable Lyophilized Protein Formulations: Some Practical Advice" *Pharmaceutical Research*, vol. 14(8):969-975 (1997).

Akers et al., "Development and Manufacture of Protein Pharmaceuticals (Pharmaceutical Biotechnology)", Chapter 2: "Formulation Development of Protein Dosage Forms", 2002, Kluver Academic/Plenum, pub., New York.

Barrera et al., "Effects of treatment with a fully human antitumour necrosis factor alpha monoclonal antibody on the local and systemic homeostasis of interleukin 1 and TNFalpha in patients with rheumatoid arthritis," Ann. Rheum. Dis. 2001, 60(7):660-669.

Hillgren et al., "Protection mechanism of Tween 80 during freeze-thawing of a model protein," International Journal of Pharmaceutics, 2002, vol. 237: 57-69.

Adalimumab entry from National Library of Medicine website: www.nim.nih.gov/cgi/mesh; printed on Sep. 28, 2009.

Cleland et al., "A Specific Molar Ratio of Stabilizer to Protein is Required for Storage Stability of a Lyophilized Monoclonal Antibody," Journal of Pharmaceutical Sciences, 2001, vol. 90(3): 310-321.

Antoni et al., "Side effects of anti-TNF therapy: Current knowledge," *Clin Exp Rheumatol* 2002; 20(suppl. 28):S-152-S-157.

Hovgaard & Frokjaer (eds) "Pharmaceutical Formulation Development of Peptides and Proteins", CRC Press 1999.

Paborij et al., "Chemical and Physical Stability of Chimeric L6, a Mouse-Human Monoclonal Antibody ," *Pharm. Res.* 1994; 11, 5:764-771.

Wang, "Lyophilization and development of solid protein pharmaceuticals," *Int J Pharm* 2000; (203), 1-2:1-60.

den Broeder et al. Long term anti-tumour necrosis factor a monotherapy in rheumatoid arthritis: effect on radiological course and prognostic value of markers of cartilage turnover and endothelial activation, *Ann Rheum Dis*, 2002;61:311-318.

Cada et al. "Adalimumab", *Hospital Pharmacy* (2003) 38,6:568-580.

International Preliminary Examination Report for Application No. PCT/IB03/04502, dated Feb. 14, 2005.

International Search Report for Application No. PCT/IB03/04502 dated May 26, 2004.

Voigt, "Textbook of pharmaceutical technology" VCH, 384, 394, 395 (1987).

Pennington et al., Polyclonal and Monoclonal Antibody Therapy for Experimental *Pseudomonas aeruginosa* Pneumonia, Infect. Immun. (1986) vol. 54, p. 239-244.

Shimazato et al., "Suppression of Tumor Necrosis Factor Alpha Production by a Human Immunoglobulin Preparation for Intravenous Use", Infect. Immun. (1990), vol. 58, p. 1384-1390.

Sivasai et al., "Cytomegalovirus immune globulin intravenous (human) administration modulates immune response to alloantigens in sensitized renal transplant candidates ", Clin. Exp. Immunol., (2000), vol. 119, p. 559-565.

International Search Report for Application No. PCT/US11/160388 dated May 30, 2012.

U.S. Appl. No. 14/147,287, filed Jan. 3, 2014.

Garidal et al: "A rapid, sensitive and economical assessment of monoclonal antibody conformational stability by intrinsic tryptophan fluorescence spectroscopy," *Biotechnol. J.*.3(9-10):1201-11 (2008).

Schule et al: "Conformational analysis of protein secondary structure during spray-drying of antibody/mannitol formulations," *Eur. J. Pharm. Biopharm.* 65(1):1-9 (2007).

Vidanovic et al: "Effects of nonionic surfactants on the physical stability of immunoglobulin G in aqueous solution during mechanical agitation," *Pharmazie* 58(6):399-404 (2003).

Szenczi et al: "The effect of solvent environment on the conformation and stability of human polyclonal IgG in solution," *Biologicals* 34(1):5-14 (2006).

Fesinmeyer et al: "Effect of ions on agitation- and temperature-induced aggregation reactions of antibodies," *Pharm. Res.* 26(4):903-13 (2009).

Wang et al: "Opalescence of an IgG1 Monoclonal Antibody Formulation is Mediated by Ionic Strength and Excipients," *BioPharm Internatl.* 22(4) (2009).

Li et al: "Resurrecting Abandoned Proteins with Pure Water: CD and NMR Studies of Protein Fragments Solubilized in Salt-Free Water," *Biophys. J.* 91:4201-4209 (2006).

Tian et al: "Spectroscopic evaluation of the stabilization of humanized monoclonal antibodies in amino acid formulations," *Intl. J. Pharm.* 355:20-31(2007).

A = High Conc. Formulation 1
B = High Conc. Formulation 3
C = High Conc. Formulation 4
D = Commercial Formulation

SEQUENCE LISTING

```
<160> NUMBER OF SEQ ID NOS: 53

<210> SEQ ID NO 1
<211> LENGTH: 107
<212> TYPE: PRT
<213> ORGANISM: Artificial Sequence
<220> FEATURE:
<223> OTHER INFORMATION: human antibody

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Arg Tyr Asn Arg Ala Pro Tyr
                85                  90                  95
```

```
Thr Phe Gly Gln Gly Thr Lys Val Glu Ile Lys
            100                 105

<210> SEQ ID NO 2
<211> LENGTH: 121
<212> TYPE: PRT
<213> ORGANISM: Artificial Sequence
<220> FEATURE:
<223> OTHER INFORMATION: human antibody

<400> SEQUENCE: 2

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
        35                  40                  45

Ser Ala Ile Thr Trp Asn Ser Gly His Ile Asp Tyr Ala Asp Ser Val
    50                  55                  60

Glu Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Val Ser Tyr Leu Ser Thr Ala Ser Ser Leu Asp Tyr Trp Gly
            100                 105                 110

Gln Gly Thr Leu Val Thr Val Ser Ser
        115                 120

<210> SEQ ID NO 3
<211> LENGTH: 9
<212> TYPE: PRT
<213> ORGANISM: Artificial Sequence
<220> FEATURE:
<223> OTHER INFORMATION: human antibody
<220> FEATURE:
<221> NAME/KEY: VARIANT
<222> LOCATION: (9)
<223> OTHER INFORMATION: Xaa = Thr or Ala

<400> SEQUENCE: 3

Gln Arg Tyr Asn Arg Ala Pro Tyr Xaa
1               5

<210> SEQ ID NO 4
<211> LENGTH: 12
<212> TYPE: PRT
<213> ORGANISM: Artificial Sequence
<220> FEATURE:
<223> OTHER INFORMATION: human antibody
<220> FEATURE:
<221> NAME/KEY: VARIANT
<222> LOCATION: (12)
<223> OTHER INFORMATION: Xaa = Tyr or Asn

<400> SEQUENCE: 4

Val Ser Tyr Leu Ser Thr Ala Ser Ser Leu Asp Xaa
1               5                   10

<210> SEQ ID NO 5
<211> LENGTH: 7
<212> TYPE: PRT
<213> ORGANISM: Artificial Sequence
<220> FEATURE:
<223> OTHER INFORMATION: human antibody
```

```
<400> SEQUENCE: 5

Ala Ala Ser Thr Leu Gln Ser
 1               5

<210> SEQ ID NO 6
<211> LENGTH: 17
<212> TYPE: PRT
<213> ORGANISM: Artificial Sequence
<220> FEATURE:
<223> OTHER INFORMATION: human antibody

<400> SEQUENCE: 6

Ala Ile Thr Trp Asn Ser Gly His Ile Asp Tyr Ala Asp Ser Val Glu
 1               5                  10                  15

Gly

<210> SEQ ID NO 7
<211> LENGTH: 11
<212> TYPE: PRT
<213> ORGANISM: Artificial Sequence
<220> FEATURE:
<223> OTHER INFORMATION: human antibody

<400> SEQUENCE: 7

Arg Ala Ser Gln Gly Ile Arg Asn Tyr Leu Ala
 1               5                  10

<210> SEQ ID NO 8
<211> LENGTH: 5
<212> TYPE: PRT
<213> ORGANISM: Artificial Sequence
<220> FEATURE:
<223> OTHER INFORMATION: human antibody

<400> SEQUENCE: 8

Asp Tyr Ala Met His
 1               5

<210> SEQ ID NO 9
<211> LENGTH: 107
<212> TYPE: PRT
<213> ORGANISM: Artificial Sequence
<220> FEATURE:
<223> OTHER INFORMATION: 2SD4 light chain variable region

<400> SEQUENCE: 9

Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Tyr
                20                  25                  30

Leu Ala Trp Tyr Gln Gln Lys Pro Gly Lys Ala Pro Lys Leu Leu Ile
            35                  40                  45

Tyr Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Tyr
                85                  90                  95

Ala Phe Gly Gln Gly Thr Lys Val Glu Ile Lys
            100                 105

<210> SEQ ID NO 10
```

```
<211> LENGTH: 121
<212> TYPE: PRT
<213> ORGANISM: Artificial Sequence
<220> FEATURE:
<223> OTHER INFORMATION: 2SD4 heavy chain variable region

<400> SEQUENCE: 10

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Asp Trp Val
        35                  40                  45

Ser Ala Ile Thr Trp Asn Ser Gly His Ile Asp Tyr Ala Asp Ser Val
    50                  55                  60

Glu Gly Arg Phe Ala Val Ser Arg Asp Asn Ala Lys Asn Ala Leu Tyr
65                  70                  75                  80

Leu Gln Met Asn Ser Leu Arg Pro Glu Asp Thr Ala Val Tyr Tyr Cys
                85                  90                  95

Thr Lys Ala Ser Tyr Leu Ser Thr Ser Ser Leu Asp Asn Trp Gly
            100                 105                 110

Gln Gly Thr Leu Val Thr Val Ser Ser
        115                 120

<210> SEQ ID NO 11
<211> LENGTH: 9
<212> TYPE: PRT
<213> ORGANISM: Artificial Sequence
<220> FEATURE:
<223> OTHER INFORMATION: 2SD4 light chain variable region CDR3

<400> SEQUENCE: 11

Gln Lys Tyr Asn Ser Ala Pro Tyr Ala
1               5

<210> SEQ ID NO 12
<211> LENGTH: 9
<212> TYPE: PRT
<213> ORGANISM: Artificial Sequence
<220> FEATURE:
<223> OTHER INFORMATION: EP B12  light chain variable region CDR3

<400> SEQUENCE: 12

Gln Lys Tyr Asn Arg Ala Pro Tyr Ala
1               5

<210> SEQ ID NO 13
<211> LENGTH: 9
<212> TYPE: PRT
<213> ORGANISM: Artificial Sequence
<220> FEATURE:
<223> OTHER INFORMATION: VL10E4 light chain variable region CDR3

<400> SEQUENCE: 13

Gln Lys Tyr Gln Arg Ala Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: VL100A9 light chain variable region CDR3
```

```
<400> SEQUENCE: 14

Gln Lys Tyr Ser Ser Ala Pro Tyr Thr
1               5

<210> SEQ ID NO 15
<211> LENGTH: 9
<212> TYPE: PRT
<213> ORGANISM: Artificial Sequence
<220> FEATURE:
<223> OTHER INFORMATION: VLL100D2 light chain variable region CDR3

<400> SEQUENCE: 15

Gln Lys Tyr Asn Ser Ala Pro Tyr Thr
1               5

<210> SEQ ID NO 16
<211> LENGTH: 9
<212> TYPE: PRT
<213> ORGANISM: Artificial Sequence
<220> FEATURE:
<223> OTHER INFORMATION: VLL0F4 light chain variable region CDR3

<400> SEQUENCE: 16

Gln Lys Tyr Asn Arg Ala Pro Tyr Thr
1               5

<210> SEQ ID NO 17
<211> LENGTH: 9
<212> TYPE: PRT
<213> ORGANISM: Artificial Sequence
<220> FEATURE:
<223> OTHER INFORMATION: LOE5 light chain variable region CDR3

<400> SEQUENCE: 17

Gln Lys Tyr Asn Ser Ala Pro Tyr Tyr
1               5

<210> SEQ ID NO 18
<211> LENGTH: 9
<212> TYPE: PRT
<213> ORGANISM: Artificial Sequence
<220> FEATURE:
<223> OTHER INFORMATION: VLL0G7 light chain variable region CDR3

<400> SEQUENCE: 18

Gln Lys Tyr Asn Ser Ala Pro Tyr Asn
1               5

<210> SEQ ID NO 19
<211> LENGTH: 9
<212> TYPE: PRT
<213> ORGANISM: Artificial Sequence
<220> FEATURE:
<223> OTHER INFORMATION: VLL0G9 light chain variable region CDR3

<400> SEQUENCE: 19

Gln Lys Tyr Thr Ser Ala Pro Tyr Thr
1               5

<210> SEQ ID NO 20
<211> LENGTH: 9
<212> TYPE: PRT
<213> ORGANISM: Artificial Sequence
<220> FEATURE:
<223> OTHER INFORMATION: VLL0H1 light chain variable region CDR3

<400> SEQUENCE: 20
```

Gln Lys Tyr Asn Arg Ala Pro Tyr Asn
1               5

<210> SEQ ID NO 21
<211> LENGTH: 9
<212> TYPE: PRT
<213> ORGANISM: Artificial Sequence
<220> FEATURE:
<223> OTHER INFORMATION: VLL0H10 light chain variable region CDR3

<400> SEQUENCE: 21

Gln Lys Tyr Asn Ser Ala Ala Tyr Ser
1               5

<210> SEQ ID NO 22
<211> LENGTH: 9
<212> TYPE: PRT
<213> ORGANISM: Artificial Sequence
<220> FEATURE:
<223> OTHER INFORMATION: VL1B7 light chain variable region CDR3

<400> SEQUENCE: 22

Gln Gln Tyr Asn Ser Ala Pro Asp Thr
1               5

<210> SEQ ID NO 23
<211> LENGTH: 9
<212> TYPE: PRT
<213> ORGANISM: Artificial Sequence
<220> FEATURE:
<223> OTHER INFORMATION: VL1C1 light chain variable region CDR3

<400> SEQUENCE: 23

Gln Lys Tyr Asn Ser Asp Pro Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: VL0.1F4 light chain variable region CDR3

<400> SEQUENCE: 24

Gln Lys Tyr Ile Ser Ala Pro Tyr Thr
1               5

<210> SEQ ID NO 25
<211> LENGTH: 9
<212> TYPE: PRT
<213> ORGANISM: Artificial Sequence
<220> FEATURE:
<223> OTHER INFORMATION: VL0.1H8 light chain variable region CDR3

<400> SEQUENCE: 25

Gln Lys Tyr Asn Arg Pro Pro Tyr Thr
1               5

<210> SEQ ID NO 26
<211> LENGTH: 9
<212> TYPE: PRT
<213> ORGANISM: Artificial Sequence
<220> FEATURE:
<223> OTHER INFORMATION: L0E7.A light chain variable region CDR3

<400> SEQUENCE: 26

```
Gln Arg Tyr Asn Arg Ala Pro Tyr Ala
  1               5
```

<210> SEQ ID NO 27
<211> LENGTH: 12
<212> TYPE: PRT
<213> ORGANISM: Artificial Sequence
<220> FEATURE:
<223> OTHER INFORMATION: 2SD4 heavy chain variable region CDR3

<400> SEQUENCE: 27

```
Ala Ser Tyr Leu Ser Thr Ser Ser Ser Leu Asp Asn
  1               5                  10
```

<210> SEQ ID NO 28
<211> LENGTH: 12
<212> TYPE: PRT
<213> ORGANISM: Artificial Sequence
<220> FEATURE:
<223> OTHER INFORMATION: VH1B11 heavy chain variable region CDR3

<400> SEQUENCE: 28

```
Ala Ser Tyr Leu Ser Thr Ser Ser Ser Leu Asp Lys
  1               5                  10
```

<210> SEQ ID NO 29
<211> LENGTH: 12
<212> TYPE: PRT
<213> ORGANISM: Artificial Sequence
<220> FEATURE:
<223> OTHER INFORMATION: VH1D8 heavy chain variable region CDR3

<400> SEQUENCE: 29

```
Ala Ser Tyr Leu Ser Thr Ser Ser Ser Leu Asp Tyr
  1               5                  10
```

<210> SEQ ID NO 30
<211> LENGTH: 12
<212> TYPE: PRT
<213> ORGANISM: Artificial Sequence
<220> FEATURE:
<223> OTHER INFORMATION: VH1A11 heavy chain variable region CDR3

<400> SEQUENCE: 30

```
Ala Ser Tyr Leu Ser Thr Ser Ser Ser Leu Asp Asp
  1               5                  10
```

<210> SEQ ID NO 31
<211> LENGTH: 12
<212> TYPE: PRT
<213> ORGANISM: Artificial Sequence
<220> FEATURE:
<223> OTHER INFORMATION: VH1B12 heavy chain variable region CDR3

<400> SEQUENCE: 31

```
Ala Ser Tyr Leu Ser Thr Ser Phe Ser Leu Asp Tyr
  1               5                  10
```

<210> SEQ ID NO 32
<211> LENGTH: 12
<212> TYPE: PRT
<213> ORGANISM: Artificial Sequence
<220> FEATURE:
<223> OTHER INFORMATION: VH1E4 heavy chain variable region CDR3

<400> SEQUENCE: 32

```
Ala Ser Tyr Leu Ser Thr Ser Ser Ser Leu His Tyr
```

<210> SEQ ID NO 33
<211> LENGTH: 12
<212> TYPE: PRT
<213> ORGANISM: Artificial Sequence
<220> FEATURE:
<223> OTHER INFORMATION: VH1F6 heavy chain variable region CDR3

<400> SEQUENCE: 33

Ala Ser Phe Leu Ser Thr Ser Ser Ser Leu Glu Tyr
1               5                   10

<210> SEQ ID NO 34
<211> LENGTH: 12
<212> TYPE: PRT
<213> ORGANISM: Artificial Sequence
<220> FEATURE:
<223> OTHER INFORMATION: 3C-H2 heavy chain variable region CDR3

<400> SEQUENCE: 34

Ala Ser Tyr Leu Ser Thr Ala Ser Ser Leu Glu Tyr
1               5                   10

<210> SEQ ID NO 35
<211> LENGTH: 12
<212> TYPE: PRT
<213> ORGANISM: Artificial Sequence
<220> FEATURE:
<223> OTHER INFORMATION: VH1-D2.N heavy chain variable region CDR3

<400> SEQUENCE: 35

Val Ser Tyr Leu Ser Thr Ala Ser Ser Leu Asp Asn
1               5                   10

<210> SEQ ID NO 36
<211> LENGTH: 321
<212> TYPE: DNA
<213> ORGANISM: Artificial Sequence
<220> FEATURE:
<223> OTHER INFORMATION: adalimumab light chain variable region

<400> SEQUENCE: 36

```
gacatccaga tgacccagtc tccatcctcc ctgtctgcat ctgtagggga cagagtcacc      60
atcacttgtc gggcaagtca gggcatcaga aattacttag cctggtatca gcaaaaacca     120
gggaaagccc ctaagctcct gatctatgct gcatccactt tgcaatcagg ggtcccatct     180
cggttcagtg gcagtggatc tgggacagat ttcactctca ccatcagcag cctacagcct     240
gaagatgttg caacttatta ctgtcaaagg tataaccgtg caccgtatac ttttggccag     300
gggaccaagg tggaaatcaa a                                                321
```

<210> SEQ ID NO 37
<211> LENGTH: 363
<212> TYPE: DNA
<213> ORGANISM: Artificial Sequence
<220> FEATURE:
<223> OTHER INFORMATION: adalimumab heavy chain variable region

<400> SEQUENCE: 37

```
gaggtgcagc tggtggagtc tgggggaggc ttggtacagc ccggcaggtc cctgagactc      60
tcctgtgcgg cctctggatt cacctttgat gattatgcca tgcactgggt ccggcaagct     120
ccagggaagg gcctggaatg ggtctcagct atcacttgga atagtggtca catagactat     180
```

```
gcggactctg tggagggccg attcaccatc tccagagaca acgccaagaa ctccctgtat    240
ctgcaaatga acagtctgag agctgaggat acggccgtat attactgtgc gaaagtctcg    300
taccttagca ccgcgtcctc ccttgactat tggggccaag gtaccctggt caccgtctcg    360
agt                                                                  363
```

<210> SEQ ID NO 38
<211> LENGTH: 6
<212> TYPE: PRT
<213> ORGANISM: Homo sapiens

<400> SEQUENCE: 38

His Gly Ser His Asp Asn
1               5

<210> SEQ ID NO 39
<211> LENGTH: 12
<212> TYPE: PRT
<213> ORGANISM: Homo sapiens

<400> SEQUENCE: 39

Gln Ser Tyr Asp Arg Tyr Thr His Pro Ala Leu Leu
1               5                   10

<210> SEQ ID NO 40
<211> LENGTH: 17
<212> TYPE: PRT
<213> ORGANISM: Homo sapiens

<400> SEQUENCE: 40

Phe Ile Arg Tyr Asp Gly Ser Asn Lys Tyr Tyr Ala Asp Ser Val Lys
1               5                   10                  15

Gly

<210> SEQ ID NO 41
<211> LENGTH: 7
<212> TYPE: PRT
<213> ORGANISM: Homo sapiens

<400> SEQUENCE: 41

Tyr Asn Asp Gln Arg Pro Ser
1               5

<210> SEQ ID NO 42
<211> LENGTH: 9
<212> TYPE: PRT
<213> ORGANISM: Homo sapiens

<400> SEQUENCE: 42

Phe Thr Phe Ser Ser Tyr Gly Met His
1               5

<210> SEQ ID NO 43
<211> LENGTH: 13
<212> TYPE: PRT
<213> ORGANISM: Homo sapiens

<400> SEQUENCE: 43

Ser Gly Ser Arg Ser Asn Ile Gly Ser Asn Thr Val Lys
1               5                   10

<210> SEQ ID NO 44
<211> LENGTH: 115

```
<212> TYPE: PRT
<213> ORGANISM: Homo sapiens

<400> SEQUENCE: 44

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Phe Ile Arg Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Lys Thr His Gly Ser His Asp Asn Trp Gly Gln Gly Thr Met Val Thr
            100                 105                 110

Val Ser Ser
        115

<210> SEQ ID NO 45
<211> LENGTH: 112
<212> TYPE: PRT
<213> ORGANISM: Homo sapiens

<400> SEQUENCE: 45

Gln Ser Val Leu Thr Gln Pro Pro Ser Val Ser Gly Ala Pro Gly Gln
 1               5                  10                  15

Arg Val Thr Ile Ser Cys Ser Gly Ser Arg Ser Asn Ile Gly Ser Asn
                20                  25                  30

Thr Val Lys Trp Tyr Gln Gln Leu Pro Gly Thr Ala Pro Lys Leu Leu
            35                  40                  45

Ile Tyr Tyr Asn Asp Gln Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Gln Ser Tyr Asp Arg Tyr Thr
                85                  90                  95

His Pro Ala Leu Leu Phe Gly Thr Gly Thr Lys Val Thr Val Leu Gly
            100                 105                 110

<210> SEQ ID NO 46
<211> LENGTH: 16
<212> TYPE: PRT
<213> ORGANISM: Homo Sapiens

<400> SEQUENCE: 46

Ser Ile His Asn Arg Gly Thr Ile Phe Tyr Leu Asp Ser Val Lys Gly
 1               5                  10                  15

<210> SEQ ID NO 47
<211> LENGTH: 10
<212> TYPE: PRT
<213> ORGANISM: Homo Sapiens

<400> SEQUENCE: 47

Gly Arg Ser Asn Ser Tyr Ala Met Asp Tyr
 1               5                  10
```

<210> SEQ ID NO 48
<211> LENGTH: 16
<212> TYPE: PRT
<213> ORGANISM: Homo Sapiens

<400> SEQUENCE: 48

Arg Ser Thr Gln Thr Leu Val His Arg Asn Gly Asp Thr Tyr Leu Glu
1               5                   10                  15

<210> SEQ ID NO 49
<211> LENGTH: 7
<212> TYPE: PRT
<213> ORGANISM: Homo Sapiens

<400> SEQUENCE: 49

Lys Val Ser Asn Arg Phe Ser
1               5

<210> SEQ ID NO 50
<211> LENGTH: 9
<212> TYPE: PRT
<213> ORGANISM: Homo Sapiens

<400> SEQUENCE: 50

Phe Gln Gly Ser His Val Pro Tyr Thr
1               5

<210> SEQ ID NO 51
<211> LENGTH: 30
<212> TYPE: PRT
<213> ORGANISM: Homo Sapiens

<400> SEQUENCE: 51

Gln Val Gln Leu Val Gln Ser Gly Ala Glu Val Lys Lys Pro Gly Ala Ser Val
1               5                   10                  15

Lys Val Ser Cys Lys Ala Ser Gly Tyr Thr Phe Thr
    20                  25                  30

<210> SEQ ID NO 52
<211> LENGTH: 13
<212> TYPE: PRT
<213> ORGANISM: Homo Sapiens

<400> SEQUENCE: 52

Trp Arg Gln Ala Pro Gly Gln Gly Leu Glu Trp Met Gly
1               5                   10

<210> SEQ ID NO 53
<211> LENGTH: 32
<212> TYPE: PRT
<213> ORGANISM: Homo Sapiens

<400> SEQUENCE: 53

Arg Val Thr Met Thr Arg Asp Thr Ser Thr Ser Thr Val Tyr Met Glu Leu Ser
1               5                   10                  15

Ser Leu Arg Ser Glu Asp Thr Ala Val Tyr Tyr Cys Ala Arg
    20                  25                  30

HIGH CONCENTRATION ANTI-TNFα ANTIBODY LIQUID FORMULATIONS

RELATED APPLICATIONS

This application claims priority to U.S. Provisional Application No. 61/412,728 filed on Nov. 11, 2010 and U.S. Provisional Application No. 61/413,960 filed on Nov. 15, 2010, the entire contents of which are incorporated herein by this reference.

BACKGROUND OF THE INVENTION

The formulation of therapeutic proteins, such as antibodies, is often a challenge given the numerous desirable properties that the formulation must have to be economically and therapeutically successful, e.g., stability, suitability for administration, concentration. During manufacturing, storage, and delivery, therapeutic proteins have been known to undergo physical and chemical degradations. These instabilities can reduce the potency of the protein and increase the risk of adverse events in patients, and, therefore, significantly impact regulatory approval (see, e.g., Wang et al. *J. Pharm. Sci.* 96:1, 2007). As such, a stable protein formulation is essential to the success of a therapeutic protein.

To be effective, many therapeutic proteins require the administration of high doses, which, ideally, are formulated in high concentration formulations. High protein concentration formulations are desirable as they can impact the mode (e.g., intravenous vs. subcutaneous) and frequency of administration of the drug to a subject.

Despite the benefits of high protein concentration formulations, formulating high concentration therapeutic proteins presents numerous challenges. For example, increasing protein concentration often negatively impacts protein aggregation, solubility, stability, and viscosity (see, e.g., Shire et al. *J. Pharm. Sci.* 93:1390, 2004). Increased viscosity, which is a very common challenge for high protein solutions, can have negative ramifications on administration of the formulation, e.g., felt pain and burning syndromes and limitations in manufacturing, processing, fill-finish and drug delivery device options (see, e.g., Shire et al. *J. Pharm. Sci.* 93:1390, 2004). Even for therapeutic proteins having common structural features, e.g., antibodies, approved formulations to date have had varying ingredients and ranges of concentrations. For example, the anti-CD20 antibody Rituxan is formulated for intravenous administration at a concentration of 10 mg/mL, while the anti-RSV antibody Synagis is formulated for intramuscular administration at a concentration of 100 mg/mL. Thus, high protein formulations, especially antibody formulations, which can be used for therapeutic purposes remain a challenge.

Another challenge associated with therapeutic proteins, such as antibodies, is drug delivery. While self-administering devices allow patients to avoid unnecessary trips to medical facilities to receive treatments, patients' self-awareness and fear of the pain associated with self-administration may frequently impact self-administered drug delivery. Moreover, formulations having high concentrations of protein may have high viscosity resulting in increased pain upon delivery, particularly for subcutaneous administration. Thus, there is especially a need for high concentration formulations that reduce pain associated with drug delivery (e.g., self-injection).

Accordingly, there is a need for stable, high concentration protein formulations that provide dosing and administrative advantages, particularly with respect to a decrease in pain for the patient and/or improved bioavailability.

SUMMARY OF THE INVENTION

The present invention is based, at least in part, on the discovery of new high-concentration formulations for therapeutic antibodies (including human anti-TNF-α antibodies, or antigen-binding fragments thereof, e.g., adalimumab). The formulations of the invention provide a number of surprising characteristics given the high concentration of the therapeutic antibody. Specifically, the present invention provides pharmaceutical formulations comprising human anti-TNFα antibodies which surprisingly have improved bioavailability or decreased pain upon subcutaneous injection.

In particular, the present invention is based, at least partly, on the unexpected and surprising discovery that a formulation having a high antibody concentration, a surfactant, and a polyol, provides dramatically reduced pain to the patient during drug delivery, particularly subcutaneous administration of the antibody through, for example, self-injection. The formulations of the invention are established, at least in part, on the surprising finding that a therapeutic protein (e.g., an anti-TNF-alpha antibody, or antigen-binding portion thereof), can remain soluble at a high protein concentration (e.g., at least about 40, 45, 50, 55, 60, 65, 70, 75, 80, 85, 90, 96, 100, 105, 110 mg/ml, or more) and maintain a viscosity suitable for injection (e.g., subcutaneous administration). The formulation of the present invention is further surprising, in that the formulation does not contain a buffer or a salt, yet has a high concentration of antibody. Notably, the formulation of the invention reduces pain associated with injection in a patient by at least about 50% (e.g., at least about 60%, 65%, 70%, 75%, 80%, 85%, 90% or more) when compared to injecting an otherwise identical formulation comprising at least one salt and/or at least one buffer.

Thus, in one aspect, the invention provides a liquid aqueous formulation comprising an anti-TNFα antibody, or antigen-binding portion thereof; a surfactant; and, a polyol; wherein the formulation does not contain a buffer or a salt, and reduces pain associated with injection in a patient by at least about 50% (e.g., at least about 60%, 65%, 70%, 75%, 80%, 85%, 90% or more) when compared to injecting an otherwise identical formulation comprising at least one salt and/or at least one buffer.

In another aspect, the invention provides a liquid aqueous formulation comprising an isolated human anti-TNFα antibody, or an antigen-binding portion thereof, a surfactant, and less than 50 mg/mL of a polyol, wherein injection of the formulation into a human subject results in a Pain Visual Analog Scale (VAS) score of less than 1.0. In one embodiment, the invention provides a liquid aqueous formulation consisting essentially of an isolated human anti-TNFα antibody, or an antigen-binding portion thereof, a surfactant, and less than 50 mg/mL of a polyol, wherein injection of the formulation into a human subject results in a Pain Visual Analog Scale (VAS) score of less than 1.0. In one embodiment, the VAS scale is from 0 (no pain) to 10 (excruciating pain)

In a further aspect, the invention provides a liquid aqueous formulation comprising an isolated human anti-TNFα antibody, or an antigen-binding portion thereof, a surfactant, and less than 50 mg/ml of a polyol, wherein the formulation does not contain a buffer and a salt, and wherein injection of the formulation reduces pain associated with the injection in a human subject by at least about 50% when compared to injection of an otherwise identical formulation that comprises a salt and/or a buffer. In one embodiment, the otherwise identical comprises a citrate and phosphate buffer and sodium chloride.

The invention further provides a liquid aqueous formulation comprising an anti-TNFα antibody or antigen-binding portion thereof, at a concentration of at least about 50 mg/mL; a surfactant; and, a polyol, wherein the formulation has a conductivity of less than about 2 mS/cm. In one embodiment, the formulation has a conductivity of less than 1 mS/cm. In another embodiment, the formulation has a conductivity of less than 0.9 mS/cm.

The invention also provides, in another embodiment, a liquid aqueous formulation comprising an anti-TNFα antibody or antigen-binding portion thereof, at a concentration of at least about 50 mg/mL; a surfactant; and, a polyol, wherein the antibody, or antigen-binding portion thereof, has a hydrodynamic diameter of less than 4 nm in the formulation. In one embodiment, the antibody or antigen-binding portion thereof, has a hydrodynamic diameter of less than 3 nm in the formulation.

The present invention also provides a liquid aqueous formulation comprising an isolated human anti-TNFα antibody, or an antigen-binding portion thereof; a surfactant; and, less than 50 mg/ml of a polyol; wherein the formulation has a characteristic selected from the group consisting of a conductivity of less than about 2 mS/cm; a hydrodynamic diameter ($D_h$) which is at least about 50% less than the $D_h$ of the protein in a buffered solution at a given concentration; and a hydrodynamic diameter ($D_h$) of less than about 4 nm. In one embodiment, the formulation has a conductivity of less than about 1 mS/cm. In another embodiment, the formulation has a conductivity of less than about 0.9 mS/cm. In one embodiment, the antibody or antigen-binding portion thereof, has a hydrodynamic diameter of less than about 3 nm in the formulation. In another embodiment, the antibody or antigen-binding portion thereof, has a hydrodynamic diameter of less than about 2 nm in the formulation.

The invention also provides a liquid aqueous formulation consisting essentially of an anti-TNFα antibody or antigen-binding portion thereof; a surfactant; and, a polyol; wherein the concentration of the anti-TNFα antibody or antigen-binding portion thereof is at least about 50 mg/mL, 75 mg/mL, 100 mg/mL, or greater than 100 mg/mL.

In a particular embodiment, the invention provides a liquid aqueous formulation consisting essentially of a concentration of 90-110 mg/ml of an isolated human anti-TNFα antibody, or an antigen-binding portion thereof, having a light chain variable region (LCVR) having a CDR3 domain comprising the amino acid sequence of SEQ ID NO: 3, or modified from SEQ ID NO: 3 by a single alanine substitution at position 1, 4, 5, 7 or 8, a CDR2 domain comprising the amino acid sequence of SEQ ID NO: 5, and a CDR1 domain comprising the amino acid sequence of SEQ ID NO: 7; and having a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11, a CDR2 domain comprising the amino acid sequence of SEQ ID NO: 6, and a CDR1 domain comprising the amino acid sequence of SEQ ID NO: 8; a polysorbate, e.g., polysorbate 80; and, about 38-46 mg/ml of a polyol, e.g., mannitol.

In another aspect, the present invention provides a liquid aqueous formulation comprising an isolated human anti-TNFα antibody, or an antigen-binding portion thereof; a surfactant; and, less than 50 mg/ml of a polyol; wherein the formulation is stable up to about 30 degrees C. for at least about 6 days, about 10, days, or about 14 days, or is stable at about 28 degrees C. for up to about 24 months.

In another aspect, the invention provides a method of administering an isolated human anti-TNFα antibody, or an antigen-binding portion thereof, to a subject such that injection pain is reduced upon administration, said method comprising subcutaneously administering to the subject a formulation comprising the antibody, or antigen-binding portion thereof, such that injection pain is reduced upon administration, wherein the formulation comprises more than 50 mg/ml of the antibody, or antigen-binding portion thereof; a surfactant; and less than 50 mg/ml of a polyol. In one embodiment, the injection pain is determined to be less than 1.0 according to a Pain Visual Analog Scale (VAS).

In certain embodiments, pain associated with injection is assessed using a pain visual analog scale (VAS). In one embodiment, the VAS scale is from 0 (no pain) to 10 (excruciating pain)

In certain embodiments, the pain associated with injection is assessed after injection (e.g., immediately, no more than 1, 2, 3, 4, 5, 6, 7, 8, 9, 10 minutes, or no more than 15 minutes after injection).

In certain embodiments, the formulation reduces pain associated with injection in the patient by at least about 60%, 70%, 80% or more, when compared to injecting the otherwise identical formulation comprising the at least one salt and/or at least one buffer.

The invention further provides a liquid aqueous formulation comprising an anti-TNFα antibody or antigen-binding portion thereof, at a concentration of at least about 50, 75, 100 mg/mL, or greater than 100 mg/mL; a surfactant; and, a polyol; wherein the formulation does not contain a buffer and a salt.

In another aspect, the invention provides a liquid aqueous formulation comprising an isolated human anti-TNFα antibody, or an antigen-binding portion thereof; a surfactant; and, less than 50 mg/ml of a polyol; wherein the formulation is stable for up to about 30 degrees C. for at least about 6 days. In one embodiment, the formulation is stable at room temperature for at least about 7 days. In one embodiment, the formulation is stable at room temperature for at least about 8 days. In one embodiment, the formulation is stable at room temperature for at least about 9 days. In one embodiment, the formulation is stable at room temperature for at least about 10 days. In one embodiment, the formulation is stable at room temperature for at least about 11 days. In one embodiment, the formulation is stable at room temperature for at least about 12 days. In one embodiment, the formulation is stable at room temperature for at least about 13 days. In one embodiment, the formulation is stable at room temperature for at least about 14 days. In one embodiment, the formulation is stable at room temperature for at least about 15 days.

In one embodiment, the polyol used in the formulation of the invention is mannitol or sorbitol.

In one embodiment, the formulation of the invention contains about 20-60 mg/mL mannitol, or, alternatively, about 30-50 mg/mL. In one embodiment, the formulation contains about 38-46 mg/ml of mannitol.

The present invention is also based, at least in part, on the unexpected and surprising discovery that a formulation having a high antibody concentration and a surfactant provides notably higher bioavailability than similar formulations containing additional excipients, such as a buffer, a polyol and/or a salt.

Thus, in one aspect, the invention provides a liquid aqueous formulation comprising a surfactant and 30-90 mg of an isolated human anti-TNFα antibody or antigen-binding portion, wherein the formulation has an antibody concentration of 90-110 mg/ml, and wherein the formulation provides increased bioavailability of the antibody, or antigen-binding portion thereof, to a human subject upon subcutaneous injection of the formulation relative to a formulation comprising a citrate phosphate buffer, sodium chloride, and mannitol.

In one aspect, the invention provides a liquid aqueous formulation consisting essentially of a surfactant and 30-90 mg of an isolated human anti-TNFα antibody or antigen-binding portion, wherein the concentration of the antibody, or antigen-binding portion thereof, is 90-110 mg/ml.

In another aspect, the invention provides a liquid aqueous formulation comprising a surfactant and 30-90 mg of an isolated human anti-TNFα antibody, or an antigen-binding portion, wherein the formulation has an antibody concentration of 90-110 mg/ml, and wherein the formulation provides increased bioavailability of the antibody, or antigen-binding portion thereof, in a human subject upon subcutaneous injection of the formulation, such that the antibody or antigen-binding portion thereof, has an $AUC_{0-360}$ greater than about 1300 µg*hr/ml.

In another aspect, the invention provides a method for improving the bioavailability of an isolated human anti-TNFα antibody, or an antigen-binding portion thereof, in a human subject, said method comprising administering a formulation comprising an effective amount of the antibody, or antigen-binding portion thereof, and a surfactant to the subject such that the bioavailability of the antibody, or antigen-binding portion thereof, is improved, wherein the formulation does not contain a buffer, a polyol, or a salt.

In a further aspect, the invention provides a method of improving the bioavailability of an isolated human anti-TNFα antibody, or an antigen-binding portion thereof, in a subject, said method comprising administering a formulation comprising an effective amount of the antibody, or antigen-binding portion thereof, and a surfactant to the subject such that the bioavailability of the antibody, or antigen-binding portion thereof, in the subject is improved, at least about 15% over a second formulation, wherein the formulation does not contain a buffer, a polyol, or a salt, and wherein the second formulation comprises a buffer, a polyol, and a salt. In one embodiment, the bioavailability of the antibody, or antigen-binding portion thereof, is improved at least about 30% over the second formulation. In one embodiment, the bioavailability of the antibody, or antigen-binding portion thereof, is improved at least about 40% over the second formulation.

The invention further provides a method of improving the bioavailability of an isolated human anti-TNFα antibody, or an antigen-binding portion thereof, in a human subject, said method comprising administering a formulation comprising a surfactant and an effective amount of the antibody, or antigen-binding portion thereof, to the subject such that the bioavailability of the antibody, or antigen-binding portion thereof, is improved, wherein the formulation has a characteristic selected from the group consisting of a conductivity of less than about 2 mS/cm; the antibody, or antigen-binding portion thereof, has a hydrodynamic diameter ($D_h$) which is at least about 50% less than the $D_h$ of the antibody, or antigen-binding portion thereof, in a buffered solution at the given concentration; and the antibody, or antigen-binding portion thereof, has a hydrodynamic diameter ($D_h$) of less than about 4 nm. In one embodiment, the formulation has a conductivity of less than about 1 mS/cm. In another embodiment, the formulation has a conductivity of less than about 0.9 mS/cm. In one embodiment, the antibody or antigen-binding portion thereof, has a hydrodynamic diameter of less than about 3 nm in the formulation.

In one embodiment, the bioavailability is determined according to either an AUC level or a Cmax. In one embodiment, the bioavailability is determined according to either an $AUC_{0-360}$ or an $AUC_{0-1344}$. In one embodiment, the bioavailability of the antibody, or antigen-binding portion thereof, is an $AUC_{0-360}$ greater than about 1300 µg*hr/ml when subcutaneously injected into the human subject.

In certain embodiments, the anti-TNFα antibody is an isolated human antibody (e.g., a human IgG1 kappa antibody), a humanized antibody, a chimeric antibody, or a murine antibody. For example, the chimeric antibody may be infliximab or a biosimilar thereof, and the human antibody may be golimumab or adalimumab, or a biosimilar thereof.

In one embodiment, the human anti-TNFα antibody, or an antigen-binding portion thereof, is an IgG1 or an IgG4.

In one embodiment, human anti-TNFα antibody, or an antigen-binding portion thereof, dissociates from human TNFα with a $K_d$ of $1\times10^{-8}$ M or less and has a $k_{off}$ rate constant of $1\times10^{-3}$ s$^{-1}$ or less, both determined by surface plasmon resonance. In certain embodiments, the human anti-TNFα antibody, or an antigen-binding portion thereof, dissociates from human TNFα with a $K_d$ of $1\times10^{-8}$ M or less and a $k_{off}$ rate constant of $1\times10^{-3}$ s$^{-1}$ or less, both determined by surface plasmon resonance, and neutralizes human TNFα cytotoxicity in a standard in vitro L929 assay with an $IC_{50}$ of $1\times10^{-7}$ M or less.

In certain embodiments, the human anti-TNFα antibody, or an antigen-binding portion thereof, has the following characteristics: dissociates from human TNFα with a $k_{off}$ rate constant of $1\times10^{-3}$ s$^{-1}$ or less, as determined by surface plasmon resonance; has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9; and, (c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In certain embodiments, the human anti-TNFα antibody, or an antigen-binding portion thereof, has a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11.

In certain embodiments, the human anti-TNFα antibody, or an antigen-binding portion thereof, has a light chain variable region (LCVR) having a CDR3 domain comprising the amino acid sequence of SEQ ID NO: 3, or modified from SEQ ID NO: 3 by a single alanine substitution at position 1, 4, 5, 7 or 8, a CDR2 domain comprising the amino acid sequence of SEQ ID NO: 5, and a CDR1 domain comprising the amino acid sequence of SEQ ID NO: 7; and has a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11, a CDR2 domain comprising the amino acid sequence of SEQ ID NO: 6, and a CDR1 domain comprising the amino acid sequence of SEQ ID NO: 8.

In certain embodiments, the human anti-TNFα antibody, or an antigen-binding portion thereof, has a light chain variable region (LCVR) comprising the amino acid sequence of SEQ ID NO: 1 and a heavy chain variable region (HCVR) comprising the amino acid sequence of SEQ ID NO: 2.

In one embodiment, the human anti-TNFα antibody, or an antigen-binding portion thereof, comprises the CDRs corresponding to adalimumab.

In one embodiment, the human anti-TNFα antibody, or an antigen-binding portion thereof, is adalimumab or golimumab, or a biosimilar thereof.

In certain embodiments, the concentration of the human anti-TNFα antibody, or antigen-binding portion thereof, in the formulation is at least about 50 mg/mL, about 75 mg/mL, about 100 mg/mL, or greater than 100 mg/mL. In one embodiment, the concentration of the human anti-TNFα antibody, or antigen-binding portion thereof, in the formulation of the invention is 90-110 mg/ml. In one embodiment, the concentration of the human anti-TNFα antibody, or antigen-binding portion thereof, in the formulation of the invention is 95-105 mg/ml. In one embodiment, the formulation comprises more than 75 mg/ml of the antibody, or antigen-binding portion thereof. In one embodiment, the invention provides a stable, liquid aqueous formulation comprising a high concentration, e.g., 75-125 mg/mL, of a human anti-hTNFα antibody.

In certain embodiments, the surfactant used in the formulation of the invention is a polysorbate. In one embodiment, the concentration of polysorbate is about 0.1-1.5 mg/ml, about 0.2-1.4 mg/ml, about 0.3-1.3 mg/ml, about 0.4-1.2 mg/ml, about 0.5-1.1 mg/ml, about 0.6-1.0 mg/ml, about 0.6-1.1 mg/ml, about 0.7-1.1 mg/ml, about 0.8-1.1 mg/ml, or about 0.9-1.1 mg/ml. In certain embodiments, the polysorbate is at a concentration of about 0.1-10 mg/mL, about 0.5-5 mg/mL, about 0.1-2 mg/mL, or about 1 mg/mL. In one embodiment, the surfactant is polysorbate 80.

In certain embodiments, the patient is human, or a non-human mammal.

In certain embodiments, the formulation is Formulation 3 or Formulation 4 described in the Examples.

In certain embodiments, the otherwise identical formulation is the commercially available adalimumab formulation containing adalimumab, sodium chloride, monobasic sodium phosphate dihydrate, dibasic sodium phosphate dihydrate, sodium citrate, citric acid monohydrate, mannitol, polysorbate 80, and water for Injection.

In one embodiment, the otherwise identical formulation contains a buffer and a salt. In certain embodiments, the salt is a neutral salt, or a salt from a base (e.g., NaOH) used for pH adjustment. In certain embodiments, the buffer comprises a phosphate buffer and/or a citrate buffer. For example, the phosphate buffer may contain about 1.35-1.75 mg/mL or about 1.50-1.56 mg/mL of $Na_2HPO_4.2H_2O$, and about 0.75-0.95 mg/mL or about 0.83-0.89 mg/mL of $NaH_2PO_4.2H_2O$). The citrate buffer may contain about 1.15-1.45 mg/mL or about 1.30-1.31 mg/mL of citric acid.$H_2O$, and about 0.2-0.4 mg/mL or about 0.30-0.31 mg/mL of sodium citrate dehydrate. The at least one salt may be a neutral salt, such as a neutral sodium salt (e.g., NaCl).

In one embodiment, the formulation of the invention is a pharmaceutical formulation.

In certain embodiments, the formulation of the invention is suitable for subcutaneous injection. In one embodiment, the formulation of the invention is suitable for subcutaneous self-administration by a subject.

In certain embodiments, the volume of the aqueous formulation is no more than 1.5 mL, 1.0 mL, 0.8 mL, 0.5 mL, or 0.4 mL.

In certain embodiments, the formulation comprises a dose of about 30-90 mg of the antibody, or antigen binding portion thereof. In one embodiment, the formulation comprises about 40 mg of the anti-TNFα antibody, or antigen binding portion thereof. In one embodiment, the formulation comprises about 50 mg of the anti-TNFα antibody, or antigen binding portion thereof. In one embodiment, the formulation comprises about 60 mg of the anti-TNFα antibody, or antigen binding portion thereof. In one embodiment, the formulation comprises about 70 mg of the anti-TNFα antibody, or antigen binding portion thereof. In one embodiment, the formulation comprises about 80 mg of the anti-TNFα antibody, or antigen binding portion thereof. In one embodiment, the formulation comprises about 90 mg of the anti-TNFα antibody, or antigen binding portion thereof. In one embodiment, the formulation comprises 60-85 mg. In another embodiment, the formulation comprises 70-90 mg. In yet a further embodiment, the formulation contains 30-110 mg. In one embodiment, the formulation contains 70-110 mg.

Another aspect of the invention provides a pre-filled syringe or autoinjector device, comprising any of the subject formulations described herein. In certain embodiments, the aqueous formulation stored in the pre-filled syringe or autoinjector device contains about 40 mg of adalimumab, or biosimilar thereof. In certain embodiments, the aqueous formulation stored in the pre-filled syringe or autoinjector device contains about 80 mg of adalimumab, or biosimilar thereof.

Another aspect of the invention provides a method of treating a disorder associated with detrimental TNFα activity in a patient, comprising administering to the patient any one of the formulations described herein.

In one embodiment, the formulation or method of the invention is used to treat a subject having rheumatoid arthritis. In one embodiment, the formulation or method of the invention is used to treat a subject having Crohn's disease. In one embodiment, the formulation or method of the invention is used to treat a subject having psoriatic arthritis. In one embodiment, the formulation or method of the invention is used to treat a subject having psoriasis. In one embodiment, the formulation or method of the invention is used to treat a subject having juvenile idiopathic arthritis (JIA). In one embodiment, the formulation or method of the invention is used to treat a subject having ankylosing spondylitis. In one embodiment, the formulation or method of the invention is used to treat a subject having ulcerative colitis. In one embodiment, the formulation or method of the invention is used to treat a subject having hidradenitis suppurativa. In one embodiment, the formulation or method of the invention is used to treat a subject having diabetic retinopathy. In one embodiment, the formulation or method of the invention is used to treat a subject having giant cell arteritis. In one embodiment, the formulation or method of the invention is used to treat a subject having Behcet's disease. In one embodiment, the formulation or method of the invention is used to treat a subject having sarcoidosis, e.g. cutaneous sarcoidosis. In one embodiment, the formulation or method of the invention is used to treat a subject having axial spondyloarthropathy. In one embodiment, the formulation or method of the invention is used to treat a subject having uveitis.

In one embodiment, the formulation is administered to the subject according to a periodicity selected from the group consisting of weekly, biweekly, every three weeks, and monthly. In one embodiment, the formulation of the invention contains 30-90 mg of a human anti-TNFa antibody, or antigen-binding portion thereof, and is administered on a biweekly dosing regimen. In another embodiment, the formulation of the invention contains 30-90 mg of a human anti-TNFa antibody, or antigen-binding portion thereof, and is administered according to a monthly dosing regimen. In one embodiment, the formulation of the invention contains 60-85 mg of a human anti-TNFa antibody, or antigen-binding portion thereof, and is administered on a biweekly dosing regimen. In another embodiment, the formulation of the invention contains 60-85 mg of a human anti-TNFa antibody, or antigen-binding portion thereof, and is administered according to a monthly dosing regimen.

In certain embodiments, the administration of the formulation of the invention to a subject is via self-administration.

It is contemplated that any one embodiment described herein can be combined with one or more other embodiments of the invention, including embodiments described only under one aspect of the invention.

DETAILED DESCRIPTION OF THE INVENTION

I. Definitions

Figure 1:
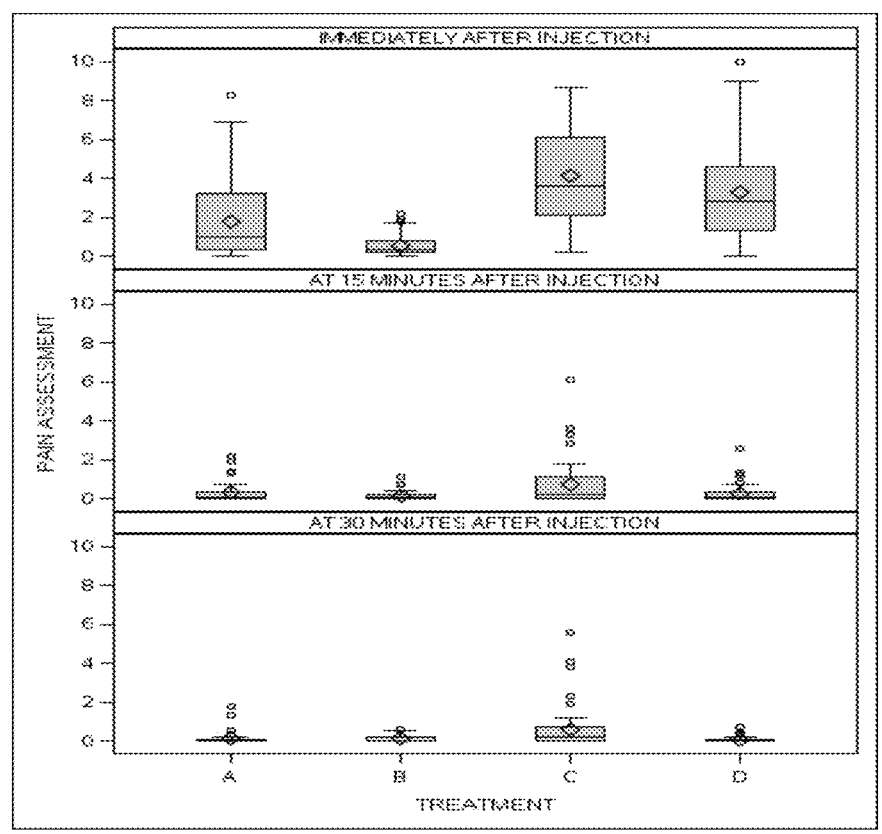
FIG. 1 is a panel of graphs that show administration of high concentration formulations 1 (F1) and 2 (F2) resulted in a significant decrease in pain assessment at all time points after injection (immediately, 15 minutes, and 30 minutes), compared to the other treatment groups (F4 and the current commercial formulation).

In order that the present invention may be more readily understood, certain terms are first defined. In addition, it should be noted that whenever a value or range of values of a parameter are recited, it is intended that values and ranges intermediate to the recited values are also intended to be part of this invention.

The term "pain associated with injection (in a patient)," as used herein, refers to the pain associated with the injection of drug into the patient's or subject's tissue. In one embodiment, the pain is separate from the pain caused by the injection device (if any), such as the injection needle stick. In one embodiment, the pain associated with injection may originate from the drug formulation being injected into patient's tissue.

The pain associated with injection may be evaluated using a number of art-recognized means, such as the Pain Visual Analog Scale (VAS). The pain measurement is, in one embodiment, quantifiable, such that a percentage pain scale reduction/increase can be directly compared using statistical methods. For example, when the Pain Visual Analog Scale is used, a numeric pain value (e.g., average±SD) can be assigned to each treatment group, such that a percentage increase or reduction can be calculated.

In general, a Visual Analogue Scale (VAS) is a measurement instrument that measures a characteristic or attitude that is believed to range across a continuum of values (see, e.g., Singer and Thods (1998) *Academic Emergency Medicine* 5:1007). For example, the amount of pain that a patient feels ranges across a continuum from none (a score of, for example, 0) to an extreme amount of pain (a score of, for example, 10). From the patient's perspective this spectrum appears continuous—their pain does not take discrete jumps, as a categorization of none, mild, moderate and severe would suggest. Operationally, a VAS is usually a horizontal line, 100 mm in length, anchored by word descriptors at each end, such as "no pain" at one end, and "extreme pain" (or some variation thereof) on the other end. The patient marks on the line at a point (for example, a score of 0-10) that they feel represents their perception of their current state. The VAS score may determined by measuring in millimeters from the left hand end of the line to the point that the patient marks.

There are various ways in which VAS have been presented, including vertical lines and lines with extra descriptors. See Wewers & Lowe ("A critical review of visual analogue scales in the measurement of clinical phenomena." *Research in Nursing and Health* 13: 227-236, 1990, incorporated by reference herein) provide an informative discussion of the benefits and shortcomings of different styles of VAS.

The term "liquid formulation" refers to a formulation in a liquid state and is not intended to refer to resuspended lyophilized formulations. A liquid formulation of the invention is stable upon storage, and does not rely upon lyophilization (or other state change methods, e.g., spray drying) for stability.

The term "liquid aqueous formulation" refers to a liquid formulation using water as a solvent. In one embodiment, a liquid aqueous formulation is a formulation that maintains stability (e.g., chemical and/or physical stability/and/or biological activity) without the need for lyophilization, spray-drying, and/or freezing.

The term "pharmaceutical," as used herein, refers to a composition, e.g., an aqueous formulation, that it is useful for treating a disease or disorder.

The term "subject" or "patient" is intended to include mammalian organisms. Examples of subjects/patients include humans and non-human mammals, e.g., non-human primates, dogs, cows, horses, pigs, sheep, goats, cats, mice, rabbits, rats, and transgenic non-human animals. In specific embodiments of the invention, the subject is a human.

The term "excipient" refers to an agent which may be added to a formulation to provide a desired characteristic, e.g., consistency, improving stability, and/or to adjust osmolality. Examples of commonly used excipients include, but are not limited to, sugars, polyols, amino acids, surfactants, and polymers.

A commonly used excipient is a polyol. As used herein, a "polyol" is a substance with multiple hydroxyl groups, and includes sugars (reducing and nonreducing sugars), sugar alcohols and sugar acids. Non-limiting examples of polyols are fructose, mannose, maltose, lactose, arabinose, xylose, ribose, rhamnose, galactose, glucose, sucrose, trehalose, sorbose, melezitose, raffinose, mannitol, xylitol, erythritol, threitol, sorbitol, glycerol, L-gluconate and metallic salts thereof. In one embodiment, the polyol used in the formulation or methods of the invention is mannitol. In one embodiment, the polyol used in the formulation or methods of the invention is sorbitol.

A "therapeutically active antibody" or "therapeutic antibody" refers to an antibody which may be used for therapeutic purposes, i.e., for the treatment of a disorder in a subject. It should be noted that while therapeutic proteins may be used for treatment purposes, the invention is not limited to such use, as said proteins may also be used for in vitro studies.

As used herein, "buffer" is an agent(s) in a solution that allows the solution to resist changes in pH by the action of its acid-base conjugate components. Examples of buffers include acetate (e.g. sodium acetate), succinate (such as sodium succinate), gluconate, histidine, methionine, citrate, phosphate, citrate/phosphate, imidazole, combinations thereof, and other organic acid buffers. In one embodiment, a buffer is not a protein. A buffer may provide a solution with a pH in the range from about 4 to about 8; from about 4.5 to about 7; or from about 5.0 to about 6.5.

Although the formulations of the invention do not contain a buffer(s), otherwise identical formulations containing one or more buffers may be used for pain or bioavailability comparison purposes. Examples of such buffers include phosphate, acetate (e.g., sodium acetate), succinate (such as sodium succinate), gluconate, glutamate, histidine, citrate and other organic acid buffers. In one embodiment, a representative buffer in the otherwise identical formulation comprises a citrate buffer and/or a phosphate buffer.

As used herein, the term "surfactant" generally includes an agent that protects the protein, e.g., antibody, from air/solution interface-induced stresses, solution/surface induced-stresses, to reduce aggregation of the antibody, or to minimize the formation of particulates in the formulation. Exemplary surfactants include, but are not limited to, nonionic surfactants such as polysorbates (e.g. polysorbates 20 and 80) or poloxamers (e.g. poloxamer 188). The term "surfactant" or "detergent" includes nonionic surfactants such as, but not limited to, polysorbates. In one embodiment, a surfactant includes poloxamers, e.g., Poloxamer 188, Poloxamer 407; polyoxyethylene alkyl ethers, e.g., Brij 35®, Cremophor A25, Sympatens ALM/230; and polysorbates/Tweens, e.g., Polysorbate 20 (Tween 20), Polysorbate 80 (Tween 80), Mirj, and Poloxamers, e.g., Poloxamer 188.

A "stable" formulation is one in which the antibody therein essentially retains its physical stability and/or chemical stability and/or biological activity during the manufacturing process and/or upon storage. Various analytical techniques for measuring protein stability are available in the art and are reviewed in *Peptide and Protein Drug Delivery* 247-301, Vincent Lee Ed., Marcel Dekker, Inc., New York, N.Y., Pubs. (1991); and Jones, A. (1993) *Adv. Drug Delivery Rev.* 10: 29-90 (both incorporated by reference). For example, in one embodiment, the stability of a protein is determined according to the percentage of monomer protein in the solution, with a low percentage of degraded (e.g., fragmented) and/or aggregated protein. In one embodiment, the formulation may be stable at room temperature, at about 25-30° C., or at 40° C. for at least 1 month and/or stable at about 2-8° C. for at least 1 month, 1 year, or, alternatively, for at least 2 years. In another embodiment, the formulation may be stable up to about 30 degrees C. for at least about 6 days, about 10, days, or about 14 days, or is stable at about 28 degrees C. for up to about 24 months. In one embodiment, the formulation may be stable following freezing (to, e.g., −70° C.) and thawing of the formulation, hereinafter referred to as a "freeze/thaw cycle."

An antibody "retains its physical stability" in a pharmaceutical formulation if it shows substantially no signs of, e.g., aggregation, precipitation and/or denaturation upon visual examination of color and/or clarity, or as measured by UV light scattering or by size exclusion chromatography. Aggregation is a process whereby individual molecules or complexes associate covalently or non-covalently to form aggregates. Aggregation can proceed to the extent that a visible precipitate is formed.

Stability, such as physical stability of a formulation, may be assessed by methods well-known in the art, including measurement of a sample's apparent attenuation of light (absorbance, or optical density). Such a measurement of light attenuation relates to the turbidity of a formulation. The turbidity of a formulation is partially an intrinsic property of the protein dissolved in solution and is commonly determined by nephelometry, and measured in Nephelometric Turbidity Units (NTU).

The degree of turbidity, e.g., as a function of the concentration of one or more of the components in the solution, e.g., protein and/or salt concentration, is also referred to as the "opalescence" or "opalescent appearance" of a formulation. The degree of turbidity can be calculated by reference to a standard curve generated using suspensions of known turbidity. Reference standards for determining the degree of turbidity for pharmaceutical compositions can be based on the European Pharmacopeia criteria (European Pharmacopoeia, Fourth Ed., Directorate for the Quality of Medicine of the Council of Europe (EDQM), Strasbourg, France). According to the European Pharmacopeia criteria, a clear solution is defined as one with a turbidity less than or equal to a reference suspension which has a turbidity of approximately 3 according to European Pharmacopeia standards. Nephelometric turbidity measurements can detect Rayleigh scatter, which typically changes linearly with concentration, in the absence of association or nonideality effects. Other methods for assessing physical stability are well-known in the art.

An antibody "retains its chemical stability" in a pharmaceutical formulation, if the chemical stability at a given time is such that the antibody is considered to still retain its biological activity as defined below. Chemical stability can be assessed by, e.g., detecting and quantifying chemically altered forms of the antibody. Chemical alteration may involve size modification (e.g. clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation or oxidation) which can be evaluated by ion-exchange chromatography, for example.

An antibody "retains its biological activity" in a pharmaceutical formulation, if the antibody in a pharmaceutical formulation is biologically active for its intended purpose. For example, biological activity is retained if the biological activity of the antibody in the pharmaceutical formulation is within about 30%, about 20%, or about 10% (within the errors of the assay) of the biological activity exhibited at the time the pharmaceutical formulation was prepared (e.g., as determined in an antigen binding assay).

In a pharmacological sense, in the context of the present invention, a "therapeutically effective amount" or "effective amount" of an antibody refers to an amount effective in the prevention or treatment or alleviation of a symptom of a disorder for the treatment of which the antibody is effective.

The term "human TNF-alpha" (abbreviated herein as hTNF-alpha, TNFα, or simply hTNF), as used herein, is intended to refer to a human cytokine that exists as a 17 kDa secreted form and a 26 kDa membrane associated form, the biologically active form of which is composed of a trimer of noncovalently bound 17 kDa molecules. The structure of hTNF-alpha is described further in, for example, Pennica, D., et al. (1984) Nature 312:724-729; Davis, J. M., et al. (1987) Biochem 26:1322-1326; and Jones, E. Y., et al. (1989) Nature 338:225-228. The term human TNF-alpha is intended to include recombinant human TNF-alpha (rhTNF-alpha), which can be prepared by standard recombinant expression methods or purchased commercially (R & D Systems, Catalog No. 210-TA, Minneapolis, Minn.).

The term "antibody," as used herein, is intended to refer to immunoglobulin molecules comprised of four polypeptide chains, two heavy (H) chains and two light (L) chains interconnected by disulfide bonds. Other naturally occurring antibodies of altered structure, such as, for example, camelid antibodies, are also included in this definition. Each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In one embodiment of the invention, the formulation contains an antibody with CDR1, CDR2, and CDR3 sequences like those described in U.S. Pat. Nos. 6,090,382 and 6,258,562, each incorporated by reference herein. In certain embodiments, the formulation contains an antibody as claimed in U.S. Pat. Nos. 6,090,382 and 6,258,562.

As used herein, the term "CDR" refers to the complementarity determining region within a antibody variable sequence. There are three CDRs in each of the variable regions of the heavy chain and the light chain, which are designated CDR1, CDR2 and CDR3, for each of the heavy and light chain variable regions. The exact boundaries of these CDRs have been defined differently according to different systems. The system described by Kabat (Id.) not only provides an unambiguous residue numbering system applicable to any variable region of an antibody, but also provides precise residue boundaries defining the three CDRs. These CDRs may be referred to as Kabat CDRs. Chothia et al. found that certain sub-portions within Kabat CDRs adopt nearly identical peptide backbone conformations, despite having great diversity at the level of amino acid sequence (Chothia et al. (1987) Mol. Biol. 196:901-917; Chothia et al. (1989) Nature 342:877-883) These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (1995) FASEB J. 9:133-139 and MacCallum (1996) J. Mol. Biol. 262(5):732-45. Still other CDR boundary definitions may not strictly follow one of the herein described systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat or Chothia defined CDRs. In one embodiment, the antibody used in the methods and compositions of the invention includes the six CDRs from the antibody adalimumab.

The term "antigen-binding portion" of an antibody (or simply "antibody portion"), as used herein, refers to one or more fragments of an antibody that retain the ability to specifically bind to an antigen (e.g., hTNF-alpha). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) Proc. Natl. Acad. Sci. USA 90:6444-6448; Poljak, R. J., et al. (1994) Structure 2:1121-1123). In one embodiment of the invention, the formulation contains an antigen-binding portions described in U.S. Pat. Nos. 6,090, 382 and 6,258,562, each incorporated by reference herein.

The phrase "recombinant antibody" refers to antibodies that are prepared, expressed, created or isolated by recombinant means, such as antibodies expressed using a recombinant expression vector transfected into a host cell, antibodies isolated from a recombinant, combinatorial antibody library, antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of particular immunoglobulin gene sequences (such as human immunoglobulin gene sequences) to other DNA sequences. Examples of recombinant antibodies include recombinant human, chimeric, CDR-grafted and humanized antibodies.

The term "human antibody," as used herein, is intended to include antibodies having variable and constant regions derived from human germline immunoglobulin sequences. The human antibodies used in the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody," as used herein, is not intended to include antibodies in which CDR sequences derived from the germline of another mammalian species, such as a mouse, have been grafted onto human framework sequences.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

An "isolated antibody," as used herein, is intended to refer to an antibody that is substantially free of other antibodies having different antigenic specificities (e.g., an isolated antibody that specifically binds hTNF-alpha is substantially free of antibodies that specifically bind antigens other than hTNF-alpha). An isolated antibody that specifically binds hTNF-alpha may, however, have cross-reactivity to other antigens, such as TNF-alpha molecules from other species. Moreover, an isolated antibody may be substantially free of other cellular material and/or chemicals.

A "neutralizing antibody," as used herein (or an "antibody that neutralized hTNF-alpha activity"), is intended to refer to an antibody whose binding to hTNF-alpha results in inhibition of the biological activity of hTNF-alpha. This inhibition of the biological activity of hTNF-alpha can be assessed by measuring one or more indicators of hTNF-alpha biological activity, such as hTNF-alpha-induced cytotoxicity (either in vitro or in vivo), hTNF-alpha-induced cellular activation and hTNF-alpha binding to hTNF-alpha receptors. These indicators of hTNF-alpha biological activity can be assessed by one or more of several standard in vitro or in vivo assays known in the art, and described in U.S. Pat. Nos. 6,090,382 and 6,258,562, each incorporated by reference herein. In one embodiment, the ability of an antibody to neutralize hTNF-alpha activity is assessed by inhibition of hTNF-alpha-induced cytotoxicity of L929 cells. As an additional or alternative parameter of hTNF-alpha activity, the ability of an antibody to inhibit hTNF-alpha-induced expression of ELAM-1 on HUVEC, as a measure of hTNF-alpha-induced cellular activation, can be assessed.

The term "surface plasmon resonance," as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jonsson, U., et al. (1993) Ann. Biol. Clin. 51:19-26; Jonsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$k_{on}$" as used herein, is intended to refer to the on rate constant for association of a binding protein (e.g., an antibody) to the antigen to form the, e.g., antibody/antigen complex as is known in the art.

The term "$k_{off}$" as used herein, is intended to refer to the off rate constant for dissociation of an antibody from the antibody/antigen complex.

The term "$K_d$," as used herein, is intended to refer to the dissociation constant of a particular antibody-antigen interaction and refers to the value obtained in a titration measurement at equilibrium, or by dividing the dissociation rate constant ($k_{off}$) by the association rate constant ($k_{on}$).

As used herein, "biosimilar" (of an approved reference product/biological drug, such as a protein therapeutic, antibody, etc.) refers to a biologic product that is similar to the reference product based upon data derived from (a) analytical studies that demonstrate that the biological product is highly similar to the reference product notwithstanding minor differences in clinically inactive components; (b) animal studies (including the assessment of toxicity); and/or (c) a clinical study or studies (including the assessment of immunogenicity and pharmacokinetics or pharmacodynamics) that are sufficient to demonstrate safety, purity, and potency in one or more appropriate conditions of use for which the reference product is licensed and intended to be used and for which licensure is sought for the biological product. In one embodiment, the biosimilar biological product and reference product utilize the same mechanism or mechanisms of action for the condition or conditions of use prescribed, recommended, or suggested in the proposed labeling, but only to the extent the mechanism or mechanisms of action are known for the reference product. In one embodiment, the condition or conditions of use prescribed, recommended, or suggested in the labeling proposed for the biological product have been previously approved for the reference product. In one embodiment, the route of administration, the dosage form, and/or the strength of the biological product are the same as those of the reference product. In one embodiment, the facility in which the biological product is manufactured, processed, packed, or held meets standards designed to assure that the biological product continues to be safe, pure, and potent. The reference product may be approved in at least one of the U.S., Europe, or Japan.

The term "dosing", as used herein, refers to the administration of a substance (e.g., an anti-TNFa antibody) to achieve a therapeutic objective (e.g., the treatment of a TNFa-associated disorder).

The terms "weekly dosing regimen", "weekly dosing" and "weekly administration" as used herein, refer to a certain time course (or periodicity) of administering a substance (e.g., an anti-TNFα antibody) to a subject to achieve a therapeutic objective (e.g., the treatment of a TNFα.-associated disorder). In one embodiment, the antibody, or antigen-binding portion thereof, is administered every 6-8 days, or, alternatively, every 7 days.

The terms "biweekly dosing regimen", "biweekly dosing", and "biweekly administration", as used herein, refer to a certain time course (or periodicity) of administering a substance (e.g., an anti-TNFα antibody) to a subject to achieve a therapeutic objective (e.g., the treatment of a TNFα.-associated disorder). The biweekly dosing regimen is not intended to include a weekly dosing regimen. In one embodiment, the antibody, or antigen-binding portion thereof, is administered every 9-19 days, more preferably, every 11-17 days, even more preferably, every 13-15 days, and most preferably, every 14 days.

The terms "monthly dosing regimen", "monthly dosing", and "monthly administration", as used herein, refer to a certain time course (or periodicity) of administering a substance (e.g., an anti-TNFα antibody) to a subject to achieve a therapeutic objective (e.g., the treatment of a TNFα.-associated disorder). In one embodiment, a monthly dosing regimen means that the antibody, or antigen-binding portion thereof, is administered every 28-31 days. In another embodiment, a monthly dosing regimen means that the antibody, or antigen-binding portion thereof, is administered once a month, e.g. on the same day each month, such as, for example, the first day of each month.

AUC, Cmax, and Tmax are pharmacokinetic parameters that may be used to characterize the pharmacokinetic responses of a particular drug product in an animal or human subject. The term "AUC" refers to the "area under the curve" that represents changes in blood, serum, or plasma concentrations of a substance, e.g., a human anti-TNFα antibody, over time. As used herein, the term "Cmax" refers to the maximum or peak blood, serum, or plasma concentration of substance observed in a subject after its administration. The term "Tmax" refers to the time at which the Cmax occurred, as measured from the time point of administration."

The term "hydrodynamic diameter" or "$D_h$" of a particle refers to the diameter of a sphere that has the density of water and the same velocity as the particle. Thus, the term "hydrodynamic diameter of an antibody" as used herein refers to a size determination for an antibody, or an antigen-binding portion thereof, e.g., a human anti-TNFα antibody, or antigen-binding fragment thereof, in solution using dynamic light scattering (DLS). A DLS-measuring instrument measures the time-dependent fluctuation in the intensity of light scattered from the antibody, or antigen-binding fragment thereof, in solution at a fixed scattering angle. $D_h$ is determined from the intensity autocorrelation function of the time-dependent fluctuation in intensity. Scattering intensity data are processed using DLS instrument software to determine the value for the hydrodynamic diameter and the size distribution of the scattering molecules, e.g. the human anti-TNFα antibody, or antigen-binding fragment thereof, specimen.

The term "conductivity," as used herein, refers to the ability of an aqueous solution to conduct an electric current between two electrodes. Generally, electrical conductivity or specific conductivity is a measure of a material's ability to conduct an electric current. In solution, the current flows by ion transport. Therefore, with an increasing amount of ions present in the aqueous solution, the solution will have a higher conductivity. The unit of measurement for conductivity is mmhos (mS/cm), and can be measured using a conductivity meter sold, e.g., by Orion Research, Inc. (Beverly, Mass.). The conductivity of a solution may be altered by changing the concentration of ions therein. For example, the concentration of buffer and/or salt, in the solution may be altered in order to achieve the desired conductivity.

Conductivity of a solution is measured according to methods known in the art. Conductivity meters and cells may be used to determine the conductivity of the aqueous formulation, and should be calibrated to a standard solution before use. Examples of conductivity meters available in the art include MYRON L Digital (Cole Parmer®), Conductometer (Metrohm AG), and Series 3105/3115 Integrated Conductivity Analyzers (Kemotron).

Conductivity measurements may be taken with any commercially available conductivity meter suitable for conductivity analysis in protein solutions, e.g. conductivity meter Model SevenMulti, with expansion capacity for broad pH range (Mettler Toledo, Schwerzenbach, Switzerland). The instrument is operated according to the manufacturers instructions (e.g., if the conductivity sensor is changed in the Mettler Toledo instrument, calibration must be performed again, as each sensor has a different cell constant; refer to Operating Instructions of Model SevenMulti conductivity meter). If the instructions are followed, conductivity measurements can be taken by directly immersing the measuring probe into the sample solution.

Various aspects of the invention are described in further detail in the following subsections.

II. Formulations and Methods of the Invention

The present invention features stable, liquid aqueous pharmaceutical formulations comprising an anti-TNFα antibody, or an antigen binding portion thereof, having improved properties as compared to art-recognized formulations. While high concentration formulations containing human anti-TNFα antibodies are known in the art (see, for example, US20060153846 and US20100278822), the instant invention provides high concentration formulations having unexpected characteristics, i.e., significantly decreased pain or increased bioavailability. The formulations of the invention are based, at least in part, on the combination of only one or two excipients, i.e., a surfactant and a polyol or, alternatively, a surfactant alone. Despite having few excipients, the formulations of the invention contain a high concentration of an antibody, e.g. 90-110 mg/ml, and are stable.

As described in the working examples below, a formulation containing an antibody concentration of more than 50 mg/ml of an isolated human anti-TNFα antibody, less than 50 mg/ml of a polyol, (such as mannitol), and a surfactant, (such as a polysorbate), was shown to have dramatically reduced pain upon injection relative to other high concentration formulations, including the commercial adalimumab formulation described in US20060153846, and the formulation described in US20100278822, each of which is incorporated by reference herein. Thus, in one embodiment, the formulations of the invention are associated with a reduction of pain, despite having a high antibody concentration (e.g., 100 mg/mL) and having no buffer or salt. The low-pain formulations described herein are based, at least in part, on the surprising finding that by removing or excluding salt (e.g., NaCl) and/or a buffer (e.g., a phosphate/citrate buffer) the concentration of a human anti-TNF alpha antibody in a formulation can be increased, e.g., to about 100 mg/mL, while decreasing pain upon delivery to a patient.

In one embodiment, the formulation of the invention is surprising, in that the formulation does not contain a buffer or a salt, and reduces pain associated with injection in a patient by at least about 50% when compared to injecting an otherwise identical formulation comprising at least one salt and/or at least one buffer. In one embodiment, the formulation reduces pain associated with the injection in a human subject by at least about 30%, 35%, 40%, 45%, 50%, 55%, 60%, 65%, 70%, 75%, or 80% (e.g., about 25, 26, 27, 28, 29, 30, 31, 32, 33, 34, 35, 36, 37, 38, 39, 50, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80%) when compared to the injection of an otherwise identical formulation that further comprises a salt and/or a buffer.

In one embodiment, the otherwise identical formulation used for pain comparison assay comprises at least one buffer, such as a citrate buffer and a phosphate buffer, and/or a salt, e.g., NaCl. For example, the buffer (excluded from the formulation of the invention and present in the reference formulation for pain comparisons) may include citric acid monohydrate, sodium citrate, disodium phosphate dihydrate, and/or sodium dihydrogen phosphate dihydrate. The buffer may include about 1.15-1.45 mg/ml of citric acid (e.g., about 1.15, 1.20, 1.25, 1.30, 1.35, 1.40, or 1.45), about 0.2-0.4 mg/mL of sodium citrate dehydrate (e.g., about 0.2, 0.25, 0.3, 0.35, or 0.4), about 1.35-1.75 mg/mL of disodium phosphate dehydrate (e.g., about 1.35, 1.40, 1.45, 1.50, 1.55, 1.60, 1.65, 1.70, or 1.75), about 0.75-0.95 mg/mL of sodium dihydrogen phosphate dehydrate (e.g., about 0.75, 0.80, 0.85, 0.9, or 0.95). Values and ranges intermediate to the aforementioned concentrations are also intended to be part of this invention. In addition, ranges of values using a combination of any of the above-recited values as upper and/or lower limits are intended to be included, e.g., 0.1 to 0.5 mg/mL or 1.20-1.40 mg/mL. In one embodiment, the pH of the formulation is adjusted with sodium hydroxide.

In one embodiment, the formulation of the invention includes high concentrations of human anti-TNFa antibodies, or antigen binding portions thereof, e.g., 90-110 mg/ml, a polyol at a concentration less than 50 mg/ml, and a surfactant, such that the formulation is suitable for administration without significant pain as determined by a visual analog scale (VAS) score. In one embodiment, the formulation and methods of the invention include high concentrations of anti-TNFα antibodies, or antigen binding portions thereof, and no buffer or salt, such that they are suitable for, administration, e.g., subcutaneous administration, without significant felt pain as determined by a visual analog scale (VAS) score. For example, the formulation of the invention may result in a VAS score of less than 1 on a scale of 0 (no pain) to 10 (worst imaginable pain) following subcutaneous injection. As described in Example 1, a formulation having 100 mg/ml of adalimumab, polysorbate 80, and mannitol (less than 50 mg/ml) resulted in a VAS score of less than 1, e.g., 0.56, whereas other high antibody concentration formulations resulted in VAS scores ranging from 1.79 to 4.12.

In one embodiment, the invention provides a liquid aqueous formulation comprising an isolated human anti-TNFα antibody, or an antigen-binding portion thereof, a surfactant, and less than 50 mg/ml of a polyol, wherein subcutaneous injection of the formulation results in a Pain Visual Analog Scale score of less than 1.0 following injection. In one embodiment, the formulation does not contain a buffer and a salt, and results in a reduction of pain of at least about 50% upon subcutaneous injection when compared to an injection of an otherwise identical formulation that further comprises a salt and/or a buffer(s).

Thus, in one aspect of the invention, liquid formulations of the invention have advantageous tolerability properties in that the formulations produce less pain relative to formulations containing a buffer and a salt. In certain embodiments, the formulation reduces pain associated with injection (or any other form of administration) in a subject. In some embodiments, pain associated with injection is reduced by at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% (e.g., at least about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65 66, 67, 68, 69, 70, 71, 72, 73, 74, 75, 76, 77, 78, 79, 80, 81, 82, 83, 84, 85, 86, 87, 88, 89, 90, 91, 92, 93, 94, or 95%). In one embodiment, pain is reduced by at least about 50%.

Pain may be evaluated using any type of pain assessment known in the art, including, for example, visual analog scales, qualitative assessments of pain, or needle pain assessments. For example, subject-perceived injection site pain may be assessed using the Pain Visual Analog Scale (VAS). A VAS is a measurement instrument that measures pain as it ranges across a continuum of values, e.g., from none to an extreme amount of pain. Operationally a VAS is a horizontal line, about 100 mm in length, anchored by numerical and/or word descriptors, e.g., 0 or 10, or "no pain" or "excruciating pain," optionally with additional word or numeric descriptors between the extremes, e.g., mild, moderate, and severe; or 1 through 9) (see, e.g., Lee J S, et al. (2000) Acad Emerg Med 7:550, or Singer and Thods (1998) *Academic Emergency Medicine* 5:1007). Pain may be assessed at a single time or at various times following administration of a formulation of the invention such as, for example, immediately after injection, at about 1, 2, 3, 4, 5, 6, 7, 8, 9, 10, 15, 20, 25, 30, 35, 40, or 45 minutes after injection.

In a certain embodiment of the invention, injection of the formulation into a subject results in a Pain Visual Analog Scale score of less than 0.6, 0.7, 0.8, 0.9, 1.0, 2.0, 3.0, 4.0, or 5.0 on a scale of 0 (no pain) to 10 (excruciating pain).

Other tools for pain assessment are known in the art, including, for example, the Numerical Rating Scale, the Verbal Rating Scale, and the Brief Pain Inventory. Such tools could also be used to assess pain in accordance with the invention.

Additional indices for skin irritation may be used, including, e.g., the Draize Scale (hemorrhage, petechiae, erythema, edema, pruritus).

Formulations of the invention containing a polyol preferably contain less than about 50 mg of the polyol. In one embodiment, the formulations contain less than about 45 mg/mL of the polyol. In another embodiment, the formulations of the invention contain about 38-46 mg/mL of the polyol (e.g., mannitol), e.g., about 35, 36, 37, 38, 39, 40, 41, 42, 43, 44, 45, 46, 47, 48, 49, 50, 51, 52, 53, 54, or 55 mg/mL of the polyol. In addition, ranges of values using a combination of any of the above recited values as upper and/or lower limits are intended to be included, e.g., 39-45 mg/ml, 40-44 mg/ml, or 37-47 mg/ml. In one embodiment, the formulations of the invention contain about 12-72 mg/ml of polyol, e.g., mannitol. In one embodiment, suitable polyols for use in the formulations and methods of the invention are mannitol or sorbitol.

In one embodiment, the formulation of the invention contains adalimumab (or a biosimilar thereof), polysorbate 80, mannitol, and water for injection. In one embodiment, the formulation contains 80 mg of adalimumab, water for injection, 42 mg/ml of mannitol, and 1 mg/ml of polysorbate 80. In one embodiment, the formulation may contain 20-110 mg, alternatively 20-90 mg of adalimumab or, alternatively, 30-80 mg of the antibody. In one embodiment, the formulation contains 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, or 110 mg of the antibody. Ranges including the aforementioned numbers are also included in the invention, e.g., 70-90 mg, 65-95, or 60-85 mg.

The present invention is also based, at least in part on the surprising discovery that a liquid aqueous pharmaceutical formulation having a high concentration of a human anti-TNFα antibody, or antigen binding portion thereof, and a surfactant (i.e., in the absence of additional excipients), has greater bioavailability than other high concentration formulations having additional excipients. As described in the working examples below, a formulation containing more than 50 mg/ml of an isolated human anti-TNFα antibody, and a polysorbate was shown to have increased bioavailability relative to other high concentration formulations, including the commercial adalimumab formulation described in US20060153846.

As described in Example 2 below, bioavailability of an anti-TNFa antibody can be increased by combining the antibody with a surfactant, e.g., polysorbate 80. The increase in bioavailability is based on the combination of the antibody and surfactant and the omission or removal of other excipients, including a buffer, polyol, and salt. The increase in bioavailability results in an $AUC_{0-360}$ of the anti-TNFα antibody, or an antigen-binding portion thereof, of greater than about 1300 μg*hr/ml or an $AUC_{0-1344}$ of the anti-TNFα antibody, or an antigen-binding portion thereof, of greater than about 2600 μg*hr/ml, when subcutaneously injected into a human subject.

Accordingly, the present invention provides methods for improving the bioavailability of an isolated anti-TNFα antibody, or an antigen-binding portion thereof, in a pharmaceutical formulation. The methods include combining a therapeutically effective amount of the anti-TNFa antibody, or antigen-binding portion thereof, with a surfactant and excluding or removing other excipients, e.g., a buffer(s), salt, and polyol, or combinations thereof, such that the bioavailability of the antibody, or antigen-binding portion thereof, is improved. In one embodiment, the formulation is injected subcutaneously into a human subject. The methods may improve the bioavailability by providing an $AUC_{0-360}$ of the anti-TNFα antibody, or an antigen-binding portion thereof, of greater than about 1100, 1125, 1150, 1175, 1200, 1225, 1250, 1275, 1300, 1325, 1350, 1375, 1400, 1425, 1450, 1475, or about 1500 μg*hr/ml when subcutaneously injected into a human subject.

The invention further provides a method of improving the bioavailability of an isolated human anti-TNFα antibody, or an antigen-binding portion thereof, in a subject, said method comprising administering a formulation comprising a surfactant and an effective amount of the antibody, or antigen-binding portion thereof, to the subject such that the bioavailability of the antibody, or antigen-binding portion thereof, in the subject is improved at least about 15% over a second formulation. In one embodiment, the formulation of the invention does not contain a buffer, a polyol, or a salt, and the second formulation comprises a buffer, a polyol, and a salt. In one embodiment, the bioavailability of the antibody, or antigen-binding portion thereof, is improved at least about 30% over the second formulation. In one embodiment, the bioavailability of the antibody, or antigen-binding portion thereof, is improved at least about 40% over the second formulation. In one embodiment, the bioavailability may be determined according to either an AUC level, e.g., $AUC_{0-360}$ or an $AUC_{0-1344}$, or a Cmax.

In one embodiment, the present invention provides a liquid aqueous formulation which includes a surfactant and about 30-90 mg of an isolated human anti-TNFα antibody or antigen-binding portion, wherein the formulation has an antibody concentration of about 90-110 mg/ml, and wherein the formulation provides increased bioavailability of the antibody, or antigen-binding portion thereof, to a human subject upon subcutaneous injection of the formulation relative to a formulation comprising citrate phosphate buffer, sodium chloride, and mannitol.

In one embodiment, the present invention provides liquid aqueous formulations which include a surfactant and 30-90 mg of an isolated human anti-TNFα antibody, or an antigen-binding portion, wherein the formulation has an antibody concentration of 90-110 mg/ml, and wherein the formulation provides increased bioavailability of the antibody, or antigen-binding portion thereof, to a human subject upon subcutaneous injection of the formulation, such that the antibody or antigen-binding portion thereof, has an $AUC_{0-360}$ greater than about 1100, 1125, 1150, 1175, 1200, 1225, 1250, 1275, 1300, 1325, 1350, 1375, 1400, 1425, 1450, 1475, or about 1500 μg*hr/ml.

In one embodiment, the formulation of the invention contains adalimumab (or a biosimilar thereof), polysorbate 80, and water for injection. In one embodiment, the formulation contains 80 mg of adalimumab, water for injection, and 1 mg/ml polysorbate 80. The formulation may contain 20-110 mg, alternatively 20-90 mg of adalimumab or, alternatively, 30-80 mg of the antibody. In one embodiment, the formulation contains 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, or 110 mg of the antibody. Ranges including the aforementioned numbers are also included in the invention, e.g., 70-90 mg, 65-95 mg, or 60-85 mg.

Thus, the high antibody formulations and methods of the invention not only overcome a number of known challenges for pharmaceutical formulations, including high concentrations in a stable formulation, but also possesses the added benefit of producing improved bioavailability or providing significantly low levels of pain when injected into patients.

Another obstacle overcome by the formulations of the invention is the ability to remain stable at room temperature (at about 25 degree C. or up to about 30 degrees C.). Such stability provides advantages for the user of the antibody, providing for more flexible storage options, as the constant need for refrigeration is unnecessary. Both the decreased pain formulation and the increased bioavailability formulation (exemplified by formulations F3 and F4, respectively, in the Examples below) are stable for at least 6 days at about 25 degrees C. or up to about 30 degrees C. As described in more detail in the Examples, the formulations of the invention are stable at up to 30 degrees C. for at least 6 days, at least 7 days, at least 8 days, at least 9 days, at least 10 days, at least 11 days, at least 12 days, at least 13 days, and at least 14 days. Thus, the invention further provides formulations having extended (i.e., at least 6 days, 10 days or 14 days) shelf life at room temperature (or about 25 degrees C. or up to about 30 degrees C.). In one embodiment, the formulation of the invention is stable at 20 to 32 degrees C. for at least 6 days. Temperatures intermediate to the above recited concentrations are also intended to be part of this invention, i.e., 20, 21, 22, 23, 24, 25, 26, 27, 28, 29, 30, 31 and 32 degrees Celsius (C). Ranges including the aforementioned temperatures are also included in the invention, e.g., 22-26 degrees C., 25-30 degrees C., etc.

The formulations of the invention contain a high antibody concentration, including, for example, an antibody concentration of about 50 mg/mL, 55 mg/mL, 60 mg/mL. 65 mg/mL, 70 mg/mL, 75 mg/ml, 80 mg/mL, 85 mg/mL, 90 mg/mL, 95 mg/mL 100 mg/mL, 105 mg/mL, 110 mg/mL, 115 mg/mL (or higher) of a human anti-TNF-alpha antibody or antigen-binding fragment thereof. Accordingly, as described in the examples below, in one aspect of the invention the liquid pharmaceutical formulations of the invention contain a human anti-TNF alpha antibody concentration of 50-100 mg/mL or greater. In one embodiment, the formulations of the invention may comprise an antibody concentration between about 1 mg/mL-150 mg/mL or about 40 mg/mL-125 mg/mL. In one embodiment, the antibody concentration of the formulation is 50-150 mg/ml, 55-150 mg/ml, 60-150 mg/ml, 65-150 mg/ml, 70-150 mg/ml, 75-150 mg/ml, 80-150 mg/ml, 85-150 mg/ml, 90-150 mg/ml, 90-110 mg/ml, 95-105 mg/ml, 95-150 mg/ml, 100-150 mg/ml, 105-150 mg/ml, 110-150 mg/ml, 115-150 mg/ml, 120-150 mg/ml, 125-150 mg/ml, 50-130 mg/ml, 75-125 mg/ml, etc. Concentrations and ranges intermediate to the above recited concentrations are also intended to be part of this invention (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150 mg/mL).

The formulations of the invention may contain an effective amount of the antibody. In one embodiment, an effective amount is about 20, 25, 30, 35, 40, 45, 50, 55, 60, 65, 70, 75, 80, 85, 90, 95, or about 100 mg of the human anti-TNFα antibody, or antigen-binding portion thereof. In one embodiment, the formulations and methods of the invention comprise about 20-100, about 20-90, about 30-90, about 30-100, about 60-100, about 70-90, about 40-90, about 60-85 mg, or about 40-100 mg of a human anti-TNFα antibody, or antigenbinding portion thereof. In one embodiment, the formulation contains 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, or 90 mg of the antibody. Ranges including the aforementioned numbers are also included in the invention, e.g., 70-90 or 75-85 mg or 60-85 mg.

An important aspect of the formulations and methods of the invention is the omission of a buffer and salt. Thus, in one embodiment, the formulations and methods of the invention do not contain any buffer(s) (e.g., citrate and phosphate) and salts. It should be noted, however, that although the preferred formulations of the invention do not contain buffers or salts (e.g., NaCl), a small amount of buffer and/or salt may be present in the formulations. Thus, in one embodiment, the formulations of the invention do not contain detectable levels of a buffer(s) and/or a salt.

In one embodiment, the buffer(s) omitted from the formulations of the invention (or those formulations for comparison which include a buffer(s)) may include citric acid (e.g., about 1.3-1.31 mg/mL or 1.305 mg/mL). In another embodiment, the buffer system includes sodium citrate dehydrate (e.g., about 0.27-0.33 mg/mL or about 0.305 mg/mL). In one embodiment, the buffer system includes disodium phosphate dehydrate (e.g., about 1.5-1.56 mg/mL or about 1.53 mg/mL). In another embodiment, the buffer system includes sodium dihydrogen phosphate dihydrate (e.g., about 0.83-0.89 mg/mL or about 0.86 mg/mL).

In one embodiment of the invention, the conductivity of the formulation may be used to determine if a formulation has a buffer and/or salt. Both Formulation F3 and F4 (described in the working examples below) have been determined to have a conductivity of less than about 2 mS/cm, e.g., about 0.70 µS/cm. Thus, in one embodiment, the reduced pain and increased bioavailability formulations of the invention have a conductivity of less than about 2 mS/cm. In another embodiment, the formulations of the invention have a conductivity of less than about 1 mS/cm.

In one embodiment, the formulation of the invention contains of a human anti-TNF alpha antibody, or antigen binding portion thereof, at a concentration of about 100 mg/mL (or 75-125 mg/mL), a surfactant (e.g., polysorbate 80), a polyol (e.g., sorbitol or mannitol), and has a conductivity of less than 2 mS/cm. In one embodiment, the formulation of the invention contains of a human anti-TNF alpha antibody, or antigen binding portion thereof, at a concentration of about 100 mg/mL (or 75-125 mg/mL), about 0.8-1.3 mg/ml of a surfactant (e.g., polysorbate 80), less than about 50 mg/ml of a polyol (e.g., sorbitol or mannitol), and has a conductivity of less than 2 mS/cm.

In one embodiment, the formulation of the invention contains of a human anti-TNF alpha antibody, or antigen binding portion thereof, at a concentration of about 100 mg/mL (or 75-125 mg/mL), a surfactant (e.g., polysorbate 80), and has a conductivity of less than 2 mS/cm. In one embodiment, the formulation of the invention contains of a human anti-TNF alpha antibody, or antigen binding portion thereof, at a concentration of about 100 mg/mL (or 75-125 mg/mL), about 0.8-1.3 mg/ml of a surfactant (e.g., polysorbate 80), and has a conductivity of less than 2 mS/cm.

In another embodiment, the invention provides a stable formulation having a high concentration antibody, or antigen-binding portion thereof, wherein the antibody, or antigen has a hydrodynamic diameter (z-average) of less than about 4 nm or wherein the antibody, or antigen has a hydrodynamic diameter (z-average) which is at least about 50% less than the hydrodynamic diameter of a buffered solution at the same antibody concentration. In one embodiment, the antibody, or antigen has a hydrodynamic diameter (z-average) of less than about 3 nm.

In one embodiment, the formulation of the invention contains of a human anti-TNF alpha antibody, or antigen binding portion thereof, at a concentration of about 100 mg/mL (or 75-125 mg/mL), a surfactant (e.g., polysorbate 80), a polyol (e.g., sorbitol or mannitol), and has a hydrodynamic diameter of less than 4 nm. In one embodiment, the formulation of the invention contains of a human anti-TNF alpha antibody, or antigen binding portion thereof, at a concentration of about 100 mg/mL (or 75-125 mg/mL), about 0.8-1.3 mg/ml of a surfactant (e.g., polysorbate 80), less than about 50 mg/ml of a polyol (e.g., sorbitol or mannitol), and has a hydrodynamic diameter of less than 4 nm.

In one embodiment, the formulation of the invention contains of a human anti-TNF alpha antibody, or antigen binding portion thereof, at a concentration of about 100 mg/mL (or 75-125 mg/mL), a surfactant (e.g., polysorbate 80), and has a hydrodynamic diameter of less than 4 nm. In one embodiment, the formulation of the invention contains of a human anti-TNF alpha antibody, or antigen binding portion thereof, at a concentration of about 100 mg/mL (or 75-125 mg/mL), about 0.8-1.3 mg/ml of a surfactant (e.g., polysorbate 80), and has a hydrodynamic diameter of less than 4 nm.

A detergent or surfactant is included in the antibody formulation of the invention. Exemplary detergents include nonionic detergents such as polysorbates (e.g. polysorbates 20, 80, etc.) or poloxamers (e.g. poloxamer 188). The amount of detergent added is such that it reduces aggregation of the formulated antibody and/or minimizes the formation of particulates in the formulation and/or reduces adsorption. In a preferred embodiment of the invention, the formulation includes a surfactant which is a polysorbate. In another preferred embodiment of the invention, the formulation contains the detergent polysorbate 80. In one embodiment, the formulation contains between about 0.1 and about 2.0 mg/mL of surfactant (e.g., polysorbate), e.g., about 1 mg/mL. Other ranges of polysorbate that may be included in the formulations of the invention include 0.1 to 1.5 mg/ml, alternatively 0.2-1.4 mg/ml, 0.3-1.3 mg/ml, 0.4-1.2 mg/ml, 0.5-1.1 mg/ml, 0.6-1.0 mg/ml, 0.6-1.1 mg/ml, 0.7-1.1 mg/ml, 0.8-1.1 mg/ml, or 0.9-1.1 mg/ml. Values and ranges intermediate to the above recited concentrations are also intended to be part of this invention, e.g., 0.2, 0.3, 0.4, 0.5, 0.6, 0.7, 0.8, 0.9, 1, 1.1, 1.2, 1.3, 1.4, 1.5, 1.6, 1.7, 1.8, 1.9. In addition, ranges of values using a combination of any of the above-recited values as upper and/or lower limits are intended to be included, e.g., 0.3 to 1.1 mg/mL.

In one embodiment, the formulation of the invention consists essentially of a human anti-TNF alpha antibody, or antigen binding portion thereof, at a concentration of about 100 mg/mL (or 75-125 mg/mL), a surfactant (e.g., polysorbate 80), a polyol (e.g., sorbitol or mannitol), does not contain a buffer(s) (e.g., citric acid monohydrate, sodium citrate, disodium phosphate dihydrate, and/or sodium dihydrogen phosphate dihydrate), and does not contain a salt (e.g., NaCl).

In certain embodiments, the otherwise identical formulation to which the formulation of the invention is compared for pain or bioavailability purposes is a formulation containing adalimumab, sodium chloride, monobasic sodium phosphate dihydrate, dibasic sodium phosphate dihydrate, sodium citrate, citric acid monohydrate, mannitol, polysorbate 80, and Water for Injection.

The formulation herein may also be combined with one or more other therapeutic agents as necessary for the particular indication being treated. In one embodiment, those with complementary activities that do not adversely affect the antibody of the formulation. Such therapeutic agents are suitably present in combination in amounts that are effective for the purpose intended. Additional therapeutic agents which can be combined with the formulation of the invention are further described in U.S. Pat. Nos. 6,090,382 and 6,258,562, each of which is incorporated herein by reference.

All formulations described herein may be used in the methods of the invention as well.

III. Antibodies for Use in the Formulations and Methods of the Invention

The formulations and methods of the invention include an antibody, or antigen binding portion thereof, particularly an anti-TNFα antibody, or antigen binding portion or fragment thereof. Examples of antibodies that may be used in the invention include chimeric antibodies, non-human antibodies, isolated human antibodies, humanized antibodies, and domain antibodies (dAbs). All antibodies described herein may be used in the methods of the invention as well.

In one embodiment, the formulations of the invention comprises an antibody, or antigen-binding portion thereof, which binds human TNFα, including, for example, adalimumab (also referred to as Humira, adalimumab, or D2E7; Abbott Laboratories). In a further embodiment, the formulation comprises an antibody that binds the same epitope as adalimumab, such as, but not limited to, an adalimumab biosimilar antibody. In one embodiment, the antibody is a human IgG1 antibody having six CDRs corresponding to those of the light and heavy chain of adalimumab.

In one embodiment, the invention features an isolated human antibody, or antigen-binding portion thereof, that binds to human TNF-alpha with high affinity and a low off rate, and also has a high neutralizing capacity. In one embodiment, the human antibodies used in the invention are recombinant, neutralizing human anti-hTNF-alpha antibodies.

In one aspect, the invention pertains to adalimumab antibodies and antibody portions, adalimumab-related antibodies and antibody portions, and other human antibodies and antibody portions with equivalent properties to adalimumab, such as high affinity binding to hTNFa. with low dissociation kinetics and high neutralizing capacity. In one embodiment, the antibody, or antigen-binding fragment thereof, is defined according to dissociation and binding characteristics similar to adalimumab. For example, the formulation may include a human antibody that dissociates from human TNFα with a $K_d$ of $1 \times 10^{-8}$ M or less, and a $k_{off}$ rate constant of $1 \times 10^{-3}$ s$^{-1}$ or less, both determined by surface plasmon resonance. In another embodiment, the human antibody that dissociates from human TNFα with a $K_d$ of $1 \times 10^{-9}$ M or less.

In one embodiment, the antibody, or antigen-binding fragment thereof, is a human antibody that dissociates from human TNFα with a $K_d$ of $1 \times 10^{-8}$ M or less, and a $k_{off}$ rate constant of $1 \times 10^{-3}$ s$^{-1}$ or less, both determined by surface plasmon resonance, and neutralizes human TNFα cytotoxicity in a standard in vitro L929 assay with an IC$_{50}$ of $1 \times 10^{-7}$ M or less. Examples and methods for making human, neutralizing antibodies which have a high affinity for human TNFα, including sequences of the antibodies, are described in U.S. Pat. No. 6,090,382 (referred to as D2E7), incorporated by reference herein. The amino sequences of D2E7 as described in U.S. Pat. No. 6,090,382 are incorporated in their entirety herein.

In one embodiment, the antibody used in the formulation of the invention is D2E7, also referred to as HUMIRA™ or adalimumab (the amino acid sequence of the D2E7 VL region is shown in SEQ ID NO: 1; the amino acid sequence of the D2E7 VH region is shown in SEQ ID NO: 2). The properties of D2E7 (adalimumab/HUMIRA®) have been described in Salfeld et al., U.S. Pat. Nos. 6,090,382, 6,258,562, and 6,509,015, which are each incorporated by reference herein.

In one embodiment, the human TNF-alpha, or an antigen-binding portion thereof, dissociates from human TNF-alpha with a $K_d$ of $1 \times 10^{-8}$ M or less and a $k_{off}$ rate constant of $1 \times 10^{-3}$ s$^{-1}$ or less, both determined by surface plasmon resonance, and neutralizes human TNF-alpha cytotoxicity in a standard in vitro L929 assay with an IC$_{50}$ of $1 \times 10^{-7}$ M or less. In one embodiment, the isolated human antibody, or antigen-binding portion thereof, dissociates from human TNF-alpha with a $k_{off}$ of $5 \times 10^{-4}$ s$^{-1}$ or less; or, in one embodiment, with a $k_{off}$ of $1 \times 10^{-4}$ s$^{-1}$ or less. In one embodiment, the isolated human antibody, or antigen-binding portion thereof, neutralizes human TNF-alpha cytotoxicity in a standard in vitro L929 assay with an IC$_{50}$ of $1 \times 10^{-8}$ M or less; or, in one embodiment, with an IC$_{50}$ of $1 \times 10^{-9}$ M or less; or, in one embodiment, with an IC$_{50}$ of $1 \times 10^{-10}$ M or less. In one embodiment, the antibody is an isolated human recombinant antibody, or an antigen-binding portion thereof.

It is well known in the art that antibody heavy and light chain CDR3 domains play an important role in the binding specificity/affinity of an antibody for an antigen. Accordingly, in another aspect, the antibody used in the formulation of the invention has slow dissociation kinetics for association with hTNF-alpha and has light and heavy chain CDR3 domains that structurally are identical to or related to those of adalimumab. Position 9 of the adalimumab VL CDR3 can be occupied by Ala or Thr without substantially affecting the Koff. Accordingly, a consensus motif for the adalimumab VL CDR3 comprises the amino acid sequence: Q-R-Y-N-R-A-P-Y-(T/A) (SEQ ID NO: 3). Additionally, position 12 of the adalimumab VH CDR3 can be occupied by Tyr or Asn, without substantially affecting the $k_{off}$. Accordingly, a consensus motif for the adalimumab VH CDR3 comprises the amino acid sequence: V-S-Y-L-S-T-A-S-S-L-D-(Y/N) (SEQ ID NO: 4). Moreover, as demonstrated in Example 2 of U.S. Pat. No. 6,090,382, the CDR3 domain of the adalimumab heavy and light chains is amenable to substitution with a single alanine residue (at position 1, 4, 5, 7 or 8 within the VL CDR3 or at position 2, 3, 4, 5, 6, 8, 9, 10 or 11 within the VH CDR3) without substantially affecting the $k_{off}$. Still further, the skilled artisan will appreciate that, given the amenability of the adalimumab VL and VH CDR3 domains to substitutions by alanine, substitution of other amino acids within the CDR3 domains may be possible while still retaining the low off rate constant of the antibody, in particular substitutions with conservative amino acids. In one embodiment, no more than one to five conservative amino acid substitutions are made within the adalimumab VL and/or VH CDR3 domains. In one embodiment, no more than one to three conservative amino acid substitutions are made within the adalimumab VL and/or VH CDR3 domains. Additionally, conservative amino acid substitutions should not be made at amino acid positions critical for binding to hTNF alpha. Positions 2 and 5 of the adalimumab VL CDR3 and positions 1 and 7 of the adalimumab VH CDR3 appear to be critical for interaction with hTNF alpha, and thus, conservative amino acid substitutions preferably are not made at these positions (although an alanine substitution at position 5 of the adalimumab VL CDR3 is acceptable, as described above) (see U.S. Pat. No. 6,090,382).

Accordingly, in one embodiment, the antibody or antigen-binding portion thereof, used in the formulation of the invention contains the following characteristics:

a) dissociates from human TNFα with a $k_{off}$ rate constant of $1 \times 10^{-3}$ s$^{-1}$ or less, as determined by surface plasmon resonance;

b) has a light chain CDR3 domain comprising the amino acid sequence of SEQ ID NO: 3, or modified from SEQ ID NO: 3 by a single alanine substitution at position 1, 4, 5, 7 or 8 or by one to five conservative amino acid substitutions at positions 1, 3, 4, 6, 7, 8 and/or 9;

c) has a heavy chain CDR3 domain comprising the amino acid sequence of SEQ ID NO: 4, or modified from SEQ ID NO: 4 by a single alanine substitution at position 2, 3, 4, 5, 6, 8, 9, 10 or 11 or by one to five conservative amino acid substitutions at positions 2, 3, 4, 5, 6, 8, 9, 10, 11 and/or 12.

In certain embodiments, the antibody or antigen-binding portion thereof, dissociates from human TNF-alpha with a $k_{off}$ of $5 \times 10^{-4}$ s$^{-1}$ or less. In certain embodiments, the antibody or antigen-binding portion thereof, dissociates from human TNF-alpha with a $k_{off}$ of $1 \times 10^{-4}$ s$^{-1}$ or less.

In yet another embodiment, the antibody or antigen-binding portion thereof contains a light chain variable region (LCVR) having a CDR3 domain comprising the amino acid sequence of SEQ ID NO: 3, or modified from SEQ ID NO: 3 by a single alanine substitution at position 1, 4, 5, 7 or 8, and with a heavy chain variable region (HCVR) having a CDR3 domain comprising the amino acid sequence of SEQ ID NO: 4, or modified from SEQ ID NO: 4 by a single alanine substitution at position 2, 3, 4, 5, 6, 8, 9, 10 or 11. In one embodiment, the LCVR further has a CDR2 domain comprising the amino acid sequence of SEQ ID NO: 5 (i.e., the D2E7 VL CDR2) and the HCVR further has a CDR2 domain comprising the amino acid sequence of SEQ ID NO: 6 (i.e., the D2E7 VH CDR2). In one embodiment, the LCVR further has CDR1 domain comprising the amino acid sequence of SEQ ID NO: 7 (i.e., the D2E7 VL CDR1) and the HCVR has a CDR1 domain comprising the amino acid sequence of SEQ ID NO: 8 (i.e., the D2E7 VH CDR1). The framework regions for VL may be from the VκI human germline family, or from the A20 human germline Vk gene, or from the adalimumab VL framework sequences shown in FIGS. 1A and 1B of U.S. Pat. No. 6,090,382. The framework regions for VH may be from the VH3 human germline family, or from the DP-31 human germline VH gene, or from the D2E7 VH framework sequences shown in FIGS. 2A and 2B of U.S. Pat. No. 6,090, 382. Nucleic acid sequences corresponding to the adalimumab light and heavy variable regions are described in SEQ ID NOs: 36 and 37, respectively.

Accordingly, in another embodiment, the antibody or antigen-binding portion thereof contains a light chain variable region (LCVR) comprising the amino acid sequence of SEQ ID NO: 1 (i.e., the adalimumab VL) and a heavy chain variable region (HCVR) comprising the amino acid sequence of SEQ ID NO: 2 (i.e., the adalimumab VH). In certain embodiments, the antibody comprises a heavy chain constant region, such as an IgG1, IgG2, IgG3, IgG4, IgA, IgE, IgM or IgD constant region. In certain embodiments, the heavy chain constant region is an IgG1 heavy chain constant region or an IgG4 heavy chain constant region. Furthermore, the antibody can comprise a light chain constant region, either a kappa light chain constant region or a lambda light chain constant region. In one embodiment, the antibody comprises a kappa light chain constant region. Alternatively, the antibody portion can be, for example, a Fab fragment or a single chain Fv fragment.

In still other embodiments, the invention includes uses of an isolated human antibody, or an antigen-binding portion thereof, containing adalimumab-related VL and VH CDR3 domains. For example, antibodies or antigen-binding portions thereof may have a light chain variable region (LCVR) having a CDR3 domain comprising an amino acid sequence selected from the group consisting of SEQ ID NO: 3, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25 and SEQ ID NO: 26 or with a heavy chain variable region (HCVR) having a CDR3 domain comprising an amino acid sequence selected from the group consisting of SEQ ID NO: 4, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34 and SEQ ID NO: 35.

In one embodiment, the TNFα antibody used in the invention includes the chimeric antibody infliximab (Remicade®, Johnson and Johnson; described in U.S. Pat. No. 5,656,272, incorporated by reference herein), CDP571 (a humanized monoclonal anti-TNF-alpha IgG4 antibody), CDP 870 (a humanized monoclonal anti-TNF-alpha antibody fragment), an anti-TNF dAb (Peptech), or CNTO 148 (golimumab; Medarex and Centocor, see WO 02/12502). Additional TNF antibodies which may be used in the invention are described in U.S. Pat. Nos. 6,593,458; 6,498,237; 6,451,983; and 6,448, 380, each of which is incorporated by reference herein.

An antibody, or antibody portion, used in the methods and compositions of the invention, can be prepared by recombinant expression of immunoglobulin light and heavy chain genes in a host cell. To express an antibody recombinantly, a host cell is transfected with one or more recombinant expression vectors carrying DNA fragments encoding the immunoglobulin light and heavy chains of the antibody such that the light and heavy chains are expressed in the host cell and, preferably, secreted into the medium in which the host cells are cultured, from which medium the antibodies can be recovered. Standard recombinant DNA methodologies are used to obtain antibody heavy and light chain genes, incorporate these genes into recombinant expression vectors and introduce the vectors into host cells, such as those described in Sambrook, Fritsch and Maniatis (eds), Molecular Cloning; A Laboratory Manual, Second Edition, Cold Spring Harbor, N.Y., (1989), Ausubel, F. M. et al. (eds.) Current Protocols in Molecular Biology, Greene Publishing Associates, (1989) and in U.S. Pat. No. 4,816,397 by Boss et al.

To express an anti-TNFα antibody, e.g., adalimumab (D2E7) or an adalimumab (D2E7)-related antibody, DNA fragments encoding the light and heavy chain variable regions are first obtained. These DNAs can be obtained by amplification and modification of germline light and heavy chain variable sequences using the polymerase chain reaction (PCR). Germline DNA sequences for human heavy and light chain variable region genes are known in the art (see e.g., the "Vbase" human germline sequence database; see also Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline VH Sequences Reveals about Fifty Groups of VH Segments with Different Hypervariable Loops" J. Mol. Biol. 227:776-798; and Cox, J. P. L. et al. (1994) "A Directory of Human Germline V78 Segments Reveals a Strong Bias in their Usage" Eur. J. Immunol. 24:827-836; the contents of each of which are expressly incorporated herein by reference). For example, to obtain a DNA fragment encoding the heavy chain variable region of D2E7, or a D2E7-related antibody, a member of the VH3 family of human germline VH genes is amplified by standard PCR. In certain embodiments, the DP-31 VH germline sequence is amplified. To obtain a DNA fragment encoding the light chain variable region of D2E7, or a D2E7-related antibody, a member of the VκI family of human germline VL genes is amplified by standard PCR. In certain embodiments, the A20 VL germline sequence is amplified. PCR primers suitable for use in amplifying the DP-31 germline VH and A20 germline VL sequences can be designed based on the nucleotide sequences disclosed in the references cited supra, using standard methods.

Once the germline VH and VL fragments are obtained, these sequences can be mutated to encode the anti-TNFa antibody amino acid sequences disclosed herein. The amino acid sequences encoded by the germline VH and VL DNA sequences are first compared to the anti-TNFa antibody VH and VL amino acid sequences to identify amino acid residues in the anti-TNFa antibody sequence that differ from germline. Then, the appropriate nucleotides of the germline DNA sequences are mutated such that the mutated germline sequence encodes the anti-TNFa antibody amino acid sequence, using the genetic code to determine which nucleotide changes should be made. Mutagenesis of the germline sequences is carried out by standard methods, such as PCR-mediated mutagenesis (in which the mutated nucleotides are incorporated into the PCR primers such that the PCR product contains the mutations) or site-directed mutagenesis.

Moreover, it should be noted that if the "germline" sequences obtained by PCR amplification encode amino acid differences in the framework regions from the true germline configuration (i.e., differences in the amplified sequence as compared to the true germline sequence, for example as a result of somatic mutation), it may be desirable to change these amino acid differences back to the true germline sequences (i.e., "backmutation" of framework residues to the germline configuration).

Once DNA fragments encoding the anti-TNFa antibody VH and VL segments are obtained (e.g., by amplification and mutagenesis of germline VH and VL genes, as described above), these DNA fragments can be further manipulated by standard recombinant DNA techniques, for example to convert the variable region genes to full-length antibody chain genes, to Fab fragment genes or to a scFv gene. In these manipulations, a VL- or VH-encoding DNA fragment is operatively linked to another DNA fragment encoding another protein, such as an antibody constant region or a flexible linker. The term "operatively linked," as used in this context, is intended to mean that the two DNA fragments are joined such that the amino acid sequences encoded by the two DNA fragments remain in-frame.

The isolated DNA encoding the VH region can be converted to a full-length heavy chain gene by operatively linking the VH-encoding DNA to another DNA molecule encoding heavy chain constant regions (CH1, CH2 and CH$_3$). The sequences of human heavy chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the VH-encoding DNA can be operatively linked to another DNA molecule encoding only the heavy chain CH1 constant region.

The isolated DNA encoding the VL region can be converted to a full-length light chain gene (as well as a Fab light chain gene) by operatively linking the VL-encoding DNA to another DNA molecule encoding the light chain constant region, CL. The sequences of human light chain constant region genes are known in the art (see e.g., Kabat, E. A., et al. (1991) Sequences of Proteins of Immunological Interest, Fifth Edition, U.S. Department of Health and Human Services, NIH Publication No. 91-3242) and DNA fragments encompassing these regions can be obtained by standard PCR amplification. The light chain constant region can be a kappa or lambda constant region. In one embodiment, the light chain constant region is a kappa constant region.

To create a scFv gene, the VH- and VL-encoding DNA fragments are operatively linked to another fragment encoding a flexible linker, e.g., encoding the amino acid sequence (Gly$_4$-Ser)$_3$, such that the VH and VL sequences can be expressed as a contiguous single-chain protein, with the VL and VH regions joined by the flexible linker (see e.g., Bird et al. (1988) Science 242:423-426; Huston et al. (1988) Proc. Natl. Acad. Sci. USA 85:5879-5883; McCafferty et al., Nature (1990) 348:552-554).

To express the antibodies, or antibody portions used in the invention, DNAs encoding partial or full-length light and heavy chains, obtained as described above, are inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or, more typically, both genes are inserted into the same expression vector. The antibody genes are inserted into the expression vector by standard methods (e.g., ligation of complementary restriction sites on the antibody gene fragment and vector, or blunt end ligation if no restriction sites are present). Prior to insertion of the anti-TNFa antibody light or heavy chain sequences, the expression vector may already carry antibody constant region sequences. For example, one approach to converting the anti-TNFa antibody VH and VL sequences to full-length antibody genes is to insert them into expression vectors already encoding heavy chain constant and light chain constant regions, respectively, such that the VH segment is operatively linked to the CH segment(s) within the vector and the VL segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, the recombinant expression vectors of the invention carry regulatory sequences that control the expression of the antibody chain genes in a host cell. The term "regulatory sequence" is intended to include promoters, enhancers and other expression control elements (e.g., polyadenylation signals) that control the transcription or translation of the antibody chain genes. Such regulatory sequences are described, for example, in Goeddel; Gene Expression Technology: Methods in Enzymology 185, Academic Press, San Diego, Calif. (1990). It will be appreciated by those skilled in the art that the design of the expression vector, including the selection of regulatory sequences may depend on such factors as the choice of the host cell to be transformed, the level of expression of protein desired, etc. Preferred regulatory sequences for mammalian host cell expression include viral elements that direct high levels of protein expression in mammalian cells, such as promoters and/or enhancers derived from cytomegalovirus (CMV) (such as the CMV promoter/enhancer), Simian Virus 40 (SV40) (such as the SV40 promoter/enhancer), adenovirus, (e.g., the adenovirus major late promoter (AdMLP)) and polyoma. For further description of viral regulatory elements, and sequences thereof, see e.g., U.S. Pat. No. 5,168,062 by Stinski, U.S. Pat. No. 4,510,245 by Bell et al. and U.S. Pat. No. 4,968,615 by Schaffner et al.

In addition to the antibody chain genes and regulatory sequences, the recombinant expression vectors used in the invention may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017, all by Axel et al.). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the invention in either prokaryotic or eukaryotic host cells, expression of antibodies is preferably in eukaryotic cells. In one embodiment, mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) Immunology Today 6:12-13).

Preferred mammalian host cells for expressing the recombinant antibodies of the invention include Chinese Hamster Ovary (CHO cells) (including dhfr-CHO cells, described in Urlaub and Chasin, (1980) Proc. Natl. Acad. Sci. USA 77:4216-4220, used with a DHFR selectable marker, e.g., as described in R. J. Kaufman and P. A. Sharp (1982) Mol. Biol. 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more, in one embodiment, secretion of the antibody into the culture medium in which the host cells are grown. Antibodies can be recovered from the culture medium using standard protein purification methods.

Host cells can also be used to produce portions of intact antibodies, such as Fab fragments or scFv molecules. It is understood that variations on the above procedure are within the scope of the present invention. For example, it may be desirable to transfect a host cell with DNA encoding either the light chain or the heavy chain (but not both) of an antibody of this invention. Recombinant DNA technology may also be used to remove some or all of the DNA encoding either or both of the light and heavy chains that is not necessary for binding to hTNF alpha. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than hTNF alpha by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are culture to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium.

In view of the foregoing, nucleic acid, vector and host cell compositions that can be used for recombinant expression of the antibodies and antibody portions used in the invention include nucleic acids, and vectors comprising said nucleic acids, comprising the human TNF alpha antibody adalimumab (D2E7). The nucleotide sequence encoding the D2E7 light chain variable region is shown in SEQ ID NO: 36. The CDR1 domain of the LCVR encompasses nucleotides 70-102, the CDR2 domain encompasses nucleotides 148-168 and the CDR3 domain encompasses nucleotides 265-291. The nucleotide sequence encoding the D2E7 heavy chain variable region is shown in SEQ ID NO: 37. The CDR1 domain of the HCVR encompasses nucleotides 91-105, the CDR2 domain encompasses nucleotides 148-198 and the CDR3 domain encompasses nucleotides 295-330. It will be appreciated by the skilled artisan that nucleotide sequences encoding D2E7-related antibodies, or portions thereof (e.g., a CDR domain, such as a CDR3 domain), can be derived from the nucleotide sequences encoding the D2E7 LCVR and HCVR using the genetic code and standard molecular biology techniques.

In one embodiment, the liquid pharmaceutical formulation comprises a human TNF alpha antibody, or antigen-binding portion thereof, that is a bioequivalent or biosimilar to the antibody adalimumab. In one embodiment, a biosimilar antibody is an antibody which shows no clinically meaningful difference when compared to a reference antibody, e.g., adalimumab. A biosimilar antibody has equivalent safety, purity, and potency as a reference antibody, e.g., adalimumab.

IV. Administration of the Formulations of the Invention for Treatment of TNFa-Related Disorders An advantage of the formulations of the invention is that they may be used to deliver a high concentration of an anti-TNF alpha antibody, or antigen-binding portion, (e.g., adalimumab) to a subject subcutaneously such that either pain upon injection is decreased or the bioavailability of the antibody is improved. Thus, in one embodiment, the formulation of the invention is delivered to a subject subcutaneously. In one embodiment, the subject administers the formulation to himself/herself (self-administration).

In one embodiment, an effective amount of the formulation is administered. An example of an effective amount of the formulation is an amount sufficient to inhibit detrimental TNF-alpha activity or treat a disorder in which TNF alpha activity is detrimental.

As used herein, the term "a disorder in which TNF-alpha activity is detrimental" is intended to include diseases and other disorders in which the presence of TNF-alpha. in a subject suffering from the disorder has been shown to be or is suspected of being either responsible for the pathophysiology of the disorder or a factor that contributes to a worsening of the disorder. Accordingly, a disorder in which TNF-alpha. activity is detrimental is a disorder in which inhibition of TNF-alpha activity is expected to alleviate the symptoms and/or progression of the disorder. Such disorders may be evidenced, for example, by an increase in the concentration of TNF-alpha. in a biological fluid of a subject suffering from the disorder (e.g., an increase in the concentration of TNF-alpha. in serum, plasma, synovial fluid, etc. of the subject), which can be detected, for example, using an anti-TNF-alpha. antibody.

In one embodiment, the effective amount of antibody may be determined according to a strictly weight based dosing scheme (e.g., mg/kg) or may be a total body dose (also referred to as a fixed dose) which is independent of weight. In one embodiment, an effective amount of the antibody is about 20, 25, 30, 35, 40, 45, 50, 55, 60, 65, 70, 75, 80, 85, 90, 95, or about 100 mg of the human anti-TNFα antibody, or antigen-binding portion thereof. In one embodiment, an effective amount of the antibody is about 20-100, about 20-90, about 30-90, about 30-100, about 60-100, about 70-90, about 40-90, about 60-85 mg, or about 40-100 mg. In one embodiment, the formulation contains an effective amount of the antibody of 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, or 100 mg of the antibody. Ranges including the aforementioned numbers are also included in the invention, e.g., 70-90 or 75-85 mg or 60-85 mg.

In one example, an effective amount of the formulation is 0.4 mL or 0.8 mL of the formulation containing a total body dose of about 80 mg of antibody (i.e., 0.8 mL of a 100 mg/mL antibody formulation of the invention). In another example, an effective amount of the formulation is 0.4 mL of the formulation of the invention containing a total body dose of about 40 mg of antibody (i.e., 0.4 mL of a 100 mg/mL antibody formulation of the invention). In yet another example, an effective amount of the formulation is twice 0.8 mL of the formulation containing a total body dose of about 160 mg of antibody (i.e., two units containing 0.8 mL each of a 100 mg/mL antibody formulation of the invention). In a further example, an effective amount of the formulation is 0.2 mL of the formulation of the invention containing a total body dose of about 20 mg of antibody (i.e., 0.2 mL of a 100 mg/mL antibody formulation of the invention). Alternatively, an effective amount may be determined according to a weight-based fixed dosing regimen (see, e.g., WO 2008/154543, incorporated by reference herein).

In one embodiment, the TNF-alpha is human TNF-alpha and the subject is a human subject. Alternatively, the subject can be a mammal expressing a TNF-alpha with which an antibody of the invention cross-reacts. Still further the subject can be a mammal into which has been introduced hTNF-alpha (e.g., by administration of hTNF-alpha or by expression of an hTNF-alpha transgene).

A formulation of the invention may be administered to a human subject for therapeutic purposes (discussed further below). In one embodiment of the invention, the liquid pharmaceutical formulation is easily administratable, which includes, for example, a formulation which is self-administered by the patient. In one embodiment, the formulation of the invention is administered through subcutaneous injection, such as single use subcutaneous injection. Moreover, a formulation of the invention can be administered to a non-human mammal expressing a TNF-alpha with which the antibody cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration).

The formulations of the invention may be administered according to a certain dosing schedule. For example, the formulations may be administered according to a weekly, biweekly, or monthly dosing regimen. Alternatively, the formulation may be administered once every three weeks. In one embodiment, the formulations and methods comprise administration to the subject of a human anti-TNFα antibody according to a periodicity selected from the group consisting of weekly, biweekly, every three weeks, and monthly.

In one embodiment, the liquid aqueous formulation of the invention may be administered to a subject via, for example, a prefilled syringe, an autoinjector pen, or a needle-free administration device. Thus, the invention also features an autoinjector pen, a prefilled syringe, or a needle-free administration device comprising the liquid aqueous formulation of the invention. In one embodiment, the invention features a delivery device comprising a dose of the formulation comprising 100 mg/mL a human TNF alpha antibody, or antigen-binding portion thereof, e.g., an autoinjector pen or prefilled syringe comprises a dose of about 19 mg, 20, mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, etc. of the formulation. In one embodiment, the syringe or autoinjector contains 60-100 mg, 70-90 mg, or about 80 mg of the antibody.

In one embodiment, the formulations of the invention may be self administered using, e.g., a preloaded syringe or an automatic injection device. Automatic injection devices offer an alternative to manually-operated syringes for delivering therapeutic agents into patients' bodies and allowing patients to self-administer injections. Automatic injection devices are described, for example, in the following publications, each of which is hereby incorporated herein by reference WO 2008/005315, WO 2010/127146, WO 2006/000785, WO 2011/075524, WO 2005/113039, WO 2011/075524.

Accordingly, in one embodiment, the present invention provides pre-filled syringes or autoinjector devices containing the formulations of the invention, as well as use of pre-filled syringes or autoinjector devices comprising the formulations described herein in the methods of the invention.

In one embodiment, the formulation of the invention is used to treat disorders in which TNF alpha activity is detrimental. As used herein, the term "a disorder in which TNF-alpha activity is detrimental" is intended to include diseases and other disorders in which the presence of TNF-alpha in a subject suffering from the disorder has been shown to be or is suspected of being either responsible for the pathophysiology of the disorder or a factor that contributes to a worsening of the disorder. Accordingly, a disorder in which TNF-alpha activity is detrimental is a disorder in which inhibition of TNF-alpha activity is expected to alleviate the symptoms and/or progression of the disorder. Such disorders may be evidenced, for example, by an increase in the concentration of TNF-alpha in a biological fluid of a subject suffering from the disorder (e.g., an increase in the concentration of TNF-alpha in serum, plasma, synovial fluid, etc. of the subject), which can be detected, for example, using an anti-TNF-alpha antibody as described above.

There are numerous examples of disorders in which TNF-alpha activity is detrimental. Examples in which TNF-alpha activity is detrimental are also described in U.S. Pat. Nos. 6,015,557; 6,177,077; 6,379,666; 6,419,934; 6,419,944; 6,423,321; 6,428,787; and 6,537,549; and PCT Publication Nos. WO 00/50079 and WO 01/49321, the entire contents of all of which are incorporated herein by reference. The formulations of the invention may also be used to treat disorders in which TNF alpha activity is detrimental as described in U.S. Pat. Nos. 6,090,382, 6,258,562 and U.S. Patent Application Publication No. US20040126372, the entire contents of all of which are incorporated herein by reference.

The use of the formulations of the invention in the treatment of specific exemplary disorders is discussed further below:

A. Sepsis

The formulations and methods of the invention may be used to treat subjects having sepsis. Tumor necrosis factor has an established role in the pathophysiology of sepsis, with biological effects that include hypotension, myocardial suppression, vascular leakage syndrome, organ necrosis, stimulation of the release of toxic secondary mediators and activation of the clotting cascade (see e.g., Tracey, K. J. and Cerami, A. (1994) Annu. Rev. Med. 45:491-503; Russell, D and Thompson, R. C. (1993) Curr. Opin. Biotech. 4:714-721). Accordingly, the formulation of the invention can be used to treat sepsis in any of its clinical settings, including septic shock, endotoxic shock, gram negative sepsis and toxic shock syndrome.

Furthermore, to treat sepsis, the formulation of the invention can be coadministered with one or more additional therapeutic agents that may further alleviate sepsis, such as an interleukin-1 inhibitor (such as those described in PCT Publication Nos. WO 92/16221 and WO 92/17583), the cytokine interleukin-6 (see e.g., PCT Publication No. WO 93/11793) or an antagonist of platelet activating factor (see e.g., European Patent Application Publication No. EP 374 510).

Additionally, in one embodiment, the formulation of the invention is administered to a human subject within a subgroup of sepsis patients having a serum or plasma concentration of IL-6 above 500 pg/ml; or, in one embodiment, 1000 pg/ml, at the time of treatment (see PCT Publication No. WO 95/20978).

B. Autoimmune Diseases

The formulations and methods of the invention may be used to treat subjects having an autoimmune disease. Tumor necrosis factor has been implicated in playing a role in the pathophysiology of a variety of autoimmune diseases. For example, TNF-alpha has been implicated in activating tissue inflammation and causing joint destruction in rheumatoid arthritis (see e.g., Tracey and Cerami, supra; Arend, W. P. and Dayer, J-M. (1995) Arth. Rheum. 38:151-160; Fava, R. A., et al. (1993) Clin. Exp. Immunol. 94:261-266). TNF-alpha also has been implicated in promoting the death of islet cells and in mediating insulin resistance in diabetes (see e.g., Tracey and Cerami, supra; PCT Publication No. WO 94/08609). TNF-alpha also has been implicated in mediating cytotoxicity to oligodendrocytes and induction of inflammatory plaques in multiple sclerosis (see e.g., Tracey and Cerami, supra). Also included in autoimmune diseases that may be treated using the formulations and methods of the invention is juvenile idiopathic arthritis (JIA) (also referred to as juvenile rheumatoid arthritis) (see Grom et al. (1996) Arthritis Rheum. 39:1703; Mangge et al. (1995) Arthritis Rheum. 8:211).

The formulation of the invention can be used to treat autoimmune diseases, in particular those associated with inflammation, including rheumatoid arthritis, rheumatoid spondylitis (also referred to as ankylosing spondylitis), osteoarthritis and gouty arthritis, allergy, multiple sclerosis, autoimmune diabetes, autoimmune uveitis, juvenile idiopathic arthritis (also referred to as juvenile rheumatoid arthritis), and nephrotic syndrome.

C. Infectious Diseases

The formulations and methods of the invention may be used to treat subjects having an infectious disease. Tumor necrosis factor has been implicated in mediating biological effects observed in a variety of infectious diseases. For example, TNF-alpha has been implicated in mediating brain inflammation and capillary thrombosis and infarction in malaria (see e.g., Tracey and Cerami, supra). TNF-alpha also has been implicated in mediating brain inflammation, inducing breakdown of the blood-brain barrier, triggering septic shock syndrome and activating venous infarction in meningitis (see e.g., Tracey and Cerami, supra). TNF-alpha also has been implicated in inducing cachexia, stimulating viral proliferation and mediating central nervous system injury in acquired immune deficiency syndrome (AIDS) (see e.g., Tracey and Cerami, supra). Accordingly, the antibodies, and antibody portions, of the invention, can be used in the treatment of infectious diseases, including bacterial meningitis (see e.g., European Patent Application Publication No. EP 585 705), cerebral malaria, AIDS and AIDS-related complex (ARC) (see e.g., European Patent Application Publication No. EP 230 574), as well as cytomegalovirus infection secondary to transplantation (see e.g., Fietze, E., et al. (1994) Transplantation 58:675-680). The formulation of the invention, also can be used to alleviate symptoms associated with infectious diseases, including fever and myalgias due to infection (such as influenza) and cachexia secondary to infection (e.g., secondary to AIDS or ARC).

D. Transplantation

The formulations and methods of the invention may be used to treat subjects having a transplantation. Tumor necrosis factor has been implicated as a key mediator of allograft rejection and graft versus host disease (GVHD) and in mediating an adverse reaction that has been observed when the rat antibody OKT3, directed against the T cell receptor CD3 complex, is used to inhibit rejection of renal transplants (see e.g., Tracey and Cerami, supra; Eason, J. D., et al. (1995) Transplantation 59:300-305; Suthanthiran, M. and Strom, T. B. (1994) New Engl. J. Med. 331:365-375). Accordingly, the formulations of the invention can be used to inhibit transplant rejection, including rejections of allografts and xenografts and to inhibit GVHD. Although the antibody or antibody portion may be used alone, it can be used in combination with one or more other agents that inhibit the immune response against the allograft or inhibit GVHD. For example, in one embodiment, the formulations of the invention are used in combination with OKT3 to inhibit OKT3-induced reactions. In another embodiment, the formulation of the invention is used in combination with one or more antibodies directed at other targets involved in regulating immune responses, such as the cell surface molecules CD25 (interleukin-2 receptor-.alpha.), CD11a (LFA-1), CD54 (ICAM-1), CD4, CD45, CD28/CTLA4, CD80 (B7-1) and/or CD86 (B7-2). In yet another embodiment, the formulation of the invention is used in combination with one or more general immunosuppressive agents, such as cyclosporin A or FK506.

E. Malignancy

The formulations and methods of the invention may be used to treat subjects having cancer or a malignant tumor. Tumor necrosis factor has been implicated in inducing cachexia, stimulating tumor growth, enhancing metastatic potential and mediating cytotoxicity in malignancies (see e.g., Tracey and Cerami, supra). Accordingly, the formulations of the invention can be used in the treatment of malignancies, to inhibit tumor growth or metastasis and/or to alleviate cachexia secondary to malignancy. The formulation of the invention may be administered systemically or locally to the tumor site.

F. Pulmonary Disorders

The formulations and methods of the invention may be used to treat subjects having a pulmonary disease. Tumor necrosis factor has been implicated in the pathophysiology of adult respiratory distress syndrome, including stimulating leukocyte-endothelial activation, directing cytotoxicity to pneumocytes and inducing vascular leakage syndrome (see e.g., Tracey and Cerami, supra). Accordingly, the formulations of the invention can be used to treat various pulmonary disorders, including adult respiratory distress syndrome (see e.g., PCT Publication No. WO 91/04054), shock lung, chronic pulmonary inflammatory disease, pulmonary sarcoidosis, pulmonary fibrosis and silicosis. The formulation of the invention may be administered systemically or locally to the lung surface, for example as an aerosol.

G. Intestinal Disorders

The formulations and methods of the invention may be used to treat subjects having an intestinal disorder. Tumor necrosis factor has been implicated in the pathophysiology of inflammatory bowel disorders (see e.g., Tracy, K. J., et al. (1986) Science 234:470-474; Sun, X-M., et al. (1988) J. Clin. Invest. 81:1328-1331; MacDonald, T. T., et al. (1990) Clin. Exp. Immunol. 81:301-305) Chimeric murine anti-hTNF-alpha antibodies have undergone clinical testing for treatment of Crohn's disease (van Dullemen, H. M., et al. (1995) Gastroenterology 109:129-135). The formulation of the invention, also can be used to treat intestinal disorders, such as idiopathic inflammatory bowel disease, which includes two syndromes, Crohn's disease and ulcerative colitis. In one embodiment, the formulation of the invention is used to treat Crohn's disease. In one embodiment, the formulation of the invention is used to treat ulcerative colitis.

H. Cardiac Disorders

The formulations and methods of the invention, also can be used to treat various cardiac disorders, including ischemia of the heart (see e.g., European Patent Application Publication No. EP 453 898) and heart insufficiency (weakness of the heart muscle) (see e.g., PCT Publication No. WO 94/20139).

I. Spondyloarthropathies

The formulations and methods of the invention may also be used to treat subjects who have a spondyloarthropathy, including, for example, an axial spondyloarthropathy. TNFα has been implicated in the pathophysiology of a wide variety of disorders, including inflammatory diseases such as spondyloarthopathies (see e.g., Moeller, A., et al. (1990) Cytokine 2:162-169; U.S. Pat. No. 5,231,024 to Moeller et al.; European Patent Publication No. 260 610 B1 by Moeller, A). In one embodiment, the spondyloarthropathy is an axial spondyloarthropathy. Other examples of spondyloarthropathies which can be treated with the TNFα antibody of the invention are described below:

1. Psoriatic Arthritis

The formulations and methods of the invention may also be used to treat subjects who have psoriatic arthritis. Tumor necrosis factor has been implicated in the pathophysiology of psoriatic arthritis (Partsch et al. (1998) *Ann Rheum Dis.* 57:691; Ritchlin et al. (1998) *J Rheumatol.* 25:1544). As referred to herein, psoriatic arthritis (PsA) or psoriasis associated with the skin, refers to chronic inflammatory arthritis which is associated with psoriasis. Psoriasis is a common chronic skin condition that causes red patches on the body. About 1 in 20 individuals with psoriasis will develop arthritis along with the skin condition, and in about 75% of cases, psoriasis precedes the arthritis. PsA exhibits itself in a variety of ways, ranging from mild to severe arthritis, wherein the arthritis usually affects the fingers and the spine. When the spine is affected, the symptoms are similar to those of ankylosing spondylitis, as described above.

PsA is sometimes associated with arthritis mutilans. Arthritis mutilans refers to a disorder which is characterized by excessive bone erosion resulting in a gross, erosive deformity which mutilates the joint. In one embodiment, formulations and methods of the invention can be used to treat arthritis mutilans.

2. Reactive Arthritis/Reiter's Syndrome

The formulations and methods of the invention may also be used to treat subjects who have Reiter's syndrome or reactive arthritis. Tumor necrosis factor has been implicated in the pathophysiology of reactive arthritis, which is also referred to as Reiter's syndrome (Braun et al. (1999) *Arthritis Rheum.* 42(10):2039). Reactive arthritis (ReA) refers to arthritis which complicates an infection elsewhere in the body, often following enteric or urogenital infections. ReA is often characterized by certain clinical symptoms, including inflammation of the joints (arthritis), urethritis, conjunctivitis, and lesions of the skin and mucous membranes. In addition, ReA can occurs following infection with a sexually transmitted disease or dysenteric infection, including *chlamydia, campylobacter, salmonella,* or *yersinia*.

3. Undifferentiated Spondyloarthropathies

The formulations and methods of the invention may also be used to treat subjects who have an undifferentiated spondyloarthropathy (see Zeidler et al. (1992) *Rheum Dis Clin North Am.* 18:187). Other terms used to describe undifferentiated spondyloarthropathies include seronegative oligoarthritis and undifferentiated oligoarthritis. Undifferentiated spondyloarthropathies, as used herein, refers to a disorder wherein the subject demonstrates only some of the symptoms associated with a spondyloarthropathy. This condition is usually observed in young adults who do not have IBD, psoriasis, or the classic symptoms of AS or Reiter's syndrome. In some instances, undifferentiated spondyloarthropathies may be an early indication of AS.

J. Skin and Nail Disorders

In one embodiment, the formulations and methods of the invention are used to treat a skin and/or a nail disorder. As used herein, the term "skin and nail disorder in which TNFα activity is detrimental" is intended to include skin and/or nail disorders and other disorders in which the presence of TNF alpha in a subject suffering from the disorder has been shown to be or is suspected of being either responsible for the pathophysiology of the disorder or a factor that contributes to a worsening of the disorder, e.g., psoriasis. An example of a skin disorder which may be treated using the formulation of the invention is psoriasis. In one embodiment, the formulation of the invention is used to treat plaque psoriasis. Tumor necrosis factor has been implicated in the pathophysiology of psoriasis (Takematsu et al. (1989) Arch Dermatol Res. 281: 398; Victor and Gottlieb (2002) J Drugs Dermatol. 1(3):264).

1. Psoriasis

The formulations and methods of the invention may be used to treat subjects having psoriasis, including subjects having plaque psoriasis. Tumor necrosis factor has been implicated in the pathophysiology of psoriasis (Takematsu et al. (1989) Arch Dermatol Res. 281:398; Victor and Gottlieb (2002) J Drugs Dermatol. 1(3):264). Psoriasis is described as a skin inflammation (irritation and redness) characterized by frequent episodes of redness, itching, and thick, dry, silvery scales on the skin. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the epidermis and polymorphonuclear leukocyte and lymphocyte infiltration into the epidermis layer resulting in an increase in the basal cell cycle. Psoriasis often involves the nails, which frequently exhibit pitting, separation of the nail, thickening, and discoloration. Psoriasis is often associated with other inflammatory disorders, for example arthritis, including rheumatoid arthritis, inflammatory bowel disease (IBD), and Crohn's disease.

Evidence of psoriasis is most commonly seen on the trunk, elbows, knees, scalp, skin folds, or fingernails, but it may affect any or all parts of the skin. Normally, it takes about a month for new skin cells to move up from the lower layers to the surface. In psoriasis, this process takes only a few days, resulting in a build-up of dead skin cells and formation of thick scales. Symptoms of psoriasis include: skin patches, that are dry or red, covered with silvery scales, raised patches of skin, accompanied by red borders, that may crack and become painful, and that are usually located on the elbows, knees, trunk, scalp, and hands; skin lesions, including pustules, cracking of the skin, and skin redness; joint pain or aching which may be associated with of arthritis, e.g., psoriatic arthritis.

Treatment for psoriasis often includes a topical corticosteroids, vitamin D analogs, and topical or oral retinoids, or combinations thereof. In one embodiment, the TNFalpha inhibitor of the invention is administered in combination with or the presence of one of these common treatments.

The diagnosis of psoriasis is usually based on the appearance of the skin. Additionally a skin biopsy, or scraping and culture of skin patches may be needed to rule out other skin disorders. An x-ray may be used to check for psoriatic arthritis if joint pain is present and persistent.

In one embodiment of the invention, a TNFalpha inhibitor is used to treat psoriasis, including chronic plaque psoriasis, guttate psoriasis, inverse psoriasis, pustular psoriasis, pemphigus vulgaris, erythrodermic psoriasis, psoriasis associated with inflammatory bowel disease (IBD), and psoriasis associated with rheumatoid arthritis (RA). Specific types of psoriasis included in the treatment methods of the invention are described in detail below:

a. Chronic Plaque Psoriasis

The formulations and methods of the invention may be used to treat subjects having chronic plaque psoriasis. Tumor necrosis factor has been implicated in the pathophysiology of chronic plaque psoriasis (Asadullah et al. (1999) Br J. Dermatol. 141:94). Chronic plaque psoriasis (also referred to as psoriasis vulgaris) is the most common form of psoriasis. Chronic plaque psoriasis is characterized by raised reddened patches of skin, ranging from coin-sized to much larger. In chronic plaque psoriasis, the plaques may be single or multiple, they may vary in size from a few millimeters to several centimeters. The plaques are usually red with a scaly surface, and reflect light when gently scratched, creating a "silvery" effect. Lesions (which are often symmetrical) from chronic plaque psoriasis occur all over body, but with predilection for extensor surfaces, including the knees, elbows, lumbosacral regions, scalp, and nails. Occasionally chronic plaque psoriasis can occur on the penis, vulva and flexures, but scaling is usually absent. Diagnosis of patients with chronic plaque psoriasis is usually based on the clinical features described above. In particular, the distribution, color and typical silvery scaling of the lesion in chronic plaque psoriasis are characteristic of chronic plaque psoriasis.

b. Guttate Psoriasis

The formulations and methods of the invention may be used to treat subjects having guttate psoriasis. Guttate psoriasis refers to a form of psoriasis with characteristic water drop shaped scaly plaques. Flares of guttate psoriasis generally follow an infection, most notably a streptococcal throat infection. Diagnosis of guttate psoriasis is usually based on the appearance of the skin, and the fact that there is often a history of recent sore throat.

c. Inverse Psoriasis

The formulations and methods of the invention may be used to treat subjects having inverse psoriasis. Inverse psoriasis is a form of psoriasis in which the patient has smooth, usually moist areas of skin that are red and inflamed, which is unlike the scaling associated with plaque psoriasis. Inverse psoriasis is also referred to as intertiginous psoriasis or flexural psoriasis. Inverse psoriasis occurs mostly in the armpits, groin, under the breasts and in other skin folds around the genitals and buttocks, and, as a result of the locations of presentation, rubbing and sweating can irritate the affected areas.

d. Pustular Psoriasis

The formulations and methods of the invention may be used to treat subjects having pustular psoriasis. Pustular psoriasis is a form of psoriasis that causes pus-filled blisters that vary in size and location, but often occur on the hands and feet. The blisters may be localized, or spread over large areas of the body. Pustular psoriasis can be both tender and painful, can cause fevers.

e. Other Psoriasis Disorders

Other examples of psoriatic disorders which can be treated with the formulations and methods of the invention include erythrodermic psoriasis, vulgaris, psoriasis associated with IBD, and psoriasis associated with arthritis, including rheumatoid arthritis.

2. Pemphigus Vulgaris

The formulations and methods of the invention may be used to treat subjects having pemphigus vulgaris. Pemphigus vulgaris is a serious autoimmune systemic dermatologic disease that often affects the oral mucous membrane and skin. The pathogenesis of pemphigus vulgaris is thought to be an autoimmune process that is directed at skin and oral mucous membrane desmosomes. Consequentially, cells do not adhere to each other. The disorder manifests as large fluid-filled, rupture-prone bullae, and has a distinctive histologic appearance. Anti-inflammatory agents are the only effective therapy for this disease which has a high mortality rate. Complications that arise in patients suffering from pemphigus vulgaris are intractable pain, interference with nutrition and fluid loss, and infections.

3. Atopic Dermatitis/Eczema

The formulations and methods of the invention may be used to treat subjects having atopic dermatitis. Atopic dermatitis (also referred to as eczema) is a chronic skin disorder categorized by scaly and itching plaques. People with eczema often have a family history of allergic conditions like asthma, hay fever, or eczema. Atopic dermatitis is a hypersensitivity reaction (similar to an allergy) which occurs in the skin, causing chronic inflammation. The inflammation causes the skin to become itchy and scaly. Chronic irritation and scratching can cause the skin to thicken and become leathery-textured. Exposure to environmental irritants can worsen symptoms, as can dryness of the skin, exposure to water, temperature changes, and stress.

Subjects with atopic dermatitis can be identified by certain symptoms, which often include intense itching, blisters with oozing and crusting, skin redness or inflammation around the blisters, rash, dry, leathery skin areas, raw areas of the skin from scratching, and ear discharges/bleeding.

4. Sarcoidosis

The formulations and methods of the invention may be used to treat subjects having sarcoidosis. Sarcoidosis is a disease in which granulomatous inflammation occurs in the lymph nodes, lungs, liver, eyes, skin, and/or other tissues. Sarcoidosis includes cutaneous sarcoidosis (sarcoidosis of the skin) and nodular sarcoidosis (sarcoidosis of the lymph nodes). Patients with sarcoidosis can be identified by the symptoms, which often include general discomfort, uneasiness, or an ill feeling; fever; skin lesions.

5. Erythema Nodosum

The formulations and methods of the invention may be used to treat subjects having erythema nodosum. Erythema nodosum refers to an inflammatory disorder that is characterized by tender, red nodules under the skin, typically on the anterior lower legs. Lesions associated with erythema nodosum often begin as flat, but firm, hot red painful lumps (approximately an inch across). Within a few days the lesions may become purplish, and then over several weeks fade to a brownish flat patch.

In some instances, erythema nodosum may be associated with infections including, streptococcus, coccidioidomycosis, tuberculosis, hepatitis B, syphilis, cat scratch disease, tularemia, *yersinia*, leptospirosis psittacosis, histoplasmosis, mononucleosis (EBV). In other instances, erythema nodosum may be associated with sensitivity to certain medications including, oralcontraceptives, penicillin, sulfonamides, sulfones, barbiturates, hydantoin, phenacetin, salicylates, iodides, and progestin. Erythema nodosum is often associated with other disorders including, leukemia, sarcoidosis, rheumatic fever, and ulcerative colitis.

Symptoms of erythema nodosum usually present themselves on the shins, but lesions may also occur on other areas of the body, including the buttocks, calves, ankles, thighs and upper extremities. Other symptoms in subjects with erythema nodosum can include fever and malaise.

6. Hidradenitis Suppurativa

The formulations and methods of the invention may be used to treat subjects having hidradenitis suppurativa. Hidradenitis suppurativa refers to a skin disorder in which swollen, painful, inflamed lesions or lumps develop in the groin and sometimes under the arms and under the breasts. Hidradenitis suppurativa occurs when apocrine gland outlets become blocked by perspiration or are unable to drain normally because of incomplete gland development. Secretions trapped in the glands force perspiration and bacteria into surrounding tissue, causing subcutaneous induration, inflammation, and infection. Hidradenitis suppurativa is confined to areas of the body that contain apocrine glands. These areas are the axillae, areola of the nipple, groin, perineum, circumanal, and periumbilical regions.

7. Lichen Planus

The formulations and methods of the invention may be used to treat subjects having lichen planus. Tumor necrosis factor has been implicated in the pathophysiology of lichen planus (Sklavounou et al. (2000) J Oral Pathol Med. 29:370). Lichen planus refers to a disorder of the skin and the mucous membranes resulting in inflammation, itching, and distinctive skin lesions. Lichen planus may be associated with hepatitis C or certain medications.

8. Sweet's Syndrome

The formulations and methods of the invention may be used to treat subjects having Sweet's syndrome. Inflammatory cytokines, including tumor necrosis factor, have been implicated in the pathophysiology of Sweet's syndrome (Reuss-Borst et al. (1993) Br J Haematol. 84:356). Sweet's syndrome, which was described by R. D. Sweet in 1964, is characterized by the sudden onset of fever, leukocytosis, and cutaneous eruption. The eruption consists of tender, erythematous, well-demarcated papules and plaques which show dense neutrophilic infiltrates microscopically. The lesions may appear anywhere, but favor the upper body including the face. The individual lesions are often described as pseudovesicular or pseudopustular, but may be frankly pustular, bullous, or ulcerative. Oral and eye involvement (conjunctivitis or episcleritis) have also been frequently reported in patients with Sweet's syndrome. Leukemia has also been associated with Sweet's syndrome.

9. Vitiligo

The formulations and methods of the invention may be used to treat subjects having vitiligo. Vitiligo refers to a skin condition in which there is loss of pigment from areas of skin resulting in irregular white patches with normal skin texture. Lesions characteristic of vitiligo appear as flat depigmented areas. The edges of the lesions are sharply defined but irregular. Frequently affected areas in subjects with vitiligo include the face, elbows and knees, hands and feet, and genitalia.

10. Scleroderma

The formulations and methods of the invention may be used to treat subjects having scleroderma. Tumor necrosis factor has been implicated in the pathophysiology of scleroderma (Tutuncu Z et al. (2002) Clin Exp Rheumatol. 20(6 Suppl 28):S146-51; Mackiewicz Z et al. (2003) Clin Exp Rheumatol. 21(1):41-8; Murota H et al. (2003) Arthritis Rheum. 48(4):1117-25). Scleroderma refers to a diffuse connective tissue disease characterized by changes in the skin, blood vessels, skeletal muscles, and internal organs. Scleroderma is also referred to as CREST syndrome or Progressive systemic sclerosis, and usually affects people between the ages 30-50. Women are affected more often than men.

The cause of scleroderma is unknown. The disease may produce local or systemic symptoms. The course and severity of the disease varies widely in those affected. Excess collagen deposits in the skin and other organs produce the symptoms. Damage to small blood vessels within the skin and affected organs also occurs. In the skin, ulceration, calcification, and changes in pigmentation may occur. Systemic features may include fibrosis and degeneration of the heart, lungs, kidneys and gastrointestinal tract.

Patients suffering from scleroderma exhibit certain clinical features, including, blanching, blueness, or redness of fingers and toes in response to heat and cold (Raynaud's phenomenon), pain, stiffness, and swelling of fingers and joints, skin thickening and shiny hands and forearm, esophageal reflux or heartburn, difficulty swallowing, and shortness of breath. Other clinical symptoms used to diagnose scleroderma include, an elevated erythrocyte sedimentation rate (ESR), an elevated rheumatoid factor (RF), a positive antinuclear antibody test, urinalysis that shows protein and microscopic blood, a chest X-ray that may show fibrosis, and pulmonary function studies that show restrictive lung disease.

11. Nail Disorders

The formulations and methods of the invention may be used to treat subjects having a nail disorder. Nail disorders include any abnormality of the nail. Specific nail disorders include, but are not limited to, pitting, koilonychia, Beau's lines, spoon nails, onycholysis, yellow nails, pterygium (seen in lichen planus), and leukonychia. Pitting is characterized by the presence of small depressions on the nail surface. Ridges or linear elevations can develop along the nail occurring in a "lengthwise" or "crosswise" direction. Beau's lines are linear depressions that occur "crosswise" (transverse) in the fingernail. Leukonychia describes white streaks or spots on the nails. Koilonychia is an abnormal shape of the fingernail where the nail has raised ridges and is thin and concave Koilonychia is often associated with iron deficiency.

Nail disorders which can be treated with the TNFalpha antibody of the invention also include psoriatic nails. Psoriatic nails include changes in nails which are attributable to psoriasis. In some instances psoriasis may occur only in the nails and nowhere else on the body. Psoriatic changes in nails range from mild to severe, generally reflecting the extent of psoriatic involvement of the nail plate, nail matrix, i.e., tissue from which the nail grows, nail bed, i.e., tissue under the nail, and skin at the base of the nail. Damage to the nail bed by the pustular type of psoriasis can result in loss of the nail. Nail changes in psoriasis fall into general categories that may occur singly or all together. In one category of psoriatic nails, the nail plate is deeply pitted, probably due to defects in nail growth caused by psoriasis. IN another category, the nail has a yellow to yellow-pink discoloration, probably due to psoriatic involvement of the nail bed. A third subtype of psoriatic nails are characterized by white areas which appear under the nail plate. The white areas are actually air bubbles marking spots where the nail plate is becoming detached from the nail bed. There may also be reddened skin around the nail. A fourth category is evidenced by the nail plate crumbling in yellowish patches, i.e., onychodystrophy, probably due to psoriatic involvement in the nail matrix. A fifth category is characterized by the loss of the nail in its entirety due to psoriatic involvement of the nail matrix and nail bed.

The formulations and methods of the invention may also be used to treat nail disorders often associated with lichen planus. Nails in subjects with lichen planus often show thinning and surface roughness of the nail plate with longitudinal ridges or pterygium.

The formulations and methods of the invention may be used to treat nail disorders, such as those described herein. Often nail disorders are associated with skin disorders. In one embodiment, the invention includes a method of treatment for nail disorders with a TNFalpha antibody. In another embodiment, the nail disorder is associated with another disorder, including a skin disorder such as psoriasis. In another embodiment, the disorder associated with a nail disorder is arthritis, including psoriatic arthritis.

12. Other Skin and Nail Disorders

The formulations and methods of the invention may be used to treat other skin and nail disorders, such as chronic actinic dermatitis, bullous pemphigoid, and alopecia greata. Chronic actinic dermatitis (CAD) is also referred to as photosensitivity dermatitis/actinic reticuloid syndrome (PD/AR). CAD is a condition in which the skin becomes inflamed, particularly in areas that have been exposed to sunlight or artificial light. Commonly, CAD patients have allergies to certain substances that come into contact with their skin, particularly various flowers, woods, perfumes, sunscreens and rubber compounds. Bullous pemphigoid refers to A skin disorder characterized by the formation of large blisters on the trunk and extremities. Alopecia greata refers to hair loss characterized by round patches of complete baldness in the scalp or beard.

K. Metabolic Disorders

The formulations and methods of the invention may be used to treat a metabolic disease. TNFα has been implicated in the pathophysiology of a wide variety of disorders, including metabolic disorders, such as diabetes and obesity (Spiegelman and Hotamisligil (1993) *Cell* 73:625; Chu et al. (2000) *Int J Obes Relat Metab Disord.* 24:1085; Ishii et al. (2000) *Metabolism.* 49:1616).

Metabolic disorders affect how the body processes substances needed to carry out physiological functions. A number of metabolic disorders of the invention share certain characteristics, i.e. they are associated the insulin resistance, lack of ability to regulate blood sugar, weight gain, and increase in body mass index. Examples of metabolic disorders include diabetes and obesity. Examples of diabetes include type 1 diabetes mellitus, type 2 diabetes mellitus, diabetic neuropathy, peripheral neuropathy, diabetic retinopathy, diabetic ulcerations, retinopathy ulcerations, diabetic macrovasculopathy, and obesity. Examples of metabolic disorders which can be treated with the formulations and methods of the invention are described in more detail below:

1. Diabetes

The formulations and methods of the invention may be used to treat diabetes. Tumor necrosis factor has been implicated in the pathophysiology of diabetes. (see e.g., Navarro J. F., Mora C., Maca, Am J Kidney Dis. 2003 July; 42(1):53-61; Daimon M et al., Diabetes Care. 2003 July; 26(7):2015-20; Zhang M et al., J Tongji Med. Univ. 1999; 19(3):203-5, Barbieri M et al., Am J Hypertens. 2003 July; 16(7):537-43.) For example, TNFα is implicated in the pathophysiology for insulin resistance. It has been found that serum TNF levels in patients with gastrointestinal cancer correlates with insulin resistance (see e.g., McCall, J. et al. *Br. J. Surg.* 1992; 79: 1361-3).

Diabetes includes the two most common types of the disorder, namely type I diabetes and type II diabetes, which both result from the body's inability to regulate insulin. Insulin is a hormone released by the pancreas in response to increased levels of blood sugar (glucose) in the blood.

The term "type 1 diabetes," as used herein, refers to a chronic disease that occurs when the pancreas produces too little insulin to regulate blood sugar levels appropriately. Type 1 diabetes is also referred to as insulin-dependent diabetes mellitus, IDMM, juvenile onset diabetes, and diabetes—type I. Type 1 diabetes represents is the result of a progressive autoimmune destruction of the pancreatic β-cells with subsequent insulin deficiency.

The term "type 2 diabetes," refers to a chronic disease that occurs when the pancreas does not make enough insulin to keep blood glucose levels normal, often because the body does not respond well to the insulin. Type 2 diabetes is also referred to as noninsulin-dependent diabetes mellitus, NDDM, and diabetes—type II Diabetes is can be diagnosed by the administration of a glucose tolerance test. Clinically, diabetes is often divided into several basic categories. Primary examples of these categories include, autoimmune diabetes mellitus, non-insulin-dependent diabetes mellitus (type 1 NDDM), insulin-dependant diabetes mellitus (type 2 IDDM), non-autoimmune diabetes mellitus, non-insulin-dependant diabetes mellitus (type 2 NIDDM), and maturity-onset diabetes of the young (MODY). A further category, often referred to as secondary, refers to diabetes brought about by some identifiable condition which causes or allows a diabetic syndrome to develop. Examples of secondary categories include, diabetes caused by pancreatic disease, hormonal abnormalities, drug- or chemical-induced diabetes, diabetes caused by insulin receptor abnormalities, diabetes associated with genetic syndromes, and diabetes of other causes. (see e.g., Harrison's (1996) 14$^{th}$ ed., New York, McGraw-Hill).

Diabetes manifests itself in the foregoing categories and can cause several complications that are discussed in the following sections. Accordingly, the antibody, or antigen-binding fragment thereof, of the invention can be used to treat diabetes. In one embodiment, the TNFα antibody, or antigen-binding fragment thereof, of the invention is used to treat diabetes associated with the above identified catagores.

Diabetes is aften treated with diet, insulin dosages, and various medications described herein. Accordingly, the formulations of the invention may also be administered in combination with agents commonly used to treat metabolic disorders and pain commonly associated with diabetes.

Diabetes manifests itself in many complications and conditions associated with diabetes, including the following catagories:

a. Diabetic Neuropathy and Peripheral Neuropathy

The formulations and methods of the invention may be used to treat diabetic neuropathy or peripheral neuropathy. Tumor necrosis factor has been implicated in the pathophysiology of diabetic neuropathy and peripheral neuropathy. (See Benjafield et al. (2001) *Diabetes Care*. 24:753; Qiang, X. et al. (1998) *Diabetologia*. 41:1321-6; Pfeiffer et al. (1997) *Horm Metab Res*. 29:111).

The term "neuropathy," also referred to as nerve damage-diabetic, as used herein, refers to a common complication of diabetes in which nerves are damaged as a result of hyperglycemia (high blood sugar levels). A variety of diabetic neuropathies are recognized, such as distal sensorimotror polyneuropathy, focal motor neuropathy, and autonomic neuropathy.

The term "peripheral neuropathy," also known as peripheral neuritis and diabetic neuropathy, as used herein, refers to the failure of the nerves to carry information to and from the brain and spinal cord. Peripheral neuropathy produces symptoms such as pain, loss of sensation, and the inability to control muscles. In some cases, the failure of nerves to control blood vessels, intestinal function, and other organs results in abnormal blood pressure, digestion, and loss of other basic involuntary processes. Peripheral neuropathy may involve damage to a single nerve or nerve group (mononeuropathy) or may affect multiple nerves (polyneuropathy).

Neuropathies that affect small myelinated and unmyelinated fibers of the sympathetic and parasympathetic nerves are known as "peripheral neuropathies." Furthermore, the related disorder of peripheral neuropathy, also known as peripheral neuritis and diabetic neuropathy, refers to the failure of the nerves to carry information to and from the brain and spinal cord. This produces symptoms such as pain, loss of sensation, and the inability to control muscles. In some cases, failure of nerves controlling blood vessels, intestinal function, and other organs results in abnormal blood pressure, digestion, and loss of other basic involuntary processes. Peripheral neuropathy may involve damage to a single nerve or nerve group (mononeuropathy) or may affect multiple nerves (polyneuropathy).

The term "diabetic neuropathy" refers to a common complication of diabetes in which nerves are damaged as a result of hyperglycemia (high blood sugar levels). Diabetic neuropathy is also referred to as neuropathy and nerve damage-diabetic. A variety of diabetic neuropathies are recognized, such as distal sensorimotror polyneuropathy, focal motor neuropathy, and autonomic neuropathy.

b. Diabetic Retinopathy

The formulations and methods of the invention may be used to treat diabetic retinopathy. Tumor necrosis factor has been implicated in the pathophysiology of diabetic retinopthy (Scholz et al. (2003) *Trends Microbiol*. 11:171). The term "diabetic retinopathy" as used herein, refers to progressive damage to the eye's retina caused by long-term diabetes. Diabetic retinopathy, includes proliferative retinopathy. Proliferative neuropathy in turn includes includes neovascularization, pertinal hemmorrhave and retinal detachement.

In advanced retinopathy, small vessels proliferate on the surface of the retina. These blood vessels are fragile, tend to bleed and can cause peretinal hemorrhages. The hemorrhage can obscure vision, and as the hemorrhage is resorbed fibrous tissue forms predisposing to retinal detachments and loss of vision. In addition, diabetic retinopathy includes prolferative retinopathy which includes neovascularization, pertinal hemmorrhave and retinal detachement. Daibetic retinopathy also includes "background retinopathy" which involves changes occurring with the layers of the retina.

c. Diabetic Ulcerations and Retinopathy Ulcerations

The formulations and methods of the invention may be used to treat diabetic ulcerations or retinopathy ulcerations. Tumor necrosis factor has been implicated in the pathophysiology of diabetic ulcerations, (see Lee et al. (2003) *Hum Immunol*. 64:614; Navarro et al. (2003) *Am J Kidney Dis*. 42:53; Daimon et al (2003) *Diabetes Care*. 26:2015; Zhang et al. (1999) *J Tongji Med. Univ*. 19:203; Barbieri et al. (2003) *Am J Hypertens*. 16:537; Venn et al. (1993) *Arthritis Rheum*. 36:819; Westacott et al. (1994) *J Rheumatol*. 21:1710).

The term "diabetic ulcerations," as used herein, refers to an ulcer which results as a complication of diabetes. An ulcer is a crater-like lesion on the skin or mucous membrane caused by an inflammatory, infectious, malignant condition, or metabolic disorder. Typically diabetic ulcers can be found on limbs and extremeties, more typically the feet. These ulcers, caused by diabetic conditions, such as neurapthy and a vacualr insuffciency, can lead to ischemia and poor wound healing. More extensive ulcerations may progress to ostemyelitis. Once ostemyelitis develops, it may be dificulte to eradicate with antibotics alonda nd amputation maybe necessary.

The term "retinopathy ulcerations," as used herein refers to an ulcer which causes or results in damages to the eye and the eye's retina. Retinopathy ulcerations may include conditions such has retinoathic hemmorages.

d. Diabetic Macrovasculopathy

The formulations and methods of the invention may be used to treat diabetic macrovasculopathy. Tumor necrosis factor has been implicated in the pathophysiology of diabetic macrovasculopathy (Devaraj et al. (2000) *Circulation.* 102: 191; Hattori Y et al. (2000) *Cardiovasc Res.* 46:188; Clausell N et al. (1999) *Cardiovasc Pathol.* 8:145). The term "diabetic macrovasculopathy," also referred to as "macrovascular disease," as used herein, refers to a disease of the blood vessels that results from diabetes. Diabetic macrovasculopathy complication occurs when, for example, fat and blood clots build up in the large blood vessels and stick to the vessel walls. Diabetic macrovasculopathies include diseases such as coronary disease, cerebrovascular disease, and peripheral vascular disease, hyperglycaemia and cardiovascular disease, and strokes.

2. Obesity

The formulations and methods of the invention may be used to treat obesity. Tumor necrosis factor has been implicated in the pathophysiology of obesity (see e.g., Pihlajamaki J et al. (2003) *Obes Res.* 11:912; Barbieri et al. (2003) *Am J Hypertens.* 16:537; Tsuda et al. (2003) *J Nutr.* 133:2125). Obesity increases a person's risk of illness and death due to diabetes, stroke, coronary artery disease, hypertension, high cholesterol, and kidney and gallbladder disorders. Obesity may also increase the risk for some types of cancer, and may be a risk factor for the development of osteoarthritis and sleep apnea. Obesity can be treated with the antibody of the invention alone or in combination with other metabolic disorders, including diabetes.

L. Vasculitides

The formulations and methods of the invention may be used to treat a subject having a vasculitis. TNFα has been implicated in the pathophysiology of a variety of vasculitides, (see e.g., Deguchi et al. (1989) *Lancet.* 2:745). As used herein, the term "a vasculitis in which TNFα activity is detrimental" is intended to include vasculitis in which the presence of TNFα in a subject suffering from the disorder has been shown to be or is suspected of being either responsible for the pathophysiology of the disorder or a factor that contributes to a worsening of the disorder. Such disorders may be evidenced, for example, by an increase in the concentration of TNFα in a biological fluid of a subject suffering from the disorder (e.g., an increase in the concentration of TNFα in serum, plasma, synovial fluid, etc. of the subject), which can be detected, for example, using an anti-TNFα antibody as described above.

There are numerous examples of vasculitides in which TNFα activity is detrimental, including Behcet's disease. The use of the formulations and methods of the invention in the treatment of specific vasculitides are discussed further below. In certain embodiments, the antibody, or antibody portion, is administered to the subject in combination with another therapeutic agent, as described below The formulations and methods of the invention be used to treat vasculitis in which TNFα activity is detrimental, wherein inhibition of TNFα activity is expected to alleviate the symptoms and/or progression of the vasculitis or to prevent the vasculitis. Subjects suffering from or at risk of developing vasculitis can be identified through clinical symptoms and tests. For example, subjects with vasculitides often develop antibodies to certain proteins in the cytoplasm of neutrophils, antineutrophil cytoplasmic antibodies (ANCA). Thus, in some instances, vasculitides may be evidenced by tests (e.g., ELISA), which measure ANCA presence.

Vasculitis and its consequences may be the sole manifestation of disease or it may be a secondary component of another primary disease. Vasculitis may be confined to a single organ or it may simultaneously affect several organs. and depending on the syndrome, arteries and veins of all sizes can be affected. Vasculitis can affect any organ in the body.

In vasculitis, the vessel lumen is usually compromised, which is associated with ischemia of the tissues supplied by the involved vessel. The broad range of disorders that may result from this process is due to the fact that any type, size and location of vessel (e.g., artery, vein, arteriole, venule, capillary) can be involved. Vasculitides are generally classified according to the size of the affected vessels, as described below. It should be noted that some small and large vessel vasculitides may involve medium-sized arteries; but large and medium-sized vessel vasculitides do not involve vessels smaller than arteries. Large vessel disease includes, but is not limited to, giant cell arteritis, also known as temporal arteritis or cranial arteritis, polymyalgia rheumatica, and Takayasu's disease or arteritis, which is also known as aortic arch syndrome, young female arteritis and Pulseless disease. Medium vessel disease includes, but is not limited to, classic polyarteritis nodosa and Kawasaki's disease, also known as mucocutaneous lymph node syndrome. Non-limiting examples of small vessel disease are Behcet's Syndrome, Wegner's granulomatosis, microscopic polyangitis, hypersensitivity vasculitis, also known as cutaneous vasculitis, small vessel vasculitis, Henoch-Schonlein purpura, allergic granulamotosis and vasculitis, also known as Churg Strauss syndrome. Other vasculitides include, but are not limited to, isolated central nervous system vasculitis, and thromboangitis obliterans, also known as Buerger's disease. Classic Polyarteritis nodosa (PAN), microscopic PAN, and allergic granulomatosis are also often grouped together and are called the systemic necrotizing vasculitides. A further description of vasculitis is described below:

1. Large Vessel Vasculitis

In one embodiment, the formulations and methods of the invention are used to treat subjects who have large vessel vasculitis. The term "large vessel(s)" as used herein, refers to the aorta and the largest branches directed toward major body regions. Large vessels include, for example, the aorta, and its branches and corresponding veins, e.g., the subclavian artery; the brachiocephalic artery; the common carotid artery; the innonimate vein; internal and external jugular veins; the pulmonary arteries and veins; the venae cavae; the renal arteries and veins; the femoral arteries and veins; and the carotid arteries. Examples of large vessel vasculitides are described below.

a. Giant Cell Arteritis (GCA)

The formulations and methods of the invention may be used to treat giant cell arteritis. Tumor necrosis factor has been implicated in the pathophysiology of giant cell arteritis (Sneller, M. C. (2002) *Cleve. Clin. J. Med.* 69:SII40-3; Schett, G., et al. (2002) *Ann. Rheum. Dis.* 61:463). Giant cell arteritis (GCA), refers to a vasculitis involving inflammation and damage to blood vessels, particularly the large or medium arteries that branch from the external carotid artery of the neck. GCA is also referred to as temporal arteritis or cranial arteritis, and is the most common primary vasculitis in the elderly. It almost exclusively affects individuals over 50 years of age, however, there are well-documented cases of patients 40 years and younger. GCA usually affects extracranial arteries. GCA can affect the branches of the carotid arteries, including the temporal artery. GCA is also a systemic disease which can involve arteries in multiple locations.

Histopathologically, GCA is a panarteritis with inflammatory mononuclear cell infiltrates within the vessel wall with frequent Langhans type giant cell formation. There is proliferation of the intima, granulomatous inflammation and fragmentation of the internal elastic lamina. The pathological findings in organs is the result of ischemia related to the involved vessels.

Patients suffering from GCA exhibit certain clinical symptoms, including fever, headache, anemia and high erythrocyte sedimentation rate (ESR). Other typical indications of GCA include jaw or tongue claudication, scalp tenderness, constitutional symptoms, pale optic disc edema (particularly 'chalky white' disc edema), and vision disturbances. The diagnosis is confirmed by temporal artery biopsy.

b. Polymyalgia Rheumatica

The formulations and methods of the invention may be used to treat polymyalgia rheumatica. Tumor necrosis factor has been implicated in the pathophysiology of polymyalgia rheumatica (Straub, R. H., et al. (2002) *Rheumatology* (Oxford) 41:423; Uddhammar, A., et al. (1998) *Br. J. Rheumatol.* 37:766). Polymyalgia rheumatica refers to a rheumatic disorder that is associated with moderate to severe muscle pain and stiffness in the neck, shoulder, and hip, most noticeable in the morning. IL-6 and IL-1β expression has also been detected in a majority of the circulating monocytes in patients with the polymyalgia rheumatica. Polymyalgia rheumatica may occur independently, or it may coexist with or precede GCA, which is an inflammation of blood vessels.

c. Takayasu's Arteritis

The formulations and methods of the invention may be used to treat Takayasu's arteritis. Tumor necrosis factor has been implicated in the pathophysiology of Takayasu's arteritis (Kobayashi, Y. and Numano, F. (2002) *Intern. Med.* 41:44; Fraga, A. and Medina F. (2002) *Curr. Rheumatol. Rep.* 4:30). Takayasu's arteritis refers to a vasculitis characterized by an inflammmation of the aorta and its major branches. Takayasu's arteritis (also known as Aortic arch syndrome, young female arteritis and Pulseless disease) affects the thoracic and abdominal aorta and its main branches or the pulmonary arteries. Fibrotic thickening of the aortic wall and its branches (e.g., carotid, inominate, and subclavian arteries) can lead to reduction of lumen size of vessels that arise from the aortic arch. This condition also typically affects the renal arteries.

Takayasu's arteritis primarily affects young women, usually aged 20-40 years old, particularly of Asian descent, and may be manifested by malaise, arthralgias and the gradual onset of extremity claudication. Most patients have asymmetrically reduced pulses, usually along with a blood pressure differential in the arms. Coronary and/or renal artery stenosis may occur.

The clinical features of Takayasu's arteritis may be divided into the features of the early inflammatory disease and the features of the later disease. The clinical features of the early inflammatory stage of Takayasu's disease are: malaise, low grade fever, weight loss, myalgia, arthralgia, and erythema multiforme. Later stages of Takayasu's disease are characterised by fibrotic stenosis of arteries and thrombosis. The main resulting clinical features are ischaemic phenomena, e.g. weak and asymmetrical arterial pulses, blood pressure discrepancy between the arms, visual disturbance, e.g. scotomata and hemianopia, other neurological features including vertigo and syncope, hemiparesis or stroke. The clinical features result from ischaemia due to arterial stenosis and thrombosis.

2. Medium Vessel Disease

The formulations and methods of the invention may be used to treat subjects who have medium vessel vasculitis. The term "medium vessel(s)" is used to refer to those blood vessels which are the main visceral arteries. Examples of medium vessels include the mesenteric arteries and veins, the iliac arteries and veins, and the maxillary arteries and veins. Examples of medium vessel vasculitides are described below.

a. Polyarteritis Nodosa

The formulations and methods of the invention may be used to treat polyarteritis nodosa. Tumor necrosis factor has been implicated in the pathophysiology of polyarteritis nodosa (DiGirolamo, N., et al. (1997) *J. Leukoc. Biol.* 61:667). Polyarteritis nodosa, or periarteritis nodosa refers to vasculitis which is a serious blood vessel disease in which small and medium-sized arteries become swollen and damaged because they are attacked by rogue immune cells. Polyarteritis nodosa usually affects adults more frequently than children. It damages the tissues supplied by the affected arteries because they don't receive enough oxygen and nourishment without a proper blood supply.

Symptoms which are exhibited in patients with polyarteritis nodosa generally result from damage to affected organs, often the skin, heart, kidneys, and nervous system. Generalized symptoms of polyarteritis nodosa include fever, fatigue, weakness, loss of appetite, and weight loss. Muscle aches (myalgia) and joint aches (arthralgia) are common. The skin of subjects with polyarteritis nodosa may also show rashes, swelling, ulcers, and lumps (nodular lesions).

Classic PAN (polyarteritis nodosa) is a systemic arteritis of small to medium muscular arteritis in which involvement of renal and visceral arteries is common Abdominal vessels have aneurysms or occlusions in 50% of PAN patients. Classic PAN does not involve the pulmonary arteries although the bronchial vessels may be involved. Granulomas, significant eosinophilia and an allergic diathesis are not part of the syndrome. Although any organ system may be involved, the most common manifestations include peripheral neuropathy, mononeuritis multiplex, intestinal ischemia, renal ischemia, testicular pain and livedo reticularis.

b. Kawasaki's Disease

The formulations and methods of the invention may be used to treat Kawasaki's disease. Tumor necrosis factor has been implicated in the pathophysiology of Kawasaki's disease (Sundel, R. P. (2002) *Curr. Rheumatol. Rep.* 4:474; Gedalia, A. (2002) *Curr. Rheumatol. Rep.* 4:25). Although the cause of Kawasaki's disease is unknown, it is associated with acute inflammation of the coronary arteries, suggesting that the tissue damage associated with this disease may be mediated by proinflammatory agents such as TNFα. Kawasaki's disease refers to a vasculitis that affects the mucus membranes, lymph nodes, lining of the blood vessels, and the heart. Kawasaki's disease is also often referred to as mucocutaneous lymph node syndrome, mucocutaneous lymph node disease, and infantile polyarteritis. Subjects afflicted with Kawasaki's disease develop vasculitis often involving the coronary arteries which can lead to myocarditis and pericarditis. Often as the acute inflammation diminishes, the coronary arteries may develop aneurysm, thrombosis, and lead to myocardial infarction.

Kawasaki's disease is a febrile systemic vasculitis associated with edema in the palms and the soles of the feet, with enlargement of cervical lymph nodes, cracked lips and "strawberry tongue". Although the inflammatory response is found in vessels throughout the body, the most common site of end-organ damage is the coronary arteries. Kawasaki's Disease predominantly affects children under the age of 5. The highest incidence is in Japan but is becoming increasingly recognized in the West and is now the leading cause of acquired heart disease in US children. The most serious complication of Kawasaki disease is coronary arteritis and aneurysm formation that occurs in a third of untreated patients.

3. Small Vessel Disease

The formulations and methods of the invention may be used to treat small vessel disease. In one embodiment, the TNFα antibody of the invention is used to treat subjects who have small vessel vasculitis. The term "small vessel(s)" is used to refer to arterioles, venules and capillaries. Arterioles are arteries that contain only 1 or 2 layers of sooth muscle cells and are terminal to and continuous with the capillary network. Venules carry blood from the capillary network to veins and capillaries connect arterioles and venules. Examples of small vessel vasculitides are described below.

a. Behcet's Disease

The formulations and methods of the invention may be used to treat Behcet's disease. Tumor necrosis factor has been implicated in the pathophysiology of Behcet's disease (Sfikakis, P. P. (2002) *Ann. Rheum. Dis.* 61:ii51-3; Dogan, D. and Farah, C. (2002) *Oftalmologia.* 52:23). Behcet's disease is a chronic disorder that involves inflammation of blood vessels throughout the body. Behcet's disease may also cause various types of skin lesions, arthritis, bowel inflammation, and meningitis (inflammation of the membranes of the brain and spinal cord). As a result of Behcet's disease, the subject with the disorder may have inflammation in tissues and organs throughout the body, including the gastrointestinal tract, central nervous system, vascular system, lungs, and kidneys. Behcet's disease is three times more common in males than females and is more common in the east Mediterranean and Japan.

b. Wegener's Granulomatosis

The formulations and methods of the invention may be used to treat Wegener's granulomatosis. Tumor necrosis factor has been implicated in the pathophysiology of Wegener's granulomatosis (Marquez, J., et al. (2003) *Curr. Rheumatol. Rep.* 5:128; Harman, L. E. and Margo, C. E. (1998) *Surv. Ophthalmol.* 42:458). Wegener's granulomatosis refers to a vasculitis that causes inflammation of blood vessels in the upper respiratory tract (nose, sinuses, ears), lungs, and kidneys. Wegener's granulomatosis is also referred to as midline granulomatosis. Wegener's granulomatosis includes a granulomatous inflammation involving the respiratory tract, and necrotizing vasculitis affecting small to medium-sized vessels. Subjects who have Wegener's granulomatosis often also have arthritis (joint inflammation). Glomerulonephritis may also be present in affected subjects, but virtually any organ may be involved.

c. Churg-Strauss syndrome

The formulations and methods of the invention may be used to treat Churg-Strauss syndrome. Tumor necrosis factor has been implicated in the pathophysiology of Churg-Strauss syndrome (Gross, W. L (2002) *Curr. Opin. Rheumatol.* 14:11; Churg, W. A. (2001) *Mod. Pathol.* 14:1284). Churg-Strauss syndrome refers to a vasculitis that is systemic and shows early manifestation signs of asthma and eosinophilia. Churg-Strauss syndrome is also referred to as allergic granulomatosis and angiitis, and occurs in the setting of allergic rhinitis, asthma and eosinophilia. Sinusitis and pulmonary infiltrates also occur in Churg-Strauss syndrome, primarily affecting the lung and heart. Peripheral neuropathy, coronary arteritis and gastrointestinal involvement are common.

M. Other Diseases

The formulations and methods of the invention may be used to treat various other disorders in which TNFalpha activity is detrimental. Examples of other diseases and disorders in which TNFalpha activity has been implicated in the pathophysiology, and thus which can be treated using an antibody, or antibody portion, of the invention, include inflammatory bone disorders and bone resorption disease (see e.g., Bertolini. D. R., et al. (1986) Nature 319:516-518; Konig, A. et al. (1988) J. Bone Miner. Res. 3:621-627; Lerner, U. H. and Ohlin, A. (1993) J. Bone Miner. Res. 8:147-155; and Shanlar. G. and Stem, P. H. (1993) Bone 14:871-876), hepatitis, including alcoholic hepatitis (see eg., McClain, C. J. and Cohen, D. A. (1989) Hepatology 9:349-351; Felver, M. E., et al. (1990) Alcohol. Clin. Exp. Res. 14:255-259; and Hansen, J., et al. (1994) Hepatology 20:461-474), viral hepatitis (Sheron, N., et al. (1991) J. Hepatol. 12:241-245; and Hussain, M. J., et al. (1994) J. Clin. Pathol. 47:1112-1115), and fulminant hepatitis; coagulation disturbances (see e.g., van der Poll, T., et al. (1990) N. Engl. J. Med. 322:1622-1627; and van der Poll, T., et al. (1991) Prog. Clin. Biol. Res. 367:55-60), burns (see eg., Giroir, B. P., et al. (1994) Am. J. Physiol. 267:H 118-124; and Liu. X. S., et al. (1994) Burns 20:40-44), reperfusion injury (see e.g., Scales. W. E., et al. (1994) Am. J. Physiol. 267:G1122-1127; Serrick, C., et al. (1994) Transplantation 58:1158-1162; and Yao, Y. M., et al. (1995) Resuscitation 29:157-168), keloid formation (see e.g., McCauley, R. L., et al. (1992) J. Clin. Immunol. 12:300-308), scar tissue formation; pyrexia; periodontal disease; obesity and radiation toxicity.

Examples of other disorders that may be treated with the formulations and methods of the invention are described in US20040126372 and U.S. Pat. No. 6,258,562, each of which is incorporated by reference herein.

In one embodiment, the formulation and methods of the invention are used to treat rheumatoid arthritis, psoriatic arthritis, or ankylosing spondylitis. The formulation of the invention comprising an isolated human TNF alpha antibody, or antigen-binding portion thereof, (e.g., adalimumab), may be administered to a human subject according to a dosing scheme and dose amount effective for treating rheumatoid arthritis, psoriatic arthritis, or ankylosing spondylitis. In one embodiment, a dose of about 40 mg of a human TNF alpha antibody, or antigen-binding portion thereof, (e.g., adalimumab) (e.g., 0.4 mL of a 100 mg/mL formulation of the invention) in the formulation of the invention is administered to a human subject every other week for the treatment of rheumatoid arthritis, psoriatic arthritis, or ankylosing spondylitis. In one embodiment, a dose of about 80 mg of a human TNF alpha antibody, or antigen-binding portion thereof, (e.g., adalimumab) (e.g., 0.8 mL of a 100 mg/mL formulation of the invention) in the formulation of the invention is administered to a human subject monthly for the treatment of rheumatoid arthritis, psoriatic arthritis, or ankylosing spondylitis. In one embodiment, the formulation is administered subcutaneously, every other week (also referred to as biweekly, see methods of administration described in US20030235585, incorporated by reference herein) for the treatment of rheumatoid arthritis, ankylosing spondylitis, or psoriatic arthritis. In one embodiment, the formulation is administered subcutaneously, monthly for the treatment of rheumatoid arthritis, ankylosing spondylitis, or psoriatic arthritis.

In one embodiment, the formulation of the invention is used to treat Crohn's disease or ulcerative colitis. The formulation of the invention comprising an isolated human TNF alpha antibody, or antigen-binding portion thereof, (e.g., adalimumab), may be administered to a human subject according to a dosing scheme and dose amount effective for treating Crohn's disease. In one embodiment, a dose of about 160 mg of a human TNF alpha antibody, or antigen-binding portion thereof, (e.g., adalimumab) (e.g., 1.6 mL of a 100 mg/mL formulation of the invention) in the formulation of the invention is administered to a human subject initially at about day 1, followed by a subsequent dose of 80 mg of the antibody (e.g., 0.8 mL of a 100 mg/mL formulation of the invention) two weeks later, followed by administration of about 40 mg (e.g., 0.4 mL of a 100 mg/mL formulation of the invention) every other week for the treatment of Crohn's disease. In one embodiment, the formulation is administered subcutaneously, according to a multiple variable dose regimen comprising an induction dose(s) and maintenance dose(s) (see, for example, U.S. Patent Publication Nos. US20060009385 and US20090317399, incorporated by reference herein) for the treatment of Crohn's disease or ulcerative colitis, each of which are incorporated by reference herein) for the treatment of Crohn's disease or ulcerative colitis. In one embodiment, the formulation is administered subcutaneously, biweekly or monthly for the treatment of Crohn's disease or ulcerative colitis. In one embodiment, a dose of about 80 mg of a human TNF alpha antibody, or antigen-binding portion thereof, (e.g., adalimumab) (e.g., 0.8 mL of a 100 mg/mL formulation of the invention) in the formulation of the invention is administered to a human subject monthly for the treatment of Crohn's disease or ulcerative colitis.

In one embodiment, the formulation of the invention is used to treat psoriasis. The formulation of the invention comprising an isolated human TNF alpha antibody, or antigen-binding portion thereof, (e.g., adalimumab), may be administered to a human subject according to a dosing scheme and dose amount effective for treating psoriasis. In one embodiment, an initial dose of about 80 mg of a human TNF alpha antibody, or antigen-binding portion thereof, (e.g., adalimumab) (e.g., 0.8 mL of a 100 mg/mL formulation of the invention) in the formulation of the invention is administered to a human subject, followed by a subsequent dose of 40 mg of the antibody (e.g., 0.4 mL of a 100 mg/mL formulation of the invention) every other week starting one week after the initial dose. In one embodiment, the formulation is administered subcutaneously, according to a multiple variable dose regimen comprising an induction dose(s) and maintenance dose(s) (see, for example, US 20060009385 and WO 2007/120823, each of which are incorporated by reference herein) for the treatment of psoriasis In one embodiment, the formulation is administered subcutaneously, biweekly or monthly for the treatment of psoriasis. In one embodiment, a dose of about 80 mg of a human TNF alpha antibody, or antigen-binding portion thereof, (e.g., adalimumab) (e.g., 0.8 mL of a 100 mg/mL formulation of the invention) in the formulation of the invention is administered to a human subject monthly for the treatment of psoriasis.

In one embodiment, the formulation of the invention is used to treat juvenile idiopathic arthritis (JIA). The formulation of the invention comprising an isolated human TNF alpha antibody, or antigen-binding portion thereof, (e.g., adalimumab), may be administered to a human subject according to a dosing scheme and dose amount effective for treating JIA. In one embodiment, 20 mg of a human TNF alpha antibody, or antigen-binding portion thereof, in the formulation of the invention (e.g., 0.2 mL of a 100 mg/mL formulation of the invention) is administered to a subject weighing 15 kg (about 33 lbs) to less than 30 kg (66 lbs) every other week for the treatment of JIA. In another embodiment, 40 mg of a human TNF alpha antibody, or antigen-binding portion thereof, in the formulation of the invention (e.g., 0.4 mL of a 100 mg/mL formulation of the invention) is administered to a subject weighing more than or equal to 30 kg (66 lbs) every other week for the treatment of JIA. In one embodiment, the formulation is administered subcutaneously, according to a weight-based fixed dose (see, for example, U.S. Patent Publication No. 20090271164, incorporated by reference herein) for the treatment of JIA. In one embodiment, the formulation is administered subcutaneously biweekly or monthly for the treatment of JIA In one embodiment, an isolated human TNF alpha antibody, or antigen-binding portion thereof, (e.g., adalimumab), may be administered to a human subject for treatment of a disorder associated with detrimental TNFa activity according to a monthly dosing schedule, whereby the antibody is administered once every month or once every four weeks. As described above, examples of disorders that may be treated according to a monthly dosing schedule using the formulations and methods of the invention include, but are not limited to, rheumatoid arthritis, ankylosing spondylitis, JIA, psoriasis, Crohn's disease, ulcerative colitis, hidradenitis suppurativa, giant cell arteritis, Behcet's disease, sarcoidosis, diabetic retinopathy, or psoriatic arthritis. Thus, the formulation of the invention comprising an isolated human TNF alpha antibody, or antigen-binding portion thereof, (e.g., adalimumab), may be administered to a human subject for treatment of a disorder associated with detrimental TNFa activity according to a monthly dosing schedule. In one embodiment, 80 mg of a human TNF alpha antibody, or antigen-binding portion thereof, in the formulation of the invention (e.g., 0.8 mL of a 100 mg/mL formulation of the invention) is administered to a subject having a disorder associated with detrimental TNFa activity. In one embodiment, 80 mg of a human TNF alpha antibody, or antigen-binding portion thereof, in the formulation of the invention (e.g., 0.8 mL of a 100 mg/mL formulation of the invention) is administered monthly or biweekly to a subject for the treatment of a disorder associated with detrimental TNFa activity.

Dose amounts described herein may be delivered as a single dose (e.g., a single dose of 40 mg in 0.4 mL or 80 mg dose in 0.8 mL), or, alternatively may be delivered as multiple doses (e.g., four 40 mg doses or two 80 mg doses for delivery of a 160 mg dose).

The formulation of the invention comprising an isolated human TNF alpha antibody, or antigen-binding portion thereof, (e.g., adalimumab) may also be administered to a subject in combination with an additional therapeutic agent. In one embodiment, the formulation is administered to a human subject for treatment of rheumatoid arthritis in combination with methotrexate or other disease-modifying anti-rheumatic drugs (DMARDs). In another embodiment, the formulation is administered to a human subject for treatment of JIA in combination with methotrexate or other disease-modifying anti-rheumatic drugs (DMARDs). Additional combination therapies are described in U.S. Pat. Nos. 6,258,562 and 7,541,031; and U.S. Patent Publication No. US20040126372, the entire contents of all of which are incorporated by reference herein.

The formulation of the invention comprising a human TNF alpha antibody, or antigen-binding portion thereof, may also be used to treat a subject who has failed previous TNF inhibitor therapy, e.g., a subject who has lost response to or is intolerant to infliximab.

The invention is further illustrated in the following examples, which should not be construed as further limiting.

EXAMPLES

Example 1

High Concentration Anti-TNFα Antibody Formulation Reduces Injection Pain

There have been reports of pain associated with the subcutaneous administration of a human anti-TNFα antibody, e.g., adalimumab. In placebo-controlled trials, 20% of patients treated with adalimumab developed injection site reactions (erythema and/or itching, haemorrhage, pain or swelling), compared to 14% of patients receiving placebo. Most injection site reactions are mild and do not generally necessitate drug discontinuation.

There are two main components of the injection pain associated with adalimumab: the pain associated with the needle stick, and the pain associated with the injection of drug into the tissue. The injection-related pain may be related to the Adalimumab formulation and/or to the volume of medication. The following study examined whether various formulations have an impact on injection pain following subcutaneous delivery of adalimumab.

Materials and Methods
Study Design

The primary objectives of this study were to compare injection-related pain of three high concentration (100 mg/mL) adalimumab formulations in the PHYSIOLIS™ pre-filled syringe with the current (50 mg/mL) adalimumab commercial formulation in the current pre-filled syringe; and to assess the bioavailability of three high concentration (100 mg/mL) adalimumab formulations in comparison to the current (50 mg/mL) adalimumab commercial formulation. The secondary objective of this study was to assess the safety and tolerability of all four adalimumab formulations.

200 healthy adult male and female subjects who fulfilled the study eligibility criteria were recruited to participate in the study. Generally, the study was conducted according to a randomized parallel-group design. Pain assessment data was preferably obtained from all 200 subjects. Evaluation of pharmacokinetics (PK) was done only for the first 100 or so subjects.

Subjects from each treatment group were scheduled to receive one subcutaneous injection of adalimumab 40 mg via a pre-filled syringe. There were four treatment groups, one for each of the four formulations as set forth in Table 1 below. After meeting the selection criteria, subjects were randomly assigned in roughly equal numbers to one of the four treatment groups shown in Table 1.

The three high concentration formulations (F1, F3, and F4), each contained 40 mg of adalimumab in 0.4 mL of solution in the PHYSIOLIS™ pre-filled syringe. F1, F3, and F4 were compared to the current adalimumab commercial formulation of 40 mg of adalimumab in 0.8 mL of solution in the current pre-filled syringe. The ingredients for each of the formulations is described below in Table 1. The formulations described in Table 1 also refer to the formulations described in Examples 2-7 below.

TABLE 1

| Treatment Groups | | | |
|---|---|---|---|
| Treatment Group | No. of Subjects | Study Day 1 SC Injection | Formulation |
| A | 50 | High Conc. Formulation 1 (F1) (40 mg/0.4 mL in the PHYSIOLIS ™ pre-filled syringe) | adalimumab, Mannitol, Citric acid monohydrate, Sodium citrate, Disodium phosphate dihydrate, Polysorbate 80, Water for injection, Sodium Hydroxide added as necessary to adjust pH. |
| B | 50 | High Conc. Formulation 3 (F3) (40 mg/0.4 mL in the PHYSIOLIS ™ pre-filled syringe) | adalimumab, Mannitol, Polysorbate 80, Water for injection |
| C | 50 | High Conc. Formulation 4 (F4) (40 mg/0.4 mL in the PHYSIOLIS ™ pre-filled syringe) | adalimumab, Polysorbate 80, Water for injection |
| D | 50 | Current Commercial Formulation (40 mg/0.8 mL in the current pre-filled syringe) | adalimumab, Mannitol, Citric acid monohydrate, Sodium citrate, Disodium phosphate dihydrate, Sodium dihydrogen phosphate dihydrate, Sodium chloride, Polysorbate 80, Water for injection, Sodium Hydroxide added as necessary to adjust pH |

The first about 100 subjects to fulfill all entry criteria and enroll in the study were randomized to the four treatment groups in roughly equal numbers in each group and participated as either Cohort 1 or Cohort 2. The second about 100 subjects to fulfill all entry criteria and enroll in the study were randomized to the four treatment groups, in roughly equal numbers in each group, and participated as Cohorts 3-5. It is the Cohort number that specifies if a subject has pharmacokinetic (PK) and pain assessments or only pain assessments as described in Table 2 below.

TABLE 2

| Assignment of Study Subjects | | | | | | |
|---|---|---|---|---|---|---|
| | Total | | No. of Subjects | | | |
| Cohort | N | Assessments | A | B | C | D |
| 1 | 50 | PK and Pain | 13 | 12 | 13 | 12 |
| 2 | 44 | PK and Pain | 11 | 12 | 10 | 11 |
| 3 | 38 | Pain | 9 | 9 | 10 | 10 |
| 4 | 39 | Pain | 10 | 10 | 10 | 9 |
| 5 | 29 | Pain | 7 | 7 | 7 | 8 |

Pharmacokinetic sample collection and pain assessments was done for all subjects in the first two cohorts of about 100 patients (Cohorts 1 and 2). Subjects in Cohorts 3-5 only participated in pain assessments, and no pharmacokinetic samples were be collected for these subjects. Safety and tolerability were to be assessed in all subjects of all 5 cohorts. Each subject was randomly assigned to receive one injection of adalimumab on Study Day 1. Each dose of study drug was to be administered subcutaneously by an appropriate site staff member via a pre-filled syringe in accordance with the proper injection method. The injection was given subcutaneously in the abdomen 2 inches to the right of the navel. Questionnaires were administered by a different study staff member than the individual administering the injection, as often as possible.

Subjects in Cohorts 1 and 2 (pharmacokinetic and pain assessments) were confined to the study site and supervised for approximately 10 days (9 nights). Confinement for each subject began on Study Day—1 (1 day prior to the dosing day) and ended after the collection of the 192 hour blood samples and scheduled study procedures on Study Day 9. Serial blood samples were collected through Study Day 57 after dosing with subjects returning for outpatient visits. Safety and tolerability were assessed throughout the study. Subjects in Cohorts 3-5 (pain assessments only) were confined to the study site and supervised for approximately 3 days (2 nights). Confinement for each subject began on Study Day—1 (1 day prior to the dosing day) and ended after the completed study procedures on Study Day 2. Safety and tolerability were assessed throughout the study.

In addition to bioavailability and AAA assays, tolerability was preferably assessed as follows:

1) Immediately following the injection on Study Day 1: Pain Assessment Module was completed by the subject.

2) Approximately 10 minutes following the injection on Study Day 1: Draize Scale (hemorrhage, petechiae, erythema, edema, and pruritus) was evaluated by a qualified site staff member.

3) Approximately 15 minutes following the injection on Study Day 1: Pain Assessment Module was completed by the subject.

4) Approximately 30 minutes following the injection on Study Day 1: Pain Assessment Module and Draize Scale evaluation was completed by the subject and a qualified site staff member, respectively.

The demographics of subjects in the treatment groups are as follows, shown in Table 3, below.

TABLE 3

Patient Demographics

| Variable | High Conc. Formulation 1 (N = 50) | High Conc. Formulation 3 (N = 50) | High Conc. Formulation 4 (N = 50) | Commercial Formulation (N = 50) |
|---|---|---|---|---|
| Age (yrs) | 29.6 ± 8.7 | 29.5 ± 9.4 | 30.0 ± 8.9 | 30.3 ± 9.7 |
| Weight (kg) | 68.3 ± 13.9 | 69.6 ± 9.6 | 67.0 ± 8.4 | 68.5 ± 10.0 |
| Sex | 31 F (62%), 19 M (38%) | 25 F (50%), 25 M (50%) | 31 F (62%), 19 M (38%) | 30 F (60%), 20 M (40%) |
| Race | 37 white (74%), 9 black (18%), 4 other (8%) | 45 white (90%), 3 black (6%), 2 other (4%) | 36 white (72%), 10 black (20%), 4 other (8%) | 40 white (80%), 8 black (16%), 2 other (4%) |

Formulations

Three new high concentration formulations (referred to herein as Formulation 1, 3, or 4; or F1, F3, or F4, respectively) were studied relative to the commercial 50 mg/mL adalimumab formulation. The compositions of each of these formulations are listed below in Tables 4-7.

TABLE 4

Formulation 1 (F1)
COMPOSITION OF THE BULK SOLUTION
1 mL bulk solution contains

| Name of ingredient | Concentration [mg] |
|---|---|
| Active Substance | |
| adalimumab (A-765865)* | 100.00 |
| Excipients | |
| Mannitol | 42.00 |
| Citric acid monohydrate | 1.31 |
| Sodium citrate | 0.31 |

TABLE 4-continued

Formulation 1 (F1)
COMPOSITION OF THE BULK SOLUTION
1 mL bulk solution contains

| Name of ingredient | Concentration [mg] |
|---|---|
| Disodium phosphate dihydrate | 1.53 |
| Sodium dihydrogen phosphate dihydrate | 0.86 |
| Polysorbate 80 | 1.00 |
| Sodium Hydroxide | q.s. |
| Water for injections | ad 1,041.00 |
| Nitrogen | — |

Density of the solution: 1.041 g/mL
*Used as concentrate.

TABLE 5

Formulation 3 (F3)
COMPOSITION OF THE BULK SOLUTION
1 mL bulk solution contains

| Name of ingredient | Concentration [mg] |
|---|---|
| Active Substance | |
| adalimumab (A-765865)* | 100 |

TABLE 5-continued

Formulation 3 (F3)
COMPOSITION OF THE BULK SOLUTION
1 mL bulk solution contains

| Name of ingredient | Concentration [mg] |
|---|---|
| Excipients | |
| Mannitol | 42.00 |
| Polysorbate 80 | 1.00 |
| Water for injections | ad 1,040.00 |
| Nitrogen | — |

*Used as concentrate.
Density of the solution: 1.040 g/mL

TABLE 6

Formulation 4 (F4)
COMPOSITION OF THE BULK SOLUTION
1 mL bulk solution contains

| Name of ingredient | Concentration [mg] |
|---|---|
| Active Substance | |
| adalimumab (A-765865)* | 100.00 |
| Excipients | |
| Polysorbate 80 | 1.00 |
| Water for injections | ad 1,026.00 |
| Nitrogen | — |

*Used as concentrate.
Density of the solution: 1.026 g/mL

TABLE 7

Commercial 50 mg/mL adalimumab formulation
COMPOSITION OF THE BULK SOLUTION
1 mL bulk solution contains

| Name of ingredient | Concentration [mg] |
|---|---|
| Active Substance | |
| adalimumab (A-765865)* | 50.00 |
| Excipients | |
| Mannitol | 12.00 |
| Citric acid monohydrate | 1.30 |
| Sodium citrate | 0.30 |
| Disodium phosphate dihydrate | 1.53 |
| Sodium dihydrogen phosphate dihydrate | 0.86 |
| Polysorbate 80 | 1.00 |
| Sodium Hydroxide | q.s. |
| Water for injections | ad about 1,000 |
| Sodium Chloride | 6.16 |
| Nitrogen | — |

Study Drug Administration

Study drug (adalimumab) in the various formulations was administered in the morning at Hour 0 on Study Day 1. The four treatment groups are set forth in Table 1 above as Groups A, B, C and D. Subjects in each treatment group were subcutaneously injected with only a single adalimumab formulation via a pre-filled syringe.

Two types of syringes were used in this study; the currently commercially available glass pre-filled syringe ("current pre-filled syringe") was used for the reference current adalimumab commercial formulation (40 mg of adalimumab in 0.8 mL of solution), and the PHYSIOLIS™ pre-filled syringe for the three high concentration test formulations (40 mg of adalimumab in 0.4 mL of solution). The PHYSIOLIS™ pre-filled syringe has a 29 gauge needle (the current pre-filled syringe has a 27 gauge ½ inch length fixed needle), a latex-free needle shield, and a plunger stopper which is coated to minimize leachables.

Pain Testing: Pain Scale

The Pain Visual Analog Scale was used to quantitatively assess pain sensation. The following instructions were followed to assess the Pain Visual Analog Scale (VAS):

The pain scale was administered to the subject at three different times after the injection: immediately after the injection, at 15 minutes after the injection, and at 30 minutes after the injection on Study Day 1. The pain scale was shown and read to the subject, who was asked to place one straight vertical mark along the line in the pain scale to indicate their current level of pain at the injection site (for example see below). An indication of 0 meant no pain, while the highest score (10) indicated "the worst imaginable pain." An illustrative pain scale used in the study is shown below:

What is your current level of pain at the injection site?
0                                           10
no pain                    the worst imaginable pain Qualitative Assessment of Pain Following the completion of the pain scale, the qualitative assessment of pain was administered three times after the injection: immediately following the injection, at 15 minutes post the injection, and 30 minutes following the injection on Study Day 1. An exemplary qualitative assessment of pain used in the study is shown below:
Select all that describe your current level of pain at the injection site:
Shooting pain
Sharp pain
Stinging Pain
Dull
Uncomfortable
Pressure
Aching
Soreness
Localized burning
Other
OR
I currently have no discomfort at my injection site
Needle Pain Assessment After the qualitative assessment of pain was completed, a needle pain assessment was administered immediately following the injection. An exemplary needle pain assessment used in the study is shown below:
Were you able to tell the difference between the pain from the needle entering your skin and the pain from the solution that was injected?
Yes
No
a. If yes, was most of your pain caused by the needle entering your skin or was most of your pain caused by the solution that was injected?
Most of my pain was caused by the needle entry
Most of my pain was caused by the solution that was injected
Draize Scale Qualified site personnel completed this assessment for each subject approximately 10 minutes and 30 minutes after the injection on Study Day 1.
Hemorrhage/Petechiae at Injection Site:
  0: None
  1: Isolated; up to 5 petechiae
  2: Isolated but >5 petechiae
  3: Many petechiae, some coalescence
  4: Spots of blood on surface
  5: Frank bleeding
Erythema at Injection Site:
  0: No erythema
  1: Very slight (barely perceptible) erythema
  2: Well-defined erythema
  3: Moderate to severe erythema
  4: Severe erythema (beet redness)
Edema at Injection Site:
  0: No edema
  1: Very slight (barely perceptible) edema 2: Slight edema (edges of area well defined by slight raising)
3: Moderate edema (raised ~1 mm)
4: Severe edema (raised>1 mm, extending beyond area of injection)
Pruritis at Injection Site:
  0: No pruritis
  1: Occasional pruritis
  2: Constant pruritis
Results To determine whether delivery of adalimumab could be improved, new high concentration formulations were developed. Formulations F1, F3, and F4, as shown below, have half of the volume (i.e., 0.4 mL vs. 0.8 mL) and twice the protein concentration (100 mg/mL vs. 50 mg/mL) compared to the current commercial adalimumab formulation, and they also have different excipient compositions. Experiments described herein were designed to assess whether any of the new formulations are superior to the current commercial adalimumab formulation.

The pain visual analog scale was chosen to assess injection site pain, and was used to evaluate impact of formulation composition on pain sensations. In addition, tolerability of various new adalimumab 100 mg/mL formulations were compared to the current commercial formulation (50 mg/mL adalimumab formulation). Data in this example supports the surprising finding that the new formulations, especially Formulation 3 (F3), decreases pain significantly relative to the current commercial formulation. Surprisingly, F3 also decreased pain significantly relative to formulations F1 and F4.

Specifically, FIG. 1 shows that administration of high concentration Formulations 1 and 3 resulted in a significant decrease in pain assessment at all time points after injection (immediately, 15 minutes, and 30 minutes), compared to the other treatment groups (F4 and the current commercial formulation). Table 8, shown below, summarizes the individual data and shows a comparison of the F1, F3, and F4 formulations with the 0.8 mL, 50 mg/mL commercial formulation.

As described in Table 8, immediately after injection, subjects who received the current Humira formulation reported a mean (SD) pain score of 3.29 (2.57) cm. The mean pain scores for Formulation 1 and Formulation 3 were statistically significantly lower than that for the current Humira formulation ($p<0.001$). The estimated differences from the current Humira formulation were −1.50 (95% CI: −2.31--0.69 cm) for Formulation F1, and −2.70 (95% CI: −3.52--1.89 cm) for Formulation F3. Thus, Treatments A and B (high concentration Formulations 1 and 3) resulted in 45.6% and 82.7% reductions in injection site pain, respectively. Statistical tests were not performed for the pain scores assessed at 15 minutes and 30 minutes after injection because a majority of the subjects reported no pain at these time points. As described in FIG. 1, the minimum/maximum VAS scores immediately after injection were as follows: Formulation F1, 0.00-8.3; Formulation F3, 0.00-2.20; Formulation F4, 0.20-8.70; and current commercial formulation, 0.00-10.00.

It was apparent that the pain associated with the injection of Formulation 3 was dramatically reduced compared to the same for the current commercial formulation. Specifically, mean pain value, as assessed by the pain visual analog scale (VAS) immediately after injection, decreased from a mean of 3.29 in the current commercial formulation to 0.56 in Formulation 3, a stark 83% reduction. In fact, the pain reduction associated with Formulation 3 was so significant, it was 69% reduced from the level of the next best formulation (in terms of pain)—Formulation 1 (1.79).

Similarly, the mean pain scale for Formulation 1 reduced to 1.79, a 45% reduction from the 3.29 pain scale associated with the current commercial formulation.

TABLE 8

Pain Visual Analog Scales (VAS) Immediately After Injection

| Treatment | N | Mean (SD) | LS Mean& | Comparisons with Current Formulation& | | |
|---|---|---|---|---|---|---|
| | | | | Estimate | P-value# | 95% CI |
| High Conc. Formulation 1 | 50 | 1.79 (2.08) | 1.79 | −1.50 | <0.001 | −2.31, −0.69 |
| High Conc. Formulation 3 | 50 | 0.56 (0.56) | 0.58 | −2.71 | <0.001 | −3.52, −1.90 |
| High Conc. Formulation 4 | 50 | 4.12 (2.50) | 4.11 | 0.82 | 0.976 | 0.01, 1.63 |
| Current Formulation | 50 | 3.29 (2.57) | 3.29 | | | |

From a one-sided test with the null hypothesis being that the mean for the test formulation is ≥ the mean for the current formulation
&Based on ANOVA.

A Qualitative Assessment of Pain was also administered to subjects immediately after injection, 15 minutes after injection and at 30 minutes after injection for all four adalimumab treatments. Immediately after injection, an assessment of "no discomfort" was reported with greatest frequency by 31 subjects (31/50, 62.0%) who had received Formulation 3, followed by 19 subjects (19/50, 38.0%) who had received Formulation 1, 7 subjects (7/50, 14.0%) who had received the current Humira formulation, and one subject (1/50, 2.0%) who had received Formulation 4. Of those subjects who reported discomfort immediately after injection, "stinging pain" was the most frequently reported sensation with 30 subjects (30/50, 60%) for each of the current formulation and formulation 4, 16 subjects (16/50, 32.0%) for Formulation 1, and 4 subjects (4/50, 8.0%) for Formulation 3. At 15 minutes after injection, a large majority of subjects receiving each treatment reported "no discomfort" at the injection site.

Study site staff also utilized the Draize Scale to evaluate hemorrhage/petechiae, erythema, edema and pruritis at the injection site of each subject. Ten minutes after injection the majority of subjects in all treatment groups had no observed injection-site hemorrhages or petechiae, edema or pruritis.

All four formulations were well tolerated during the study. A summary of preliminary adverse events (AE) data is shown below in Table 9.

TABLE 9

Preliminary Adverse Events (AE)

| | High Conc. Formulation 1 (N = 50) | High Conc. Formulation 3 (N = 50) | High Conc. Formulation 4 (N = 50) | Current Formulation (N = 50) |
|---|---|---|---|---|
| Any AE | 7 (14%) | 7 (14%) | 6 (12%) | 3 (6%) |
| Any AE at least possibly drug related | 3 (6%) | 3 (6%) | 2 (4%) | 1 (2%) |
| Any severe AE | 0 | 0 | 0 | 0 |
| Any serious AE | 0 | 0 | 0 | 0 |
| Any AE leading to study discontinuation | 0 | 0 | 0 | 0 |
| Deaths | 0 | 0 | 0 | 0 |

Accordingly, the data demonstrates that the new 100 mg/mL formulations, especially formulations 1 and 3, are well tolerated, and were effective in reducing injection site pain after subcutaneous injection of similar therapeutic doses as compared to the currently marketed adalimumab formulation. Formulation F3 had a particularly low VAS score relative to the other formulations tested.

The reduction in pain using the VAS score was not related to the difference in needle size (a 27G needle was used to administer the current adalimumab commercial formulation and a 29G needle was used to administer formulations F1, F3, and F4). In particular, a needle prick accounts for an immediate pain response, whereas the pain response measured by the VAS scale indicated a prolonged persistent pain over several minutes, demonstrating that the injected solution itself contributes to the majority of the response. In addition, all of the test formulations (F1, F3, and F4) were injected using the same size needle, yet F1, F3, and F4 had very different VAS scores. This result further demonstrates that it was the formulation contributing to the pain effect, and that this can be separated from the size of the needle used to administer the formulations.

Example 2

High Concentration Anti-TNFa Antibody Formulations Increase Bioavailability in Humans The following example describes a Phase 1, single-blind, single-dose, parallel-group design, randomized study in healthy volunteers (same study described above in Example 1). The primary objectives of this study were to compare injection-related pain of three high concentration (100 mg/mL) adalimumab formulations in the Physiolis PFS with the current (50 mg/mL) adalimumab (Humira) formulation in the current PFS (see Example 1), and to assess the bioavailability of three high concentration (100 mg/mL) adalimumab formulations in comparison to the current commercial (50 mg/mL) adalimumab (Humira) formulation. The secondary objective of this study was to assess the safety and tolerability of all four adalimumab formulations.

Study Design

Two hundred healthy volunteers were enrolled in this study (Table 10). Pain assessment data were obtained from all 200 subjects. Adalimumab pharmacokinetics were evaluated in the first 100 subjects. A description of the formulations is provided above in Table 1.

TABLE 10

Treatment Groups

| Treatment Group | Number of Subjects for Study | Number of Subjects for Pharmacokinetic Data | Study Day 1 SC Injection |
|---|---|---|---|
| A | 50 | 24 | High Concentration Adalimumab Formulation No. 1 (40 mg/0.4 mL in the Physiolis PFS) |
| B | 50 | 24 | High Concentration Adalimumab Formulation No. 3 (40 mg/0.4 mL in the Physiolis PFS) |
| C | 50 | 23 | High Concentration Adalimumab Formulation No. 4 (40 mg/0.4 mL in the Physiolis PFS) |
| D | 50 | 23 | Current Commercial Humira Formulation (40 mg/0.8 mL in the current PFS) |

*See Tables 4-7 for formulation compositions.

Subjects from each treatment group received one subcutaneous injection of 40 mg adalimumab via PFS on Study Day 1. Each dose of study drug was administered subcutaneously by an appropriate site staff member in accordance with the proper injection method as described in the protocol. The injection was given subcutaneously in the abdomen 2 inches to the right of the navel. Questionnaires were administered by a different study staff member than the individual administering the injection, as often as possible.

Results

Pharmacokinetic Results and Conclusions

Figure 2:
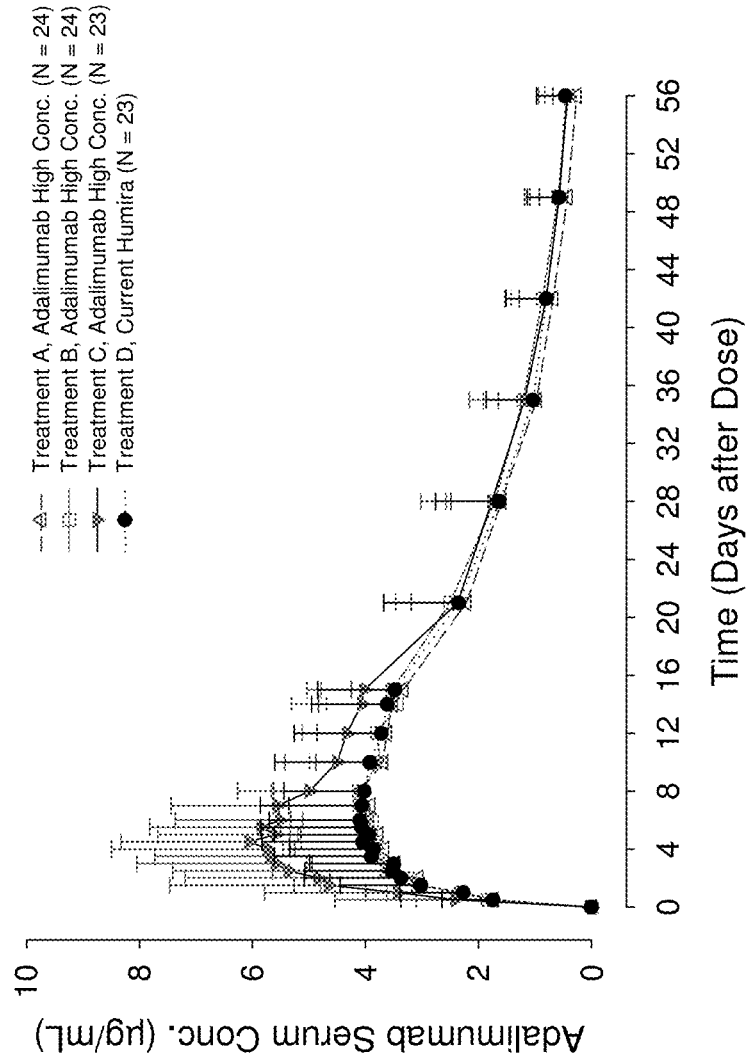
FIG. 2 shows, on a linear scale, the means and standard deviations of adalimumab serum concentrations over a time period of 56 days following a single 40 mg SC dose of adalimumab.

Following a single subcutaneous dose of adalimumab, the central values of the pharmacokinetic parameters, $T_{max}$, $C_{max}$, $AUC_{0-360}$ and $AUC_{0-1344}$ were similar between Treatments A, B (high concentration adalimumab Formulations 1 and 3, respectively) and D (current commercial Humira formulation). Following the single dose administration, mean $T_{max}$ was earlier for Treatment C (high concentration adalimumab Formulation 4) relative to Treatment D (FIGS. 2 and 3). The central values of $C_{max}$ and $AUC_{0-360}$ values were greater ($p<0.05$) for Treatment C versus Treatment D.

Bioavailability/Bioequivalence for Treatments A, B and C (Adalimumab High Concentration Formulations) Relative to Treatment D (Commercial Humira Formulation)

For Treatment Group A versus D, the point estimates for the ratios of $C_{max}$, $AUC_{0-360}$, and $AUC_{0-1344}$ central values for Treatments A and B were near unity, and the 90% confidence intervals were within the 0.80 to 1.25 range. For Treatment B versus D, the point estimates for the ratios of $C_{max}$ and $AUC_{0-360}$ central values were near unity and the 90% confidence intervals were within the 0.80 to 1.25 range. For $AUC_{0-1344}$, the upper bound of the 90% confidence interval for Treatments B versus D was above 1.25. For Treatment C versus D, the point estimates for the ratio of $C_{max}$, $AUC_{0-360}$ and $AUC_{0-1344}$ central values were 1.429, 1.309, and 1.170 respectively, indicating that the relative bioavailability of Treatment C (Formulation 4) was greater.

TABLE 11

Relative Bioavailability and 90% Confidence Intervals for the Bioequivalence Assessment

| Treatments[£] Test vs. Reference | PK Parameter | Central Value Test | Central Value Reference | Point Estimate | Relative Bioavailability 90% Confidence Interval |
|---|---|---|---|---|---|
| A vs. D | $C_{max}$ | 4.47 | 4.39 | 1.018 | 0.859-1.207 |
|  | $AUC_{0-360}$ | 1192.14 | 1192.23 | 1.000 | 0.860-1.163 |
|  | $AUC_{0-1344}$ | 2306.91 | 2387.28 | 0.966 | 0.814-1.147 |
| B vs. D | $C_{max}$ | 4.52 | 4.39 | 1.029 | 0.868-1.219 |
|  | $AUC_{0-360}$ | 1222.24 | 1192.23 | 1.025 | 0.882-1.192 |
|  | $AUC_{0-1344}$ | 2547.95 | 2387.28 | 1.067 | 0.899-1.266 |

TABLE 11-continued

Relative Bioavailability and 90% Confidence
Intervals for the Bioequivalence Assessment

| Treatments[£] Test vs. Reference | PK Parameter | Central Value Test | Central Value Reference | Relative Bioavailability Point Estimate | 90% Confidence Interval |
|---|---|---|---|---|---|
| C vs. D | $C_{max}$ | 6.28 | 4.39 | 1.429 | 1.202-1.699 |
|  | $AUC_{0-360}$ | 1561.05 | 1192.23 | 1.309 | 1.123-1.527 |
|  | $AUC_{0-1344}$ | 2794.29 | 2387.28 | 1.170 | 0.983-1.394 |

[£]Treatments A, B or C: a single dose of high concentration adalimumab Formulation 1, 3 or 4, respectively, administered as a single sc injection using a Physiolis PFS (40 mg/0.4 mL). Treatment D: a single dose of the current Humira formulation administered as a single sc injection using the currently available glass PFS (40 mg/0.8 mL).
PK = Pharmacokinetic.

Pharmacokinetic Conclusions

Based on the pharmacokinetic results, the relative bioavailability of Treatments A and B were similar to Treatment D, the currently marketed Humira formulation. The relative bioavailability of Treatment C was greater when compared to Treatment D. The unexpected increase in bioavailability for Treatment C suggests that the effective dose amount administered to a subject may be reduced.

Immunogenicity Conclusions

Twelve subjects had positive AAA samples during any time in the study, with only two subjects determined as AAA positive according to the pre defined definition. Because of the small sample size and relatively similar numbers of AAA positive samples, no conclusions can be made of the immunogenicity between the treatments.

Safety Conclusions

The treatments tested were generally well tolerated by the subjects. No clinically significant vital signs, ECG or laboratory measurements were observed during the course of the study. The majority of adverse events were assessed by the investigator as probably not or not related to study drug and mild in severity. No adverse events were assessed as severe.

No deaths, serious adverse events or discontinuations due to adverse events occurred during the study.

Results of other safety analyses, including individual subject changes and potentially clinically significant values for vital signs, ECG and laboratory measurements, were unremarkable for all treatment groups.

Tolerability

The tolerability assessments that were conducted included completion of a Pain Assessment Module (Pain Visual Analog Scale [VAS]), Qualitative Assessment of Pain and Needle Pain Assessment) and the Draize Scale (see Example 1).

Example 3

High Concentration Anti-TNFa Antibody Formulation Increase Bioavailability in Pre-Clinical Model The objective of the following study was to evaluate the pharmacokinetic profiles of adalimumab formulation F4 in contrast to the adalimumab commercial formulation (see Table 7 above for a description of the formulation).

The pharmacokinetic profiles of HUMIRA (Adalimumab) were studied in male and female Beagle dogs (2/sex/s.c. administration and 2 males/i.v. administration, Marshall Bio Resources USA, Inc., North Rose, N.Y. 14516) after a single subcutaneous (s.c.) injection of the HUMIRA commercial formulation (adalimumab) and a HUMIRA test formulation corresponding to formulation F4 of the previous examples (adalimumab), as well as an intravenous (i.v.) injection of the HUMIRA commercial formulation as a control. The administered dose was 40 mg/dog (at 100 mg/mL for F4 and 50 mg/mL of the commercial formulation).

For the determination of Adalimumab serum exposure levels, blood samples were collected at 0.083, 4, 24, 48, 96, 168, 240, 312, 384, 456, 528 and 864 hours post administration (p.a.). Examined parameters were clinical signs (twice weekly) and mortality.

Apart from mucous feces in one male animal of the control group, no relevant clinical signs were observed. The incidences of clinical signs are summarized in Tables 14 and 15 below.

The pharmacokinetic results (described in Table 12 below) of this study indicated that the bioavailability after s.c. dosing was about 80% and the exposure levels seemed to be higher in females than in males after s.c. dosing. There was a trend for higher exposure levels following s.c. dosing of the test formulation compared with s.c. dosing of the commercial formulation in males.

TABLE 12

Pharmacokinetic results

| Treatment | Gender | Animal Number | $AUC_{0-528\,h}$ (µg*Hours/mL) | AUC/Dose (µg*Hours/mL/mg/kg) | Vdss (mL) | $T_{1/2}$ (Hours) |
|---|---|---|---|---|---|---|
| Test formulation, s.c. | male | 1001 | 9020 | 226 | 708 | 39.3 |
|  |  | 1003 | 11400 | 286 | 870 | 187.2 |
|  |  | Mean | 10200 ± 1680 | 256 ± 42.4 | 789 ± 115 | 113.3 ± 104.6 |
|  | female | 1002 | 15400 | 384 | 388 | 55.5 |
|  |  | 1004 | 15800 | 395 | 469 | 54.5 |
|  |  | Mean | 15600 ± 283 | 390 ± 7.78 | 429 ± 57.3 | 55 ± 0.7 |
| Commercial formulation, s.c. | male | 2001 | 8010 | 200 | 692 | 21.4 |
|  |  | 2003 | 8230 | 206 | 695 | 72.7 |
|  |  | Mean | 8120 ± 156 | 203 ± 4.24 | 694 ± 2.12 | 47.1 ± 36.3 |
|  | female | 2002 | 12700 | 319 | 385 | 34.0 |
|  |  | 2004 | 17200 | 431 | 477 | 119.0 |
|  |  | Mean | 15000 ± 3180 | 375 ± 79.2 | 431 ± 65.1 | 76.5 ± 60.1 |
| Commercial formulation, i.v. | male | 3001 | 9360 | 234 | 548 | 45.5 |
|  |  | 3003 | 11900 | 298 | 407 | 22.2 |
|  |  | Mean | 10600 ± 1800 | 266 ± 45.3 | 478 ± 99.7 | 33.9 ± 16.5 |

TABLE 13

Animal identification

| Animal No. | Tattoo-No. | Sex |
|---|---|---|
| 1001 | 1246730 | Male |
| 1003 | 1230230 | Male |
| 1002 | 1282302 | Female |
| 1004 | 1288688 | Female |
| 2001 | 1284879 | Male |
| 2003 | 1298951 | Male |
| 2002 | 1297237 | Female |
| 2004 | 1280491 | Female |
| 3001 | 1285514 | Male |
| 3003 | 1290143 | Male |

TABLE 14

Summary of Clinical Observations in Males

| Dosage Group: | 2 | | 3 | | 1 | |
|---|---|---|---|---|---|---|
| Animals Examined: | 4 | | 4 | | 2 | |
| Number Normal: | 3 | | 3 | | 2 | |
| Category, Observation | a | b | a | b | a | b |
| Excretion, feces | 1 | 4 | 0 | 0 | | |

Note:
a = Number of animals with observation
b = Number of days observation seen

TABLE 15

Summary of Clinical Observations in Females

| Dosage Group: | 2 | 3 | 1 |
|---|---|---|---|
| Animals Examined: | 2 | 2 | 2 |
| Number Normal: | 2 | 2 | 2 |
| Category, Observation | | | |

Note:
a = Number of animals with observation
b = Number of days observation seen

Example 4

Stability of High Concentration Anti-TNFa Antibody Formulations Against Freeze/Thaw Stress The following example compares the stability of high concentration formulations F1, F3, and F4 with the commercial adalimumab formulation. Stability was examined using freeze/thaw tests.

Experimental Setup

High concentration human anti-TNFα antibody formulations were prepared as described in Example 1, Table 1 above.

The compounded solutions were sterile filtered and aliquoted in 8×30 mL PETG bottles at 20 mL, respectively. The solutions were practically free from particles in visual inspection.

The samples for T0 were directly placed into a 2-8° C. refrigerator. The other bottles were put into the −80° C. cube to freeze.

The next day the bottles were thawed in water baths with a temperature of 25° C. or 37° C., respectively.

The Freeze/Thaw cycles were repeated 5 times. At T0 (before any freeze-thaw cycles), T1 (after one freeze-thaw cycle), T3 (after three freeze-thaw cycles) and T5 (after five freeze-thaw cycles) samples were taken for analysis and stored in a 2-8° C. fridge.

→n=1 per pullpoint from 4 samples
→Sample volume: 20 mL
→Freeze/Thaw: −80° C./25° C.+37° C.
→Freeze/thaw cycles: 5

After the cycling the samples were analyzed in the lab using each of the following measures: Optical appearance (at each time point); absorption at 340 nm; subvisible particles (at GGDDA); Photon-correlation-spectroscopy (PCS); Size Exclusion Chromatography (SEC); and Ion Exchange Chromatography (IEC).

Subvisible Particles

The measurement of subvisible particles was made at the Klotz particle measurement device. The results are shown in Table 16.

TABLE 16

Counts of particles >=1 μm, >=10 μm, and >=25 μm

| Timepoint | Sample | Temperature | Charge | Particles >= 1 μm | 10 μm | 25 μm |
|---|---|---|---|---|---|---|
| T0 | HC F1 | (25° C.) | E161118001CL | 9 | 1 | 0 |
| T0 | HC F1 | (37° C.) | E161118001CL | 7 | 2 | 1 |
| T1 | HC F1 | 25° C. | E161118001CL | 3 | 0 | 0 |
| T1 | HC F1 | 37° C. | E161118001CL | 33 | 1 | 0 |
| T3 | HC F1 | 25° C. | E161118001CL | 3 | 0 | 0 |
| T3 | HC F1 | 37° C. | E161118001CL | 20 | 1 | 0 |
| T5 | HC F1 | 25° C. | E161118001CL | 4 | 0 | 0 |
| T5 | HC F1 | 37° C. | E161118001CL | 94 | 0 | 0 |
| T0 | HC F3 | (25° C.) | E161119001CL | 6 | 3 | 1 |
| T0 | HC F3 | (37° C.) | E161119001CL | 12 | 2 | 0 |
| T1 | HC F3 | 25° C. | E161119001CL | 4 | 1 | 0 |
| T1 | HC F3 | 37° C. | E161119001CL | 7 | 2 | 0 |
| T3 | HC F3 | 25° C. | E161119001CL | 3 | 1 | 0 |
| T3 | HC F3 | 37° C. | E161119001CL | 9 | 2 | 1 |
| T5 | HC F3 | 25° C. | E161119001CL | 7 | 0 | 0 |
| T5 | HC F3 | 37° C. | E161119001CL | 5 | 0 | 0 |
| T0 | HC F4 | (25° C.) | E161120001CL | 5 | 1 | 1 |
| T0 | HC F4 | (37° C.) | E161120001CL | 7 | 1 | 0 |
| T1 | HC F4 | 25° C. | E161120001CL | 6 | 1 | 0 |
| T1 | HC F4 | 37° C. | E161120001CL | 5 | 1 | 0 |
| T3 | HC F4 | 25° C. | E161120001CL | 12 | 1 | 1 |

TABLE 16-continued

Counts of particles >=1 μm, >=10 μm, and >=25 μm

| Timepoint | Sample | Temperature | Charge | Particles >= 1 μm | 10 μm | 25 μm |
|---|---|---|---|---|---|---|
| T3 | HC F4 | 37° C. | E161120001CL | 60 | 0 | 0 |
| T5 | HC F4 | 25° C. | E161120001CL | 13 | 0 | 0 |
| T5 | HC F4 | 37° C. | E161120001CL | 22 | 1 | 0 |
| T0 | commercial | (25° C.) | E161121001CL | 464 | 2 | 1 |
| T0 | commercial | (37° C.) | E161121001CL | 198 | 0 | 0 |
| T1 | commercial | 25° C. | E161121001CL | 143 | 1 | 0 |
| T1 | commercial | 37° C. | E161121001CL | 285 | 0 | 0 |
| T3 | commercial | 25° C. | E161121001CL | 108 | 0 | 0 |
| T3 | commercial | 37° C. | E161121001CL | 224 | 0 | 0 |
| T5 | commercial | 25° C. | E161121001CL | 39 | 0 | 0 |
| T5 | commercial | 37° C. | E161121001CL | 151 | 0 | 0 |

The >=1 μm particle data showed a clear trend to a higher particle load in Humira commercial and high concentration (HC) F1 at T5, reflecting a characteristic behavior of buffer salt or sodium chloride containing adalimumab formulations.

| Sample name | Sum Aggregates | Monomer | Sum Fragments |
|---|---|---|---|
| T0, HC F1, 25° C. | 0.42 | 99.50 | 0.09 |
| T0, HC F1, 37° C. | 0.43 | 99.46 | 0.11 |
| T0, HC F3, 25° C. | 0.39 | 99.54 | 0.07 |
| T0, HC F3, 37° C. | 0.41 | 99.50 | 0.09 |
| T0, HC F4, 25° C. | 0.43 | 99.46 | 0.11 |
| T0, HC F4, 37° C. | 0.42 | 99.48 | 0.11 |
| T0, commercial, 25° C. | 0.36 | 99.55 | 0.09 |
| T0, commercial, 37° C. | 0.35 | 99.56 | 0.09 |
| T1, HC F1, 25° C. | 0.43 | 99.47 | 0.10 |
| T1, HC F1, 37° C. | 0.44 | 99.48 | 0.08 |
| T1, HC F3, 25° C. | 0.38 | 99.53 | 0.09 |
| T1, HC F3, 37° C. | 0.37 | 99.54 | 0.09 |
| T1, HC F4, 25° C. | 0.44 | 99.47 | 0.09 |
| T1, HC F4, 37° C. | 0.44 | 99.46 | 0.10 |
| T1, commercial, 25° C. | 0.35 | 99.56 | 0.08 |
| T1, commercial, 37° C. | 0.35 | 99.56 | 0.10 |
| T3, HC F1, 25° C. | 0.42 | 99.47 | 0.10 |
| T3, HC F1, 37° C. | 0.42 | 99.48 | 0.11 |
| T3, HC F3, 25° C. | 0.40 | 99.48 | 0.12 |
| T3, HC F3, 37° C. | 0.40 | 99.52 | 0.08 |
| T3, HC F4, 25° C. | 0.48 | 99.41 | 0.11 |
| T3, HC F4, 37° C. | 0.44 | 99.48 | 0.08 |
| T3, commercial, 25° C. | 0.36 | 99.54 | 0.10 |
| T3, commercial, 37° C. | 0.34 | 99.55 | 0.11 |
| T5, HC F1, 25° C. | 0.43 | 99.48 | 0.09 |
| T5, HC F1, 37° C. | 0.45 | 99.45 | 0.10 |
| T5, HC F3, 25° C. | 0.41 | 99.48 | 0.11 |
| T5, HC F3, 37° C. | 0.39 | 99.48 | 0.13 |
| T5, HC F4, 25° C. | 0.47 | 99.43 | 0.10 |
| T5, HC F4, 37° C. | 0.49 | 99.40 | 0.11 |
| T5, commercial, 25° C. | 0.36 | 99.56 | 0.08 |
| T5, commercial, 37° C. | 0.40 | 99.47 | 0.13 |

Subvisible particle counts for >=10 μm and >=25 both were very low. Freeze/thaw cycling did not lead to an increased number of subvisible particles, indicating that the tested formulations had favorable stability.

Size Exclusion Chromatography (SEC)

The SEC results are shown in Table 17. Table 17 indicates the percentages of SEC aggregates, monomers, and fragments in each of the solutions at T0 (before any freeze-thaw cycles), T1 (after one freeze-thaw cycle), T3 (after three freeze-thaw cycles) and T5 (after five freeze-thaw cycles). These results indicate that each of formulations 1, 3, and 4 show stabilities similar to that of the commercial formulation.

Table 17: Percentages of Aggregates, Monomers, and Fragments Before and after Freeze-Thaw Cycles as Assessed by SEC Ion Exchange Chromatography (IEC)

Ion exchange chromatography did not reveal different sensitivity of the tested solutions. No significant degradation could be observed.

However, with increasing number of freeze/thaw cycles, the samples that were thawed at 25° C. showed a higher amount in the 2nd acidic region after 5 cycles.

IEC results are shown in Table 18.

TABLE 18

IEC measurements before and after freeze-thaw cycles

| Sample name | Sum Lysin Peaks | 1.ac area | 2.ac area | Lysin 0 | Lysin 1 | Peak between | Lysin 2 |
|---|---|---|---|---|---|---|---|
| T0, HC F1, 25° C. | 86.74 | 2.09 | 10.51 | 68.63 | 16.72 | 0.99 | 0.40 |
| T0, HC F3, 25° C. | 87.29 | 1.89 | 10.22 | 66.35 | 16.16 | 0.91 | 3.87 |
| T0, HC F4, 25° C. | 87.35 | 1.85 | 10.20 | 66.46 | 16.15 | 0.89 | 3.85 |
| T0, commercial, 25° C. | 87.18 | 1.93 | 10.22 | 66.25 | 16.12 | 0.94 | 3.88 |
| T1, HC F1, 25° C. | 87.17 | 1.98 | 10.18 | 66.24 | 16.11 | 0.94 | 3.87 |
| T1, HC F3, 25° C. | 87.30 | 1.81 | 10.24 | 66.39 | 16.13 | 0.90 | 3.88 |
| T1, HC F4, 25° C. | 87.21 | 1.88 | 10.25 | 66.31 | 16.11 | 0.90 | 3.88 |
| T1, commercial, 25° C. | 87.19 | 2.01 | 10.20 | 66.27 | 16.11 | 0.93 | 3.88 |
| T3, HC F1, 25° C. | 87.23 | 1.94 | 10.20 | 66.34 | 16.12 | 0.91 | 3.87 |
| T3, HC F3, 25° C. | 87.27 | 1.86 | 10.25 | 66.37 | 16.14 | 0.88 | 3.88 |

TABLE 18-continued

IEC measurements before and after freeze-thaw cycles

| Sample name | Sum Lysin Peaks | 1.ac area | 2.ac area | Lysin 0 | Lysin 1 | Peak between | Lysin 2 |
|---|---|---|---|---|---|---|---|
| T3, HC F4, 25° C. | 87.26 | 1.82 | 10.27 | 66.34 | 16.15 | 0.88 | 3.88 |
| T3, commercial, 25° C. | 87.20 | 1.88 | 10.28 | 66.29 | 16.11 | 0.91 | 3.89 |
| T5, HC F1, 25° C. | 87.39 | 1.74 | 10.21 | 66.43 | 16.18 | 0.89 | 3.88 |
| T5, HC F3, 25° C. | 87.27 | 1.79 | 10.32 | 66.42 | 16.15 | 0.84 | 3.86 |
| T5, HC F4, 25° C. | 87.33 | 1.69 | 10.32 | 66.49 | 16.14 | 0.85 | 3.85 |
| T5, commercial, 25° C. | 87.05 | 1.95 | 10.38 | 66.17 | 16.10 | 0.89 | 3.88 |
| T0, HC F1, 37° C. | 87.25 | 1.94 | 10.19 | 66.36 | 16.13 | 0.90 | 3.86 |
| T0, HC F3, 37° C. | 87.42 | 1.82 | 10.19 | 66.54 | 16.16 | 0.85 | 3.87 |
| T0, HC F4, 37° C. | 87.38 | 1.89 | 10.11 | 66.52 | 16.14 | 0.86 | 3.86 |
| T0, commercial, 37° C. | 87.25 | 1.86 | 10.24 | 66.34 | 16.12 | 0.91 | 3.88 |
| T1, HC F1, 37° C. | 87.21 | 1.98 | 10.17 | 66.27 | 16.11 | 0.95 | 3.88 |
| T1, HC F3, 37° C. | 87.32 | 1.91 | 10.12 | 66.40 | 16.13 | 0.90 | 3.88 |
| T1, HC F4, 37° C. | 87.27 | 1.98 | 10.13 | 66.36 | 16.14 | 0.91 | 3.86 |
| T1, commercial, 37° C. | 87.28 | 1.97 | 10.14 | 66.34 | 16.12 | 0.93 | 3.88 |
| T3, HC F1, 37° C. | 87.27 | 1.95 | 10.15 | 66.36 | 16.11 | 0.94 | 3.86 |
| T3, HC F3, 37° C. | 87.18 | 2.03 | 10.11 | 66.29 | 16.13 | 0.90 | 3.87 |
| T3, HC F4, 37° C. | 87.21 | 1.95 | 10.15 | 66.35 | 16.09 | 0.92 | 3.85 |
| T3, commercial, 37° C. | 87.31 | 1.95 | 10.21 | 66.50 | 16.09 | 0.91 | 3.81 |
| T5, HC F1, 37° C. | 87.29 | 2.01 | 10.06 | 66.40 | 16.11 | 0.93 | 3.85 |
| T5, HC F3, 37° C. | 87.25 | 2.07 | 10.06 | 66.37 | 16.10 | 0.92 | 3.87 |
| T5, HC F4, 37° C. | 87.28 | 2.04 | 10.02 | 66.42 | 16.11 | 0.93 | 3.83 |
| T5, commercial, 37° C. | 87.53 | 1.91 | 10.02 | 66.72 | 16.11 | 0.88 | 3.83 |

Example 5

Stability of High Concentration Anti-TNFa Antibody Formulations Against Stir Stress The following example describes a study which examined the stability of the F1, F3, and F4 formulations using the stir-stress test. Each formulation was tested in a range of pH levels.

Materials

| Humira HC F1 100 mg/mL | pH 4.2 |
| | pH 4.7 |
| | pH 5.7 |
| | pH 6.2 |
| Humira HC F3 100 mg/mL | pH 4.2 |
| | pH 4.7 |
| | pH 5.7 |
| | pH 6.2 |
| Humira HC F4 100 mg/mL | pH 4.2 |
| | pH 4.7 |
| | pH 5.7 |
| | pH 6.2 |

Procedure

The vials, stir bars, and stoppers were steam sterilized prior to use.

The stirring experiment was performed with the following experimental set-up:

Protein solutions: Humira HC F1, F3, F4, each at pH 4.2, 4.7, 5.7, 6.2 100 mg/mL, Humira HC F3 pH 5.2 100 mg/mL, Humira from Vetter 50 mg/mL, 5 mL filling volume per 6R vial n=3→2× stirred (with 7×2 mm magnetic bar), 1 unstirred control (without magnetic bar)

magnetic stirrer multipoint HP: 550 rpm ambient temperature sample pull: t=0, t=1 h, t=4 h, t=24 h, t=48 h Three 6R vials were filled with 5 mL for each protein solution and closed with stoppers. Two of them were equipped with a magnetic stir bar.

The vials were kept at 5° C. over night. The next morning the samples (one per protein solution, because in the beginning they were all the same) were measured with the turbidity meter. The measured solutions were filled back in the vials prior start of the experiment. After 1, 4, 24, and 48 h samples were taken and the turbidity was determined The unstirred samples were only measured at the time points 0 and 48 h.

For Humira HC F3 pH 5.2 also subvisible particles were determined for all time points.

Results

Turbidity

The turbidity results for samples subjected to stir stress for 0, 1, 4, 24, or 48 hours, as well as a 48 hour unstirred control, are shown in Table 19.

TABLE 19

Turbidity (NTU) of samples subjected to stir stress

| sample | 0 h | 1 h | 4 h | 24 h | 48 h |
|---|---|---|---|---|---|
| Commercial Adalimumab | 20.90 | 23.90 | 31.20 | 98.05 | 176.00 |
| Humira HC F3 pH 5.2 | 6.13 | 6.69 | 8.92 | 18.05 | 29.50 |
| Humira HC F1 4.2 | 8.62 | 8.89 | 9.40 | 6.48 | 15.05 |
| Humira HC F1 4.7 | 14.00 | 15.50 | 20.05 | 10.88 | 81.40 |
| Humira HC F1 5.7 | 30.70 | 33.25 | 36.40 | 23.40 | 100.40 |
| Humira HC F1 6.2 | 38.00 | 40.95 | 52.60 | 32.65 | 168.00 |
| Humira HC F3 4.2 | 3.20 | 3.35 | 3.72 | 4.88 | 6.69 |
| Humira HC F3 4.7 | 4.81 | 5.20 | 6.09 | 9.54 | 18.70 |
| Humira HC F3 5.7 | 8.75 | 10.03 | 11.30 | 25.90 | 46.10 |

TABLE 19-continued

Turbidity (NTU) of samples subjected to stir stress

| sample | 0 h | 1 h | 4 h | 24 h | 48 h |
|---|---|---|---|---|---|
| Humira HC F3 6.2 | 9.24 | — | 13.05 | 22.60 | 37.30 |
| Humira HC F4 4.2 | 3.44 | 3.74 | 3.80 | 6.48 | 9.79 |
| Humira HC F4 4.7 | 5.13 | 5.67 | 6.60 | 10.88 | 17.00 |
| Humira HC F4 5.7 | 9.23 | 10.15 | 12.50 | 23.40 | 32.20 |
| Humira HC F4 6.2 | 10.30 | 11.65 | 15.55 | 32.65 | 56.75 |

Increased pH correlated with increased turbidity for all tested formulations, both T0/unstirred and stirred samples. This effect was most pronounced for formulation 1. Also, formulation 1 showed the highest increase of turbidity after 48 h at all pH values except 4.2. Formulation 3 and 4 showed similar behavior and turbidity values were comparable at all time points.

Humira HC (100 mg/mL), F3, pH 5.2 showed only a slight increase of the turbidity over the time. In contrast, the commercial Humira solution showed both a significantly higher starting value and increase in turbidity over the time. Thus, formulation 3 showed lower turbidity than the commercial Humira formulation.

The stirred samples showed a higher turbidity compared with the unstirred controls. The turbidity of the unstirred controls remained almost constant in comparison to the 0 h samples, indicating that running the experiment at room temperature did not bias the results.

Subvisible Particles

Table 20 shows the results for the numbers of subvisible particles.

TABLE 20

Counts of subvisible particles before and after stirring stress

| | subvisible particles | | |
|---|---|---|---|
| Humira HC F3 pH 5.2 | >=1 µm | >=10 µm | >=25 µm |
| 0 h | 103 | 3 | 1 |
| 1 h | 194 | 4 | 0 |
| 4 h | 202 | 4 | 0 |
| 24 h | 262 | 2 | 0 |
| 48 h | 192 | 3 | 0 |
| 48 h unstirred | 80 | 1 | 0 |

Particles≥1 µm
Stirring induced a slight increase in sub-visible particle counts 1 µm. The unstirred control was comparable to the 0 h sample.

Particles≥10 µm
Stirring had no significant effect on the particle counts≥10 µm. The unstirred control was comparable to the 0 h sample.

Particles≥25 µm
Stirring had no significant effect on the particle counts 25 µm. The unstirred control was comparable to the 0 h sample.

Overall, the results of the experiments presented in Example 5 showed that formulation 3, when subjected to stirring stress, was surprisingly stable compared with commercial Humira solution. Formulation 3 was robust to stirring stress according to the turbidity measure, and stirring of formulation 3 also had little or no effect on formation of subvisible particles.

Example 6

Long-Term Storage Stability of High Concentration Anti-TNFa Antibody

The following example describes a study which examined the long-term storage stability (up to 24 months) of the F1, F3, and F4 formulations.

Formulations Ft, F3, and F4 were tested prior to long term storage (Initial), and after 3, 6, 9, 12, 18, and 24 months of storage. The following storage conditions were used: (1) 5° C., (2) 25° C./60% relative humidity (R.H), and (3) 40° C./75% R.H. During storage, the samples were packaged in a 1 ml pre-filled syringe (colorless, glass type I, Ph. Eur.); BD Hypak Syringe BD 260 with a grey DB Hypak 4023/50 Fluorotec stopper. The following measures were used to assess storage stability:particulate contamination: visible particles; clarity and opalescence; color of solution (visual); in vitro TNFα-neutralization; cation exchange chromatography (CEX-HPLC), size exclusion chromatography (SE-HPLC); particulate contamination-sub-visible particles; container closure integrity; pH; and microbial quality.

All formulations tested were stable under the tested storage conditions of 2-8° C. for up Results The results for Formulation F1 are presented in Table 21.

TABLE 21

Stability Summary Report for Formulation F1

| | | | | Storage Conditions [° C./% r.H.] | | |
|---|---|---|---|---|---|---|
| \\Test Item | Component | Specification | Duration of Testing | 5° C. | 25° C./ 60% R.H. | 40° C./ 75% R.H. |
| Participate contamination: visible particles | Visible particles | NMT 4.5 | Initial | 0.0 | 0.0 | 0.0 |
| | | | 3 months | 0.0 | 0.0 | 0.0 |
| | | | 6 months | 0.0 | 0.1 | 0.0 |
| | | | 9 months | 0.0 | — | — |
| | | | 12 months | 0.0 | — | — |
| | | | 18 months | 0.0 | — | — |
| | | | 24 months | 0.0 | — | — |
| Clarity and Opalescence | Assessment | Not more opalescent than reference suspension IV | Initial | <=RS III | <=RS III | <=RS III |
| | | | 3 months | <=RS III | <=RS III | <=RS IV |
| | | | 6 months | <=RS III | <=RS III | <=RS IV |
| | | | 9 months | <=RS IV | — | — |
| | | | 12 months | <=RS III | — | — |
| | | | 18 months | <=RS III | — | — |
| | | | 24 months | <=RS III | — | — |

TABLE 21-continued

Stability Summary Report for Formulation F1

| \Test Item | Component | Specification | Duration of Testing | Storage Conditions [° C./% r.H.] | | |
|---|---|---|---|---|---|---|
| | | | | 5° C. | 25° C./ 60% R.H. | 40° C./ 75% R.H. |
| Color of solution (visual) | BY-Scale | Report value | Initial | <=BY 7 | <=BY 7 | <=BY 7 |
| | | | 3 months | <=BY 7 | <=BY 7 | <=BY 7 |
| | | | 6 months | <=BY 7 | <=BY 7 | <=BY 6 |
| | | | 9 months | <=BY 7 | — | — |
| | | | 12 months | <=BY 7 | — | — |
| | | | 18 months | <=BY 7 | — | — |
| | | | 24 months | <=BY 7 | — | — |
| In vitro TNF-Neutralization | (cytotoxicity test) [%] | 80% to 125% of the neutralization capacity of the reference standard | Initial | 99 | 99 | 99 |
| | | | 3 months | 97 | 110 | 97 |
| | | | 6 months | 87 | 81 | 68 |
| | | | 9 months | 88 | — | — |
| | | | 12 months | 110 | — | — |
| | | | 18 months | 97 | — | — |
| | | | 24 months | 111 | — | — |
| | Fiducial Limit of error (p = 0.95) lower Limit [%] | NLT 64 | Initial | 96.1 | 96.1 | 96.1 |
| | | | 3 months | 91.1 | 104.7 | 93.2 |
| | | | 6 months | 84.2 | 76.3 | 64.4 |
| | | | 9 months | 84.3 | — | — |
| | | | 12 months | 105.2 | — | — |
| | | | 18 months | 95.3 | — | — |
| | | | 24 months | 108.9 | — | — |
| | Fiducial Limit of error (p = 0.95) upper Limit [%] | NMT 156 | Initial | 101.3 | 101.3 | 101.3 |
| | | | 3 months | 101.9 | 115.5 | 100.1 |
| | | | 6 months | 90.8 | 85.9 | 71.2 |
| | | | 9 months | 90.8 | — | — |
| | | | 12 months | 114.2 | — | — |
| | | | 18 months | 98.8 | — | — |
| | | | 24 months | 113.5 | — | — |
| Cation Exchange Chromatography (CEX-HPLC) | Sum of lysine variants [%] | NLT 75 | Initial | 86.8 | 86.8 | 86.8 |
| | | | 3 months | 86.2 | 74.7 | 26.0 |
| | | | 6 months | 85.9 | 65.0 | 11.9 |
| | | | 9 months | 85.2 | — | — |
| | | | 12 months | 85.2 | — | — |
| | | | 18 months | 84.1 | — | — |
| | | | 24 months | 83.9 | — | — |
| Size exclusion chromatography (SE-HPLC) | Principal peak (monomer) [%] | NLT 98 | Initial | 99.6 | 99.6 | 99.6 |
| | | | 3 months | 99.5 | 99.0 | 96.4 |
| | | | 6 months | 99.4 | 98.5 | 92.9 |
| | | | 9 months | 99.4 | — | — |
| | | | 12 months | 99.4 | — | — |
| | | | 18 months | 99.3 | — | — |
| | | | 24 months | 99.3 | — | — |
| Particulate contamination - Sub-visible Particles* | Particles >=10 μm [/container] | NMT 6000 | Initial | 11 | 11 | 11 |
| | | | 3 months | 8 | 37 | 55 |
| | | | 6 months | 33 | 102 | 98 |
| | | | 9 months | 32 | — | — |
| | | | 12 months | 58 | — | — |
| | | | 18 months | 44 | — | — |
| | | | 24 months | 11 | — | — |
| | Particles >=25 μm [/container] | NMT 600 | Initial | 0 | 0 | 0 |
| | | | 3 months | 0 | 0 | 1 |
| | | | 6 months | 0 | 2 | 2 |
| | | | 9 months | 0 | — | — |
| | | | 12 months | 0 | — | — |
| | | | 18 months | 1 | — | — |
| | | | 24 months | 0 | — | — |
| Container Closure Integrity | Assessment | Tight | Initial | Complies | Complies | Complies |
| | | | 6 months | Complies | Complies | Complies |
| | | | 12 months | Complies | — | — |
| | | | 18 months | Complies | — | — |
| | | | 24 months | Complies | — | — |
| pH | Single values | 4.7 to 5.7 | Initial | 5.3 | 5.3 | 5.3 |
| | | | 3 months | 5.2 | 5.2 | 5.2 |
| | | | 6 months | 5.3 | 5.3 | 5.3 |
| | | | 9 months | 5.3 | — | — |
| | | | 12 months | 5.3 | — | — |
| | | | 18 months | 5.3 | — | — |
| | | | 24 months | 5.3 | — | — |

TABLE 21-continued

Stability Summary Report for Formulation F1

| Test Item | Component | Specification | Duration of Testing | Storage Conditions [° C./% r.H.] | | |
|---|---|---|---|---|---|---|
| | | | | 5° C. | 25° C./ 60% R.H. | 40° C./ 75% R.H. |
| Microbial quality | Sterility drug product | No evidence of microbial growth is found | Initial | Complies | Complies | Complies |

The results described above show that when stored for 24 months at 5° C., Formulation F1 showed no visible particulate contamination, clarity and opalescence<=RS III, and visual color<=BY7 (brown yellow 7). Formulation F1 also demonstrated 111% of the TNF-neutralization capacity of the reference standard, 83.9% lysine variants, 99.3% monomers, 11 particles>=10 µm, and no particles>=25 µm. Furthermore, F1 maintained a stable pH of 5.3 and showed no evidence of microbial growth. When stored for 6 months at 25° C./60% R.H., Formulation F1 showed 0.1 visible particles, clarity and opalescence<=RS III, visual color<=BY7, 81% of the TNF-neutralization capacity of the reference standard, 65% lysine variants, 98.5% monomers, 102 particles>=10 µm, 2 particles>=25 µm, a stable pH of 5.3 and no evidence of microbial growth. When stored for 6 months at 45° C./75% R.H., Formulation F1 showed no visible particles, clarity and opalescence<=RS IV, visual color<=BY6, 68% of the TNF-neutralization capacity of the reference standard, 11.9% lysine variants, 92.9% monomers, 98 particles>=10 µm, 2 particles>=25 µm, and no evidence of microbial growth.

The results for Formulation F3 are presented in Table 22.

TABLE 22

Stability Summary Report for Formulation F3

| Test Item | Component | Specification | Duration of Testing | Storage Conditions [° C./% r.H.] | | |
|---|---|---|---|---|---|---|
| | | | | 5° C. | 25° C./ 60% R.H. | 40° C./ 75% R.H. |
| Participate contamination: visible particles | Visible particles | NMT 4.5 | Initial | 0.0 | 0.0 | 0.0 |
| | | | 3 months | 0.0 | 0.0 | 0.2 |
| | | | 6 months | 0.2 | 0.1 | 0.0 |
| | | | 9 months | 0.0 | — | — |
| | | | 12 months | 0.0 | — | — |
| | | | 18 months | 0.0 | — | — |
| | | | 24 months | 0.0 | — | — |
| Clarity and Opalescence | Assessment | Not more opalescent than reference suspension IV | Initial | <=RS II | <=RS II | <=RS II |
| | | | 3 months | <=RS II | <=RS II | <=RS II |
| | | | 6 months | <=RS II | <=RS II | <=RS II |
| | | | 9 months | <=RS II | — | — |
| | | | 12 months | <=RS II | — | — |
| | | | 18 months | <=RS II | — | — |
| | | | 24 months | <=RS II | — | — |
| Color of solution (visual) | BY-Scale | Report value | Initial | <=BY 7 | <=BY 7 | <=BY 7 |
| | | | 3 months | <=BY 7 | <=BY 7 | <=BY 7 |
| | | | 6 months | <=BY 7 | <=BY 7 | <=BY 6 |
| | | | 9 months | <=BY 7 | — | — |
| | | | 12 months | <=BY 7 | — | — |
| | | | 18 months | <=BY 7 | — | — |
| | | | 24 months | <=BY 7 | — | — |
| In vitro TNF-Neutralization | (cytotoxicity test) [%] | 80% to 125% of the neutralization capacity of the reference standard | Initial | 87 | 87 | 87 |
| | | | 3 months | 101 | 106 | 89 |
| | | | 6 months | 100 | 101 | 90 |
| | | | 9 months | 98 | — | — |
| | | | 12 months | 96 | — | — |
| | | | 18 months | 96 | — | — |
| | | | 24 months | 98 | — | — |
| | Fiducial Limit of error (p = 0.95) lower Limit [%] | NLT 64 | Initial | 85.4 | 85.4 | 85.4 |
| | | | 3 months | 92.9 | 88.1 | 80.6 |
| | | | 6 months | 98.3 | 97.4 | 86.5 |
| | | | 9 months | 97.0 | — | — |
| | | | 12 months | 93.3 | — | — |
| | | | 18 months | 93.9 | — | — |
| | | | 24 months | 96.7 | — | — |

TABLE 22-continued

Stability Summary Report for Formulation F3

| Test Item | Component | Specification | Duration of Testing | 5° C. | 25° C./ 60% R.H. | 40° C./ 75% R.H. |
|---|---|---|---|---|---|---|
| | Fiducial Limit of error (p = 0.95) upper Limit [%] | NMT 156 | Initial | 88.5 | 88.5 | 88.5 |
| | | | 3 months | 110.5 | 122.2 | 97.9 |
| | | | 6 months | 101.7 | 103.8 | 92.6 |
| | | | 9 months | 99.8 | — | — |
| | | | 12 months | 99.2 | — | — |
| | | | 18 months | 98.1 | — | — |
| | | | 24 months | 99.6 | — | — |
| Cation Exchange Chromatography (CEX-HPLC) | Sum of lysine variants [%] | NLT 75 | Initial | 86.8 | 86.8 | 86.8 |
| | | | 3 months | 86.6 | 77.8 | 32.8 |
| | | | 6 months | 86.4 | 70.1 | 16.5 |
| | | | 9 months | 86.0 | — | — |
| | | | 12 months | 86.2 | — | — |
| | | | 18 months | 85.2 | — | — |
| | | | 24 months | 85.1 | — | — |
| Size exclusion chromatography (SE-HPLC) | Principal peak (monomer) [%] | NLT 98 | Initial | 99.7 | 99.7 | 99.7 |
| | | | 3 months | 99.6 | 99.2 | 96.9 |
| | | | 6 months | 99.5 | 98.8 | 93.8 |
| | | | 9 months | 99.5 | — | — |
| | | | 12 months | 99.5 | — | — |
| | | | 18 months | 99.4 | — | — |
| | | | 24 months | 99.4 | — | — |
| Participate contamination - Sub-visible Particles* | Particles >=10 µm [/container] | NMT 6000 | Initial | 10 | 10 | 10 |
| | | | 3 months | 12 | 45 | 73 |
| | | | 6 months | 22 | 157 | 275 |
| | | | 9 months | 50 | — | — |
| | | | 12 months | 54 | — | — |
| | | | 18 months | 45 | — | — |
| | | | 24 months | 14 | — | — |
| | Particles >=25 µm [/container] | NMT 600 | Initial | 0 | 0 | 0 |
| | | | 3 months | 0 | 0 | 1 |
| | | | 6 months | 0 | 2 | 9 |
| | | | 9 months | 0 | — | — |
| | | | 12 months | 1 | — | — |
| | | | 18 months | 0 | — | — |
| | | | 24 months | 0 | — | — |
| Container Closure Integrity | Assessment | Tight | Initial | Complies | Complies | Complies |
| | | | 6 months | Complies | Complies | Complies |
| | | | 24 months | Complies | — | — |
| pH | Single values | 4.7 to 5.7 | Initial | 5.2 | 5.2 | 5.2 |
| | | | 3 months | 5.3 | 5.3 | 5.3 |
| | | | 6 months | 5.2 | 5.2 | 5.3 |
| | | | 9 months | 5.3 | — | — |
| | | | 12 months | 5.4 | — | — |
| | | | 18 months | 5.2 | — | — |
| | | | 24 months | 5.1 | — | — |
| Microbial quality | Sterility drug product | No evidence of microbial growth is found | Initial | Complies | Complies | Complies |

The results provided in Table 22 indicate that when stored for 24 months at 5° C., Formulation F3 showed no visible particulate contamination, clarity and opalescence<=RS II, and visual color<=BY7. Formulation F3 showed 98% of the TNF-neutralization capacity of the reference standard, 85.1% lysine variants, 99.4% monomers, 14 particles>=10 µm, and no particles>=25 µm. The pH showed little change and there was no evidence of microbial growth.

When stored for 6 months at 25° C./60% R.H., Formulation F3 showed no visible particles, clarity and opalescence<=RS II, and visual color<=BY7. Also, formulation F3 showed 101% of the TNF-neutralization capacity of the reference standard, 97.4% lysine variants, 70.1% monomers, 157 particles>=10 µm, and 2 particles>=25 µm. The pH was stable and there was no evidence of microbial growth.

When stored for 6 months at 45° C./75% R.H., Formulation F3 showed no visible particles, clarity and opalescence<=RS II, and visual color<=BY6. Also, formulation F3 showed 90% of the TNF-neutralization capacity of the reference standard, 16.5% lysine variants, 93.8% monomers, 275 particles>=10 µm, and 9 particles>=25 µm. The pH was quite stable, and there was no evidence of microbial growth.

The results for Formulation F4 are presented in Table 23.

TABLE 23

Stability Summary Report for Formulation F4

| Test Item | Component | Specification | Duration of Testing | 5° C. | 25° C./ 60% R.H. | 40° C./ 75% R.H. |
|---|---|---|---|---|---|---|
| | | | | | Storage Conditions [° C./% r.H.] | |
| Appearance | Visual particles | NMT 4.5 | Initial | 0.0 | 0.0 | 0.0 |
| | | | 3 months | 0.0 | 0.0 | 0.0 |
| | | | 6 months | 0.0 | 0.0 | 0.0 |
| | | | 9 months | 0.0 | — | — |
| | | | 12 months | 0.0 | — | — |
| | | | 18 months | 0.0 | — | — |
| Clarity | Assessment | Not more opalescent than reference suspension IV | Initial | <=RS II | <=RS II | <=RS II |
| | | | 3 months | <=RS II | <=RS II | <=RS II |
| | | | 6 months | <=RS II | <=RS II | <=RS II |
| | | | 9 months | <=RS II | — | — |
| | | | 12 months | <=RS II | — | — |
| | | | 18 months | <=RS II | — | — |
| Color | BY-Scale | | Initial | <=BY 7 | <=BY 7 | <=BY 7 |
| | | | 3 months | <=BY 6 | <=BY 6 | <=BY 6 |
| | | | 6 months | <=BY 7 | <=BY 7 | <=BY 6 |
| | | | 9 months | <=BY 7 | — | — |
| | | | 12 months | <=BY 7 | — | — |
| | | | 18 months | <=BY 7 | — | — |
| In vitro TNF-Neutralisation (Cytotoxizitatstest) | (cytotoxicity test) [%] | 80% to 125% of the neutralization capacity of the reference standard | Initial | 111 | 111 | 111 |
| | | | 3 months | 105 | 101 | 80 |
| | | | 6 months | 97 | 101 | 76 |
| | | | 9 months | 112 | — | — |
| | | | 12 months | 97 | — | — |
| | | | 18 months | 104 | — | — |
| | Fiducial Limit of error (p = 0.95) lower Limit [%] | NLT 64 | Initial | 105.2 | 105.2 | 105.2 |
| | | | 3 months | 103.2 | 100.1 | 79.2 |
| | | | 6 months | 92.9 | 97.5 | 74.7 |
| | | | 9 months | 109.3 | — | — |
| | | | 12 months | 90.2 | — | — |
| | | | 18 months | 101.2 | — | — |
| | Fiducial Limit of error (p = 0.95) upper Limit [%] | NMT 156 | Initial | 116.3 | 116.3 | 116.3 |
| | | | 3 months | 106.2 | 102.7 | 80.4 |
| | | | 6 months | 101.1 | 103.5 | 78.1 |
| | | | 9 months | 113.9 | — | — |
| | | | 12 months | 104.9 | — | — |
| | | | 18 months | 107.5 | — | — |
| Cation Exchange Chromatography (CEX-HPLC) | Sum of lysine variants [%] | NLT 75 | Initial | 85.5 | 85.5 | 85.5 |
| | | | 3 months | 85.8 | 76.8 | 31.6 |
| | | | 6 months | 85.4 | 68.7 | 15.7 |
| | | | 9 months | 85.2 | — | — |
| | | | 12 months | 84.5 | — | — |
| | | | 18 months | 84.4 | — | — |
| Size exclusion chromatography (SE-HPLC) | Principal peak (monomer) [%] | NLT 98 | Initial | 99.7 | 99.7 | 99.7 |
| | | | 3 months | 99.6 | 99.1 | 96.5 |
| | | | 6 months | 99.6 | 98.8 | 93.1 |
| | | | 9 months | 99.5 | — | — |
| | | | 12 months | 99.5 | — | — |
| | | | 18 months | 99.4 | — | — |
| Participate contamination - Sub-visible Particles | Particles >=10 μm [/container] | NMT 6000 | Initial | 17 | 17 | 17 |
| | | | 3 months | 51 | 174 | 207 |
| | | | 6 months | 39 | 144 | 218 |
| | | | 9 months | 82 | — | — |
| | | | 12 months | 57 | — | — |
| | Particles >=25 μm [/container] | NMT 600 | Initial | 0 | 0 | 0 |
| | | | 3 months | 0 | 1 | 5 |
| | | | 6 months | 0 | 1 | 1 |
| | | | 9 months | 1 | — | — |
| | | | 12 months | 2 | — | — |
| Container closure Integrity | Assessment | Must comply (no blue coloration) | Initial | Complies | Complies | Complies |
| | | | 6 months | Complies | Complies | Complies |
| pH | Single values | 4.7 to 5.7 | Initial | 5.1 | 5.1 | 5.1 |
| | | | 3 months | 5.2 | 5.2 | 5.1 |
| | | | 6 months | 5.2 | 5.1 | 5.2 |
| | | | 9 months | 5.2 | — | — |
| | | | 12 months | 5.2 | — | — |
| | | | 18 months | 5.1 | — | — |

TABLE 23-continued

Stability Summary Report for Formulation F4

| Test Item | Component | Specification | Duration of Testing | Storage Conditions [° C./% r.H.] | | |
|---|---|---|---|---|---|---|
| | | | | 5° C. | 25° C./ 60% R.H. | 40° C./ 75% R.H. |
| Microbial quality | Sterility drug product | No evidence of microbial growth is found | Initial | Complies | Complies | Complies |

The results provided in Table 23 indicate that when stored for 18 months at 5° C., Formulation F4 showed no visible particulate contamination, clarity and opalescence<=RS II, and visual color<=BY7. Formulation F4 showed 104% of the TNF-neutralization capacity of the reference standard, 84.4% lysine variants, and 99.4% monomers. Furthermore, the pH was stable and there was no evidence of microbial growth.

When stored for 6 months at 25° C./60% R.H., Formulation F4 showed no visible particles, clarity and opalescence<=RS II, and visual color<=BY7. Formulation F4 showed 101% of the TNF-neutralization capacity of the reference standard, 68.7% lysine variants, 98.8% monomers, 144 particles>=10 μm, and 1 particle>=25 μm. Furthermore, the pH was quite stable and there was no evidence of microbial growth.

When stored for 6 months at 45° C./75% R.H., Formulation F4 showed no visible particles, clarity and opalescence<=RS II, and visual color<=BY6. Formulation F4 showed 76% of the TNF-neutralization capacity of the reference standard, 15.7% lysine variants, 93.1% monomers, 218 particles>=10 μm, and 1 particle>=25 μm. Furthermore, the pH was quite stable and there was no evidence of microbial growth.

In summary, the results of the long-term stability experiments, as presented in Tables 21-23, show that high concentration formulations F1, F3, and F4 were surprisingly stable when subjected to long term storage. The stability of these formulations was similar to the commercial formulation. Formulations F1 and F3 showed stability similar to the commercial formulation after long term storage for at least 24 months. Formulation F4 showed stability similar to the commercial formulation after long term storage for at least 18 months.

Example 7

Room Temperature Storage Stability of High Concentration Anti-TNFa Antibody

Liquid pharmaceutical products containing therapeutic antibodies often require storage at 2-8° C. until end-of-shelf-life. Cooling is therefore also required by patients between purchasing of the medicines until use. Depending on the proposed dosing regimen, this can result in storage times under patient's responsibility in the case of self-administration drugs for up to several weeks.

Therefore, drugs that do not require storage under refrigerated conditions display both a significant increase in patient convenience for home care products and reduction of drug quality concerns in case of improper storage, thereby reducing complaint rates and temperature excursion investigations.

The currently marketed Adalimumab containing product (Humira) was successfully reformulated at a higher protein concentration as Formulation F3, as described above in Examples 1-6. The following stability data for Formulation F3 resulted in findings of improved stability against protein degradation. The resulting degradation kinetics measured at 25° C. complied with requirements for ambient storage for up to 3 months.

For general long-term stability data related to storage at 25° C. ofr Formulation F3, see Example 6 above.

The following data describes long-term storage characteristics for Formulation F3. The data shows that even after 18 months and 24 months of long-term storage at 2-5° C., additional storage at 25° C./30° C. is acceptable.

TABLE 24

24m storage of F3 at 2-8° C., followed by 7 days/14 days at accelerated conditions (25° C., 30° C.)

| Test criterion | Specification | Characteristic: | t0 (24M 5° C.) | +7 Days | | +14 Days | |
|---|---|---|---|---|---|---|---|
| | | | | 25° C. | 30° C./65% R.H. | 25° C. | 30° C./65% R.H. |
| Appearance | colourless to slightly yellow solution | | complies | complies | complies | complies | complies |
| Visible particles* | single vial ≤ 2=> practically free from visible particulate matter 1 vial > 10=> | | 0.0 | Value per analyst: 3 × 0; single vial ≤ 2=> practically free from visible particulate matter | Value per analyst: 3 × 0; single vial ≤ 2=> practically free from visible particulate matter | Value per analyst: 3 × 0; single vial ≤ 2=> practically free from visible particulate matter | Value per analyst: 3 × 0; single vial ≤ 2=> practically free from visible particulate matter |
| Size exclusion HPLC | Purity % monomer NLT 98% | aggregate monomer fragments | 0.4 99.4 0.2 | 0.4 99.3 0.2 | 0.4 99.3 0.3 | 0.4 99.3 0.3 | 0.4 99.2 0.3 |
| Cation exchange | NMT 8% NMT 16% | first acid region second acid region | 2.7 10.5 | 2.8 10.9 | 3.0 11.4 | 2.9 11.6 | 3.3 12.7 |

TABLE 24-continued 24m storage of F3 at 2-8° C., followed by 7 days/14 days at accelerated conditions (25° C., 30° C.)

| Test criterion | Specification | Characteristic: | t0 (24M 5° C.) | +7 Days 25° C. | +7 Days 30° C./65% R.H. | +14 Days 25° C. | +14 Days 30° C./65% R.H. |
|---|---|---|---|---|---|---|---|
| HPLC | NLT 75% | sum Lysine variants | 85.1 | 84.2 | 83.4 | 83.0 | 81.2 |
|  | NMT 4% | peak between Lysine 1 and Lysine 2 | 1.5 | 1.7 | 1.9 | 1.6 | 1.8 |
|  | report value [%] | peaks after Lysine 2 | 0.2 | 0.4 | 0.4 | 0.9 | 1.0 |
| PCS | report value [%] | Z-Average | 1.390 | 1.365 | 1.395 | 1.397 | 1.420 |
|  |  | PdI | 0.193 | 0.176 | 0.188 | 0.175 | 0.210 |

TABLE 25

18m storage at 2-8° C. of F3, followed by 7 days/14 days at accelerated conditions (25° C., 30° C.)

| Test criterion | Specification | Characteristics | t0 (18M 5° C.) | +7 Days 25° C. | +7 Days 30° C./65% R.H. | +14 Days 25° C. | +14 Days 30° C./65% R.H. |
|---|---|---|---|---|---|---|---|
| Appearance | colourless to slightly yellow solution |  |  | complies | complies | complies | complies |
| Visible particles* | single vial ≤ 2=> practically free from visible particulate matter 1 vial > 10=> inform lab manager |  |  | Value per analyst: 3 × 0; single vial ≤ 2=> practically free from visible particulate matter | Value per analyst: 3 × 0; single vial ≤ 2=> practically free from visible particulate matter | Value per analyst: 3 × 0; single vial ≤ 2=> practically free from visible particulate matter | Value per analyst: 3 × 0; single vial ≤ 2=> practically free from visible particulate matter |
| Participate contamination, subvisible particles* | particles ≤ 10 μm: ≤6000 particles/container particles ≤ 25 μm: ≤600 particles/container | ≤1 μm/1 ml ≤10 μm/1 ml ≤25 μm/1 ml |  | 2250 6 0 | 5623 7 0 | 9355 39 0 | 10252 45 1 |
| PCS | report value [%] | Z-Average PdI |  | 2.378 0.102 | 2.344 0.077 | 2.353 0.077 | 2.358 0.077 |

Example 8

Conductivity of High Concentration Anti-TNFa Antibody Formulations

The conductivity of the high concentration anti-TNFα antibody formulations F3 and F4 (see Examples 1-6, supra) was determined using an InoLab Cond Level2 WTW device normalized to 25° C. Table 26 shows the influence of non-ionic excipients on the conductivity of the F3 and F4 adalimumab formulations.

TABLE 26

Conductivity of Formulations F3 and F4

| Sample | Temperature [° C.] | Conductivity [μS/cm] |
|---|---|---|
| Adalimumab DP F3 | | |
| 1 | 22.4 | 663 |
| 2 | 22.4 | 651 |
| 3 | 23.8 | 660 |
| 4 | 21.4 | 715 |
| 5 | 21.7 | 691 |
| 6 | 23.1 | 680 |
| 7 | 23.3 | 644 |
| 8 | 22.9 | 647 |

TABLE 26-continued

Conductivity of Formulations F3 and F4

| Sample | Temperature [° C.] | Conductivity [μS/cm] |
|---|---|---|
| Adalimumab DP F4 | | |
| 1 | 22.0 | 797 |
| 2 | 22.9 | 746 |

As described above in Table 26, average conductivity for both formulations F3 and F4 was less than 2 mS/cm.

Example 9

Dynamic Light Scattering (DLS) of High Concentration Anti-TNFa Antibody Formulations Dynamic light scattering analysis of diluted solutions was used to assess the hydrodynamic diameter (reported as the mean or Z-average size, calculated by cumulants analysis of the DLS measured intensity autocorrelation function and polydispersity index, PDI, of the size distribution of particles). DLS measurements were specifically used to detect low amounts of higher molecular weight species, e.g. aggregates, in a size distribution, since those species possess higher scattering intensity (proportional to d6) and, therefore, will influence the Z-average and Polydispersity Index (PDI) as an indicator of the Z-average size distribution significantly.

A 150 μL sample of each of formulations F3 and F4 (see examples 1-6 above) was measured to analyze the average size of the particles (Z-average) and the Polydispersity Index (PDI), an indicator of the "broadness" of the particle size distribution using DLS. The results are shown below. DLS data did not show any signs of the development of higher molecular weight aggregates, since the polydispersity index, a sensitive indicator for low levels of higher molecular weight sub-populations did not increase significantly.

Formulation F3

| Sample No. | ZAve (nm) | PDI |
|---|---|---|
| 1 | 2.4 | n.a. |
| 2 | 2.3 | 0.08 |
| 3 | 2.3 | 0.14 |
| 4 | 2.3 | 0.09 |

Formulation F4

| Sample No. | ZAve (nm) | PDI |
|---|---|---|
| 1 | 1.3 | n.a. |
| 2 | 2.5 | n.a. |

As described above, the z-average measurement for both F3 and F4 was less than 4 nm. This low hydrodynamic diameter is representative of the fact that both formulations F3 and F4 do not contain additional excipients other than a polysorbate and a polyol or a polysorbate.

Example 10

Factors Influencing the Stability of High Concentration Anti-TNFa Antibody Formulations The effect of varying mannitol concentrations and polysorbate concentrations on the stability of adalimumab in water was examined.

Figure 3A:
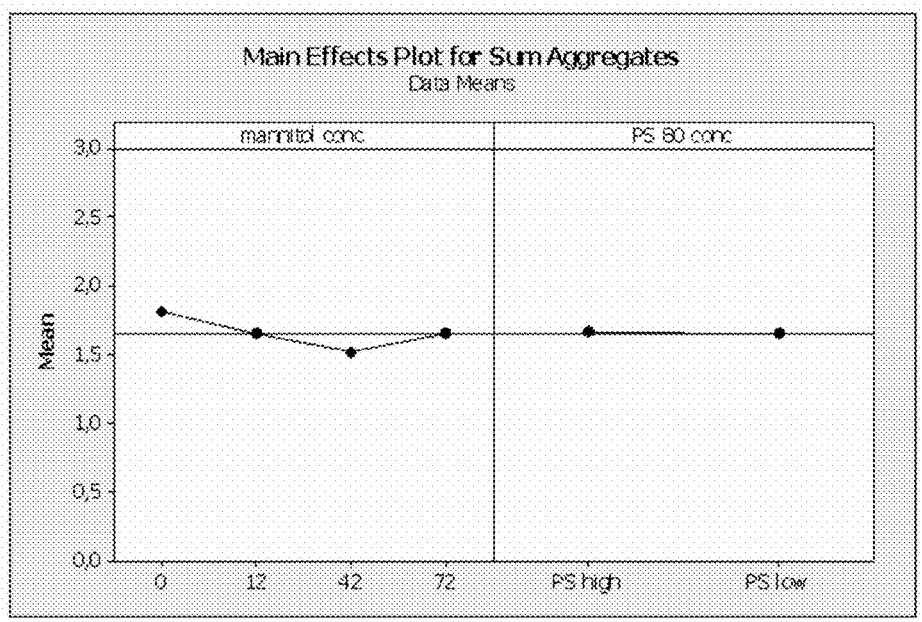
FIGS. 3A and 3B are graphs that show the stability of the various adalimumab formulations assessed by the number of sum aggregates in the formulations (3A) or the sum aggregates (3B) over a range of polysorbate or a range of polyol.
Figure 3B:
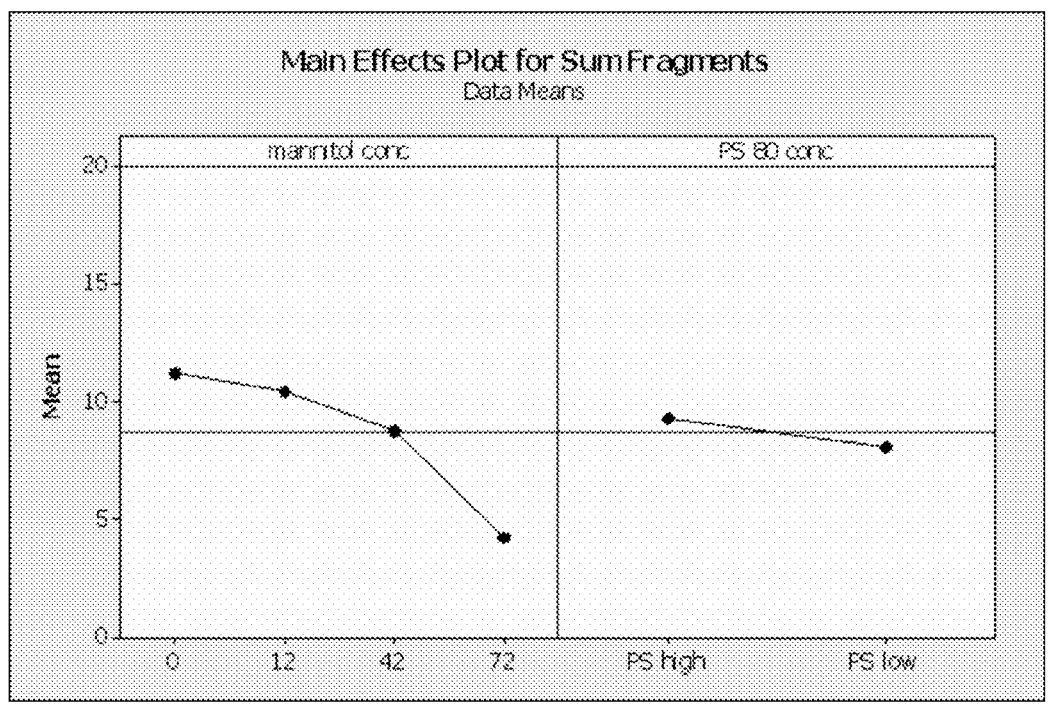

Formulations containing 100 mg/ml of adalimumab in water were prepared. Subsequently, various concentrations of either mannitol or polysorbate were added in a concentration range to determine the impact of each excipient on the stability of the formulation, as measured by aggregation and fragmentation. The concentrations of polysorbate and mannitol ranged from 0.1 to 1.0 mg/ml and 0-72 mg/ml, respectively, as shown in FIGS. 3A and 3B. As shown in FIG. 3A, varying the concentration of mannitol from about 12 to about 72 mg/ml had a minimal effect on the stability of adalimumab. Similarly, varying the concentration of polysorbate-80 from about 0.1 to about 1.0 mg/ml had no effect on the stability of adalimumab.

INCORPORATION BY REFERENCE

The contents of all cited references (including, for example, literature references, patents, patent applications, and websites) that maybe cited throughout this application are hereby expressly incorporated by reference in their entirety for any purpose. The practice of the present invention will employ, unless otherwise indicated, conventional techniques of protein formulations, which are well known in the art.

EQUIVALENTS

The invention may be embodied in other specific forms without departing from the spirit or essential characteristics thereof. The foregoing embodiments are therefore to be considered in all respects illustrative rather than limiting of the invention described herein. Scope of the invention is thus indicated by the appended claims rather than by the foregoing description, and all changes that come within the meaning and range of equivalency of the claims are therefore intended to be embraced herein.

The invention claimed is:

1. A liquid aqueous formulation comprising:
   (1) 100 mg/ml of adalimumab;
   (2) 1.0 mg/ml of polysorbate-80; and,
   (3) 42 mg/ml of mannitol;
      wherein the formulation has a pH of 4.7 to 5.7 and does not contain a buffer or a salt, and wherein injection of the formulation into a human subject results in a Pain Visual Analog Scale (VAS) score of less than 1.0.

2. A liquid aqueous formulation comprising:
   (1) 100 mg/ml of adalimumab;
   (2) 1.0 mg/ml of polysorbate-80; and,
   (3) 42 mg/ml of mannitol;
      wherein the formulation has a pH of 4.7 to 5.7 and does not contain a buffer or a salt, and
      wherein injection of the formulation reduces pain associated with the injection in a human subject by at least about 50% when compared to injection of an otherwise identical formulation that comprises a salt and/or a buffer.

3. A liquid aqueous formulation consisting essentially of:
   (1) 100 mg/ml of adalimumab;
   (2) 1.0 mg/ml of polysorbate-80; and
   (3) 42 mg/ml of mannitol,
      wherein the formulation has a pH of 4.7 to 5.7, and wherein injection of the formulation into a human subject results in a Pain Visual Analog Scale (VAS) score of less than 1.0.

4. The formulation of claim 2, wherein the pain associated with the injection is assessed using a Pain Visual Analog Scale (VAS).

5. The formulation of claim 2, wherein the otherwise identical formulation comprises a citrate phosphate buffer and sodium chloride.

6. A liquid aqueous formulation comprising:
   (1) 100 mg/ml of adalimumab;
   (2) 1.0 mg/ml of polysorbate-80; and,
   (3) 42 mg/ml of mannitol;
      wherein the formulation has a pH of 4.7 to 5.7, and wherein the formulation is stable up to about 30° C. for at least 6 days.

7. The formulation of claim 6, wherein the formulation is stable up to about 30° C. for 10 days.

8. A liquid aqueous formulation comprising:
   (1) 100 mg/ml of adalimumab;
   (2) 1.0 mg/ml of polysorbate-80; and,
   (3) 42 mg/ml of mannitol;
      wherein the formulation has a pH of 4.7 to 5.7, and wherein the formulation has a characteristic selected from the group consisting of:
      a) a conductivity of less than about 2 mS/cm;
      b) a hydrodynamic diameter ($D_h$) which is at least about 50% less than the $D_h$ of the protein in a buffered solution at a given concentration; and
      c) a hydrodynamic diameter ($D_h$) of less than about 4 nm.

9. A liquid aqueous formulation consisting essentially of 1.0 mg/ml of polysorbate-80 and 40 mg of adalimumab,
   wherein the concentration of adalimumab is 100 mg/ml, and
   wherein the formulation has a pH of 4.7 to 5.7, and
   wherein the formulation provides increased bioavailability of the adalimumab to a human subject upon subcutaneous injection of the formulation relative to a formulation comprising a citrate phosphate buffer, sodium chloride, and mannitol.

10. A liquid aqueous formulation consisting essentially of 1.0 mg/ml of polysorbate-80 and 40 mg of adalimumab, wherein the formulation has an adalimumab concentration of 100 mg/ml a pH of 4.7-5.7, and
    wherein the formulation provides increased bioavailability of adalimumab in a human subject upon subcutaneous injection of the formulation, such that adalimumab has an area under the curve, 0-360 minutes ($AUC_{0-360}$) greater than 1300 µg/hr/ml.

11. A pre-filled syringe or autoinjector device, comprising the formulation of any one of claims 1-7, 8, 9 and 10.

* * * * *